US012029786B2

(12) United States Patent
Tang et al.

(10) Patent No.: US 12,029,786 B2
(45) Date of Patent: Jul. 9, 2024

(54) COMPOSITION AND METHOD OF mRNA VACCINES AGAINST NOVEL CORONAVIRUS INFECTION

(71) Applicant: RNAimmune, Inc., Gaithersburg, MD (US)

(72) Inventors: Shenggao Tang, Guangzhou (CN); Dong Shen, Baltimore, MD (US); Chun Lu, Montreal (CA); Ziyang He, Potomac, MD (US); Jiaxi He, Baltimore, MD (US); Patrick Y. Lu, Potomac, MD (US)

(73) Assignee: RNAimmune, Inc., Germantown, MD (US)

( * ) Notice: Subject to any disclaimer, the term of this patent is extended or adjusted under 35 U.S.C. 154(b) by 155 days.

(21) Appl. No.: 17/170,876

(22) Filed: Feb. 8, 2021

(65) Prior Publication Data

US 2022/0040292 A1 Feb. 10, 2022

Related U.S. Application Data

(60) Provisional application No. 63/130,581, filed on Dec. 24, 2020, provisional application No. 63/058,463, filed on Jul. 29, 2020, provisional application No. 62/971,834, filed on Feb. 7, 2020.

(51) Int. Cl.

| | |
|---|---|
| ***A61K 39/215*** | (2006.01) |
| ***A61K 9/00*** | (2006.01) |
| ***A61K 9/51*** | (2006.01) |
| ***A61P 31/14*** | (2006.01) |
| ***C07K 14/005*** | (2006.01) |
| ***C12N 7/00*** | (2006.01) |
| *A61K 39/00* | (2006.01) |
| *A61M 11/00* | (2006.01) |

(52) U.S. Cl.

CPC .......... *A61K 39/215* (2013.01); *A61K 9/0019* (2013.01); *A61K 9/5123* (2013.01); *A61P 31/14* (2018.01); *C07K 14/005* (2013.01); *C12N 7/00* (2013.01); *A61K 2039/53* (2013.01); *A61K 2039/54* (2013.01); *A61K 2039/544* (2013.01); *A61K 2039/55555* (2013.01); *A61M 11/00* (2013.01); *C12N 2770/20022* (2013.01); *C12N 2770/20034* (2013.01); *C12N 2770/20071* (2013.01)

(58) Field of Classification Search

None

See application file for complete search history.

(56) References Cited

U.S. PATENT DOCUMENTS

| | | | | |
|---|---|---|---|---|
| 10,973,909 | B1 | 4/2021 | Csiszovszki et al. | |
| 2017/0340725 | A1 | 11/2017 | Ciaramella et al. | |
| 2019/0240317 | A1* | 8/2019 | Ciaramella | A61P 31/14 |
| 2019/0351048 | A1 | 11/2019 | Rauch | |
| 2021/0316002 | A1 | 10/2021 | Ellis | |
| 2021/0388032 | A1 | 12/2021 | Langedijk et al. | |
| 2022/0064631 | A1 | 3/2022 | Barna et al. | |
| 2023/0108926 | A1 | 4/2023 | Tang et al. | |
| 2023/0117167 | A1* | 4/2023 | Mueller | A61P 31/14 424/186.1 |

FOREIGN PATENT DOCUMENTS

| | | | | |
|---|---|---|---|---|
| CN | 115160413 | A | 10/2022 | |
| WO | WO-2018/160690 | | 9/2018 | |
| WO | WO-2021/247779 | A1 | 12/2021 | |
| WO | WO-2022/072910 | A1 | 4/2022 | |

OTHER PUBLICATIONS

Lu et al. The Lancet vol. 395, Issue 10224 pp. 565-574 (Year: 2020).*
Ljungberg et al. Expert Rev. Vaccines 14(2), 177-194 (Year: 2015).*
Midoux et al. (Expert Rev. Vaccines 14(2), 221-234 (Year: 2015).*
Seq ID# 1 prior art year of search 2023 (Year: 2023).*
Chan et al., "A familial cluster of pneumonia associated with the 2019 novel coronavirus indicating person-to-person transmission: a study of a family cluster", Lancet, 2020, vol. 395, pp. 514-523, Epub Jan. 24, 2020.
Genbank, Accession: QHD43416.1, Surface Glycoprotein [Wuhan searfood market pneumonia virus], Jan. 23, 2020, www.ncbi.nlm.nih.gov/protein/1791269090?sat=48&satkey=1085346.
Genbank_CP006842, Corynebacterium glyciniphilum AJ3170, complete genome GenBank Accession No. CP006842, Apr. 8, 2015, www.ncbi.nlm.nih.gov/nuccore/CP006842.
Huang et al., "Clinical features of patients infected with 2019 novel coronavirus in Wuhan, China", Lancet, Feb. 15, 2020, vol. 395, pp. 497-506.
International Search Report and Written Opinion for PCT/US2021/017149 dated Sep. 23, 2021, 21 pages.
Liu et al., "Potential inhibitors against 2019-nCOV coronavirus M protease from clinically approved medicines", J. Genet Genomics, Feb. 20, 2020, vol. 47(2), pp. 119-121.
Lu et al., "Genomic characterisation and epidemiology of 2019 novel coronavirus: implications for virus origins and receptor binding", Lancet, 2020, vol. 395, pp. 565-574, epub 2020.
Menachery et al., "A SARS-like cluster of circulating bat coronaviruses shows potential for human emergence", Nat Med. 2015, vol. 21(12), pp. 1508-1513.

(Continued)

*Primary Examiner* — Shanon A. Foley
*Assistant Examiner* — Myron G Hill
(74) *Attorney, Agent, or Firm* — Foley & Lardner LLP

(57) ABSTRACT

Compositions and methods are provided for potent mRNA vaccines for prevention and treatment of 2019 novel Coronavirus (2019-nCoV) infections. The compositions include a pharmaceutical composition containing one or more mRNA molecules encoding spike protein epitopes, including mutated epitopes, or mRNA cocktails that encode critical viral genes together with pharmaceutically acceptable polymeric nanoparticle carriers and liposomal nanoparticle carriers. Methods for stimulating system immune responses and treatment are provided, including subcutaneous, intraperitoneal and intramuscular injections.

19 Claims, 26 Drawing Sheets

Specification includes a Sequence Listing.

(56) References Cited

OTHER PUBLICATIONS

NCBI_NC_045512.2, Wuhan seafood market pneumonia virus isolate Wuhan-Hu-1, complete genome, NCBI accession No. NC_045512.2, Jan. 28, 2020, www.ncbi.nlm.nih.gov/nuccore/1798174254?sat=4&satkey=350670880.
Zhou et al., "A pneumonia outbreak associated with a new coronavirus of probably bat origin", Nature, 2020, vol. 579, pp. 270-273, Epub Feb. 3, 2020.
U.S. Appl. No. 18/385,879, filed Oct. 31, 2023.
CDC COVID-19 Treatment Guidelines, Dec. 2023, pp. 18-21, available from https://files.covid 19treatmentguidelines. nih.gov/guidelines/section/section_53.pdf (2023).
Kon et al., "Principles for designing an optimal mRNA lipid nanoparticle vaccine," Curr. Opin. Biotechnol., 73:329-336 (2022).
Nicholson et al., "Tales of Detailed Poly(A) Tails," Trends in Cell Biology, 29(3):191-200 (Mar. 2019).
Shi et al., "RBD-mRNA vaccine induces broadly neutralizing antibodies against Omicron and multiple other variants and protects mice from SARS-CoV-2 challenge," Transl. Res., 248:11-21 (Oct. 2022).
Non-Final Office Action on U.S. Appl. No. 18/385,879 DTD Mar. 8, 2024, 13 pages.
Extended European Search Report on EP 21750867.0 DTD Apr. 3, 2024, 8 pages.

* cited by examiner

Anti-β-Actin antibody
(Product # ab49900)

Western Blot

SARS-CoV/SARS-CoV-2 Spike Protein S2
Monoclonal Antibody (Product # MA5-35946)

Figure 4A

Spike Protein ORF clone 1 (MN996531: viral cDNA: 21523-23040) SEQ ID NO:1 atgttctt gttaacaact 21541
aaacgaacaa tgtttgtttt tcttgtttta ttgccactag tctctagtca gtgtgttaat cttacaacca gaactcaatt
accccctgca tacactaatt ctttcacacg tggtgtttat taccctgaca aagttttcag atcctcagtt ttacattcaa
ctcaggactt gttcttacct ttcttttcca atgttacttg gttccatgct atacatgtct ctgggaccaa tggtactaag
aggtttgata accctgtcct accatttaat gatggtgttt attttgcttc cactgagaag tctaacataa taagaggctg
gatttttggt actactttag attcgaagac ccagtcccta cttattgtta ataacgctac taatgttgtt attaaagtct
gtgaatttca attttgtaat gatccatttt tgggtgttta ttaccacaaa aacaacaaaa gttggatgga aagtgagttc
agagtttatt ctagtgcgaa taattgcact tttgaatatg tctctcagcc ttttcttatg gaccttgaag gaaaacaggg
taatttcaaa aatcttaggg aatttgtgtt taagaatatt gatggttatt ttaaaatata ttctaagcac acgcctatta
atttagtgcg tgatctccct cagggttttt cggctttaga accattggta gatttgccaa taggtattaa catcactagg
tttcaaactt tacttgcttt acatagaagt tatttgactc ctggtgattc ttcttcaggt tggacagctg gtgctgcagc
ttattatgtg ggttatcttc aacctaggac ttttctatta aaatataatg aaaatggaac cattacagat gctgtagact
gtgcacttga ccctctctca gaaacaaagt gtacgttgaa atccttcact gtagaaaaag gaatctatca aacttctaac
tttagagtcc aaccaacaga atctattgtt agatttccta atattacaaa cttgtgccct tttggtgaag tttttaacgc
caccagattt gcatctgttt atgcttggaa caggaagaga atcagcaact gtgttgctga ttattctgtc ctatataatt
ccgcatcatt ttccactttt aagtgttatg gagtgtctcc tactaaatta aatgatctct gctttactaa tgtctatgca
gattcatttg taattagagg tgatgaagtc agacaaatcg ctccagggca aactggaaag attgctgatt ataattataa
attaccagat gattttacag gctgcgttat agcttggaat tctaacaatc ttgattctaa ggttggtggt aattataatt
acctgtatag attgtttagg aagtctaatc tcaaaccttt tgagagagat atttcaactg aaatctatca ggccggtagc
acaccttgta atggtgttga aggttttaat tgttactttc ctttacaatc atatggtttc

Figure 4B

Spike Protein ORF clone 2, (MN996531: viral cDNA: 23041-23740) SEQ ID NO:2

23041
caacccacta atggtgttgg ttaccaacca tacagagtag tagtactttc ttttgaactt ctacatgcac cagcaactgt
ttgtggacct aaaaagtcta ctaatttggt taaaaacaaa tgtgtcaatt tcaacttcaa tggtttaaca ggcacaggtg
ttcttactga gtctaacaaa aagtttctgc ctttccaaca atttggcaga gacattgctg acactactga tgctgtccgt
gatccacaga cacttgagat tcttgacatt acaccatgtt cttttggtgg tgtcagtgtt ataacaccag gaacaaatac
ttctaaccag gttgctgttc tttatcagga tgttaactgc acagaagtcc ctgttgctat tcatgcagat caacttactc
ctacttggcg tgtttattct acaggttcta atgtttttca aacacgtgca ggctgtttaa taggggctga acatgtcaac
aactcatatg agtgtgacat acccattggt gcaggtatat gcgctagtta tcagactcag actaattctc
ctcggcgggc acgtagtgta gctagtcaat ccatcattgc ctacactatg tcacttggtg cagaaaattc agttgcttac
tctaataact ctattgccat acccacaaat tttactatta gtgttaccac agaaattcta ccagtgtcta

Figure 4C

Spike Protein ORF clone 3 (MN996531: viral cDNA: 23740-24540) SEQ ID NO:3

23740 tgaccaagac atcagtagat tgtacaatgt acatttgtgg tgattcaact gaatgcagca atcttttgtt gcaatatggc
agtttttgta cacaattaaa ccgtgcttta actggaatag ctgttgaaca agacaaaaac acccaagaag ttttgcaca
agtcaaacaa atttacaaaa caccaccaat taaagatttt ggtggtttta attttcaca aatattacca gatccatcaa
aaccaagcaa gaggtcattt attgaagatc tacttttcaa caaagtgaca cttgcagatg ctggcttcat caaacaatat
ggtgattgcc ttggtgatat tgctgctaga gacctcattt gtgcacaaaa gtttaacggc cttactgttt tgccaccttt
gctcacagat gaaatgattg ctcaatacac ttctgcactg ttagcgggta caatcacttc tggttggacc tttggtgcag
gtgctgcatt acaaatacca tttgctatgc aaatggctta taggtttaat ggtattggag ttacacagaa tgttctctat
gagaaccaaa aattgattgc caaccaattt aatagtgcta ttggcaaaat tcaagactca ctttcttcca cagcaagtgc
acttggaaaa cttcaagatg tggtcaacca aaatgcacaa gctttaaaca cgcttgttaa acaacttagc tccaatttg
gtgcaatttc aagtgtttta aatgatatcc tttcacgtct tgacaaagtt gaggctgaag tgcaaattga taggttgatc

Figure 4D

Spike Protein ORF clone 4 (MN996531: viral cDNA: 24540-25371) SEQ ID NO:4

24540 acaggcagac ttcaaagttt gcagacatat gtgactcaac aattaattag agctgcagaa atcagagctt
ctgctaatct tgctgctact aaaatgtcag agtgtgtact tggacaatca aaaagagttg attttgtgg aaagggctat
catcttatgt ccttccctca gtcagcacct catggtgtag tcttcttgca tgtgacttat gtccctgcac aagaaaagaa
cttcacaact gctcctgcca tttgtcatga tggaaaagca cactttcctc gtgaaggtgt ctttgtttca aatggcacac
actggtttgt aacacaaagg aatttttatg aaccacaaat cattactaca gacaacacat ttgtgtctgg taactgtgat
gttgtaatag gaattgtcaa caacacagtt tatgatcctt tgcaacctga attagactca ttcaaggagg agttagataa
atattttaag aatcatacat caccagatgt tgatttaggt gacatctctg gcattaatgc ttcagttgta aacattcaaa
aagaaattga ccgcctcaat gaggttgcca agaatttaaa tgaatctctc atcgatctcc aagaacttgg
aaagtatgag cagtatataa aatggccatg gtacatttgg ctaggtttta tagctggctt gattgccata gtaatggtga
caattatgct ttgctgtatg accagttgct gtagttgtct caagggctgt tgttcttgtg gatcctgctg caaatttgat
gaagacgact ctgagccagt gctcaaagga gtcaaattac attacacata a

Figure 4E

ORF1a Polymerase Protein clone 1 (MN996531: viral cDNA: 6253-7140) SEQ ID NO:5

6253 gccacgta taaaccaaat acctggtgta tacgttgtct ttggagcaca aaaccagttg aaacatcaaa ttcgtttgat
gtactgaagt cagaggacgc gcagggaatg gataatcttg cctgcgaaga tctaaaacca gtctctgaag
aagtagtgga aaatcctacc atacagaaag acgttcttga gtgtaatgtg aaaactaccg aagttgtagg
agacattata cttaaaccag caaataatag tttaaaaatt acagaagagg ttggccacac agatctaatg gctgcttatg
tagacaattc tagtcttact attaagaaac ctaatgaatt atctagagta ttaggtttga aaacccttgc tactcatggt
ttagctgctg ttaatagtgt cccttgggat actatagcta attatgctaa gccttttctt aacaaagttg ttagtacaac
tactaacata gttacacggt gtttaaaccg tgtttgtact aattatatgc cttatttctt tactttattg ctacaattgt
gtacttttac tagaagtaca aattctagaa ttaaagcatc tatgccgact actatagcaa agaatactgt taagagtgtc
ggtaaatttt gtctagaggc ttcatttaat tatttgaagt cacctaattt ttctaaactg ataaatatta taatttggtt

Figure 4F tttactatta agtgtttgcc taggttcttt aatctactca accgctgctt taggtgtttt aatgtctaat ttaggcatgc cttcttactg tactggttac agagaaggct atttgaactc tactaatgtc actattgcaa cctactgtac tggttctata ccttgtagtg tttgtcttag tggtttagat

Figure 4G

ORF1b RdRp Protein clone 1 (MN996531: viral cDNA: 15253-16153) SEQ ID NO:6

15253 tagaaaac cctcacctta tgggttggga ttatcctaaa tgtgatagag ccatgcctaa catgcttaga attatggcct cacttgttct tgctcgcaaa catacaacgt gttgtagctt gtcacaccgt ttctatagat tagctaatga gtgtgctcaa gtattgagtg aaatggtcat gtgtggcggt tcactatatg ttaaaccagg tggaacctca tcaggagatg ccacaactgc ttatgctaat agtgttttta acatttgtca agctgtcacg gccaatgtta atgcactttt atctactgat ggtaacaaaa ttgccgataa gtatgtccgc aatttacaac acagacttta tgagtgtctc tatagaaata gagatgttga cacagacttt gtgaatgagt tttacgcata tttgcgtaaa catttctcaa tgatgatact ctctgacgat gctgttgtgt gtttcaatag cacttatgca tctcaaggtc tagtggctag cataaagaac tttaagtcag ttctttatta tcaaaacaat gtttttatgt ctgaagcaaa atgttggact gagactgacc ttactaaagg acctcatgaa ttttgctctc aacatacaat gctagttaaa cagggtgatg attatgtgta ccttccttac ccagatccat caagaatcct aggggccggc tgttttgtag atgatatcgt aaaaacagat ggtacactta tgattgaacg gttcgtgtct ttagctatag atgcttaccc acttactaaa catcctaatc aggagtatgc tgatgtcttt catttgtact tacaatacat aagaaagcta catgatgagt taacaggaca catgttagac atgtattctg ttatgcttac taa

Figure 4H

M Protein ORF (MN996531: viral cDNA: 26510-27178) SEQ ID NO:7 a tggcagattc 26521 caacggtact attaccgttg aagagcttaa aaagctcctt gaacaatgga acctagtaat aggtttccta ttccttacat ggatttgtct tctacaattt gcctatgcca acaggaatag gtttttgtat ataattaagt taattttcct ctggctgtta tggccagtaa ctttagcttg ttttgtgctt gctgctgttt acagaataaa ttggatcacc ggtggaattg ctatcgcaat ggcttgtctt gtaggcttga tgtggctcag ctacttcatt gcttctttca gactgtttgc gcgtacgcgt tccatgtggt cattcaatcc agaaactaac attcttctca acgtgccact ccatggcact attctgacca gaccgcttct agaaagtgaa ctcgtaatcg gagctgtgat ccttcgtgga catcttcgta ttgctggaca ccatctagga cgctgtgaca tcaaggacct gcctaaagaa atcactgttg ctacatcacg aacgctttct tattacaaat tgggagcttc gcagcgtgta gcaggtgact caggttttgc tgcatacagt cgctacagga ttggcaacta taaattaaac acagaccatt ccagtagcag tgacaatatt gctttgcttg tacagtaa

Figure 4I

N Protein ORF (MN996531: viral cDNA: 28261-29520) SEQ ID NO:8

28261 atgtctgata atggacccca aaatcagcga aatgcacccc gcattacgtt tggtggaccc tcagattcaa ctggcagtaa ccagaatgga gaacgcagtg gggcgcgatc aaaacaacgt cggccccaag gtttacccaa taatactgcg tcttggttca ccgctctcac tcaacatggc aaggaagacc ttaaattccc tcgaggacaa ggcgttccaa ttaacaccaa tagcagtcca gatgaccaaa ttggctacta ccgaagagct accagacgaa ttcgtggtgg tgacggtaaa atgaaagatc tcagtccaag atggtatttc tactacctag gaactgggcc agaagctgga cttccctatg gtgctaacaa agacggcatc atatgggttg caactgaggg agccttgaat

Figure 4J acaccaaaag atcacattgg cacccgcaat cctgctaaca atgctgcaat cgtgctacaa cttcctcaag
gaacaacatt gccaaaaggc ttctacgcag aagggagcag aggcggcagt caagcctctt ctcgttcctc
atcacgtagt cgcaacagtt caagaaattc aactccaggc agcagtaggg gaacttctcc tgctagaatg
gctggcaatg gcggtgatgc tgctcttgct ttgctgctgc ttgacagatt gaaccagctt gagagcaaaa
tgtctggtaa aggccaacaa caacaaggcc aaactgtcac taagaaatct gctgctgagg cttctaagaa
gcctcggcaa aaacgtactg ccactaaagc atacaatgta acacaagctt tcggcagacg tggtccagaa
caaacccaag gaaattttgg ggaccaggaa ctaatcagac aaggaactga ttacaaacat tggccgcaaa
ttgcacaatt tgcccccagc gcttcagcgt tcttcggaat gtcgcgcatt ggcatggaag tcacaccttc
gggaacgtgg ttgacctaca caggtgccat caaattggat gacaaagatc caaatttcaa agatcaagtc
attttgctga ataagcatat tgacgcatac aaaacattcc caccaacaga gcctaaaaag gacaaaaaga
agaaggctga tgaaactcaa gccttaccgc agagacagaa gaaacagcaa actgtgactc ttcttcctgc
tgcagatttg gatgatttct ccaaacaatt gcaacaatcc atgagcagtg ctgactcaac tcaggcctaa

Figure 4K

E Protein ORF (MN996531: viral cDNA: 26232-26459) SEQ ID NO:9

26232 atgtactca ttcgtttcgg aagagacagg tacgttaata gttaatagcg tacttctttt tcttgctttc gtggtattct
tgctagttac actagccatc cttactgcgc ttcgattgtg tgcgtactgc tgcaatattg ttaacgtgag tcttgtaaaa
ccttcttttt acgtttactc tcgtgttaaa aatctgaatt cttctagagt tcctgatctt ctggtctaa

Figure 5A

D614G Mutated Spike Protein ORF SEQ ID NO:10 atgtttgtttttcttgttttattgccactagtctctagtcagtgtgttaatcttacaaccagaactcaattaccccctgcatacactaat
tctttcacacgtggtgtttattaccctgacaaagttttcagatcctcagttttacattcaactcaggacttgttcttacctttctttcc
aatgttacttggttccatgctatacatgtctctgggaccaatggtactaagaggtttgataaccctgtcctaccatttaatgatgg
tgtttattttgcttccactgagaagtctaacataataagaggctggatttttggtactactttagattcgaagacccagtccctact
tattgttaataacgctactaatgttgttattaaagtctgtgaatttcaattttgtaatgatccatttttgggtgtttattaccacaaaaa
caacaaaagttggatggaaagtgagttcagagtttattctagtgcgaataattgcacttttgaatatgtctctcagccttttcttat
ggaccttgaaggaaaacagggtaatttcaaaaatcttagggaatttgtgtttaagaatattgatggttattttaaaatatattctaa
gcacacgcctattaatttagtgcgtgatctccctcagggtttttcggctttagaaccattggtagatttgccaataggtattaaca
tcactaggtttcaaactttacttgctttacatagaagttatttgactcctggtgattcttcttcaggttggacagctggtgctgcag
cttattatgtgggttatcttcaacctaggacttttctattaaaatataatgaaaatggaaccattacagatgctgtagactgtgcac
ttgaccctctctcagaaacaaagtgtacgttgaaatccttcactgtagaaaaaggaatctatcaaacttctaactttagagtcca
accaacagaatctattgttagatttcctaatattacaaacttgtgcccttttggtgaagtttttaacgccaccagatttgcatctgttt
atgcttggaacaggaagagaatcagcaactgtgttgctgattattctgtcctatataattccgcatcattttccacttttaagtgtt
atggagtgtctcctactaaattaaatgatctctgctttactaatgtctatgcagattcatttgtaattagaggtgatgaagtcagac
aaatcgctccagggcaaactggaaagattgctgattataattataaattaccagatgattttacaggctgcgttatagcttggaa
ttctaacaatcttgattctaaggttggtggtaattataattacctgtatagattgtttaggaagtctaatctcaaaccttttgagaga
gatatttcaactgaaatctatcaggccggtagcacaccttgtaatggtgttgaaggttttaattgttactttcctttacaatcatatg
gtttccaacccactaatggtgttggttaccaaccatacagagtagtagtactttcttttgaacttctacatgcaccagcaactgttt
gtggacctaaaaagtctactaatttggttaaaaacaaatgtgtcaatttcaacttcaatggtttaacaggcacaggtgttcttact
gagtctaacaaaaagtttctgcctttccaacaatttggcagagacattgctgacactactgatgctgtccgtgatccacagaca
cttgagattcttgacattacaccatgttcttttggtggtgtcagtgttataacaccaggaacaaatacttctaaccaggttgctgtt
ctttatcagggtgttaactgcacagaagtccctgttgctattcatgcagatcaacttactcctacttggcgtgtttattctacaggt
tctaatgtttttcaaacacgtgcaggctgtttaataggggctgaacatgtcaacaactcatatgagtgtgacatacccattggtg
caggtatatgcgctagttatcagactcagactaattctcctcggcgggcacgtagtgtagctagtcaatccatcattgcctaca
ctatgtcacttggtgcagaaaattcagttgcttactctaataactctattgccatacccacaaattttactattagtgttaccacag
aaattctaccagtgtctatgaccaagacatcagtagattgtacaatgtacatttgtggtgattcaactgaatgcagcaatcttttg
ttgcaatatggcagtttttgtacacaattaaaccgtgctttaactggaatagctgttgaacaagacaaaaacacccaagaagttt
ttgcacaagtcaaacaaatttacaaaacaccaccaattaaagattttggtggttttaatttttcacaaatattaccagatccatcaa
aaccaagcaagaggtcatttattgaagatctacttttcaacaaagtgacacttgcagatgctggcttcatcaaacaatatggtg
attgccttggtgatattgctgctagagacctcatttgtgcacaaaagtttaacggccttactgttttgccacctttgctcacagat
gaaatgattgctcaatacacttctgcactgttagcgggtacaatcacttctggttggacctttggtgcaggtgctgcattacaaa
taccatttgctatgcaaatggcttataggtttaatggtattggagttacacagaatgttctctatgagaaccaaaaattgattgcc
aaccaatttaatagtgctattggcaaaattcaagactcactttcttccacagcaagtgcacttggaaaacttcaagatgtggtca
accaaaatgcacaagctttaaacacgcttgttaaacaacttagctccaattttggtgcaatttcaagtgttttaaatgatatccttt
cacgtcttgacaaagttgaggctgaagtgcaaattgataggttgatcacaggcagacttcaaagtttgcagacatatgtgact
caacaattaattagagctgcagaaatcagagcttctgctaatcttgctgctactaaaatgtcagagtgtgtacttggacaatca
aaaagagttgatttttgtggaaagggctatcatcttatgtccttccctcagtcagcacctcatggtgtagtcttcttgcatgtgact
tatgtccctgcacaagaaaagaacttcacaactgctcctgccatttgtcatgatggaaaagcacactttcctcgtgaaggtgtc
tttgtttcaaatggcacacactggtttgtaacacaaaggaatttttatgaaccacaaatcattactacagacaacacatttgtgtc

Figure 5B tggtaactgtgatgttgtaataggaattgtcaacaacacagtttatgatcctttgcaacctgaattagactcattcaaggaggag
ttagataaatattttaagaatcatacatcaccagatgttgatttaggtgacatctctggcattaatgcttcagttgtaaacattcaa
aaagaaattgaccgcctcaatgaggttgccaagaatttaaatgaatctctcatcgatctccaagaacttggaaagtatgagca
gtatataaaatggccatggtacatttggctaggttttatagctggcttgattgccatagtaatggtgacaattatgctttgctgtat
gaccagttgctgtagttgtctcaagggctgttgttcttgtggatcctgctgcaaatttgatgaagacgactctgagccagtgctc
aaaggagtcaaattacattacacataa

Figure 5C

D614G Mutated Spike Protein Amino Acid Sequence SEQ ID NO:11

MFVFLVLLPLVSSQCVNLTTRTQLPPAYTNSFTRGVYYPDKVFRSSVLHSTQD
LFLPFFSNVTWFHAIHVSGTNGTKRFDNPVLPFNDGVYFASTEKSNIIRGWIFG
TTLDSKTQSLLIVNNATNVVIKVCEFQFCNDPFLGVYYHKNNKSWMESEFRV
YSSANNCTFEYVSQPFLMDLEGKQGNFKNLREFVFKNIDGYFKIYSKHTPINL
VRDLPQGFSALEPLVDLPIGINITRFQTLLALHRSYLTPGDSSSGWTAGAAAY
YVGYLQPRTFLLKYNENGTITDAVDCALDPLSETKCTLKSFTVEKGIYQTSNF
RVQPTESIVRFPNITNLCPFGEVFNATRFASVYAWNRKRISNCVADYSVLYNS
ASFSTFKCYGVSPTKLNDLCFTNVYADSFVIRGDEVRQIAPGQTGKIADYNYK
LPDDFTGCVIAWNSNNLDSKVGGNYNYLYRLFRKSNLKPFERDISTEIYQAGS
TPCNGVEGFNCYFPLQSYGFQPTNGVGYQPYRVVVLSFELLHAPATVCGPKK
STNLVKNKCVNFNFNGLTGTGVLTESNKKFLPFQQFGRDIADTTDAVRDPQT
LEILDITPCSFGGVSVITPGTNTSNQVAVLYQGVNCTEVPVAIHADQLTPTWR
VYSTGSNVFQTRAGCLIGAEHVNNSYECDIPIGAGICASYQTQTNSPRRARSV
ASQSIIAYTMSLGAENSVAYSNNSIAIPTNFTISVTTEILPVSMTKTSVDCTMYI
CGDSTECSNLLLQYGSFCTQLNRALTGIAVEQDKNTQEVFAQVKQIYKTPPIK
DFGGFNFSQILPDPSKPSKRSFIEDLLFNKVTLADAGFIKQYGDCLGDIAARDLI
CAQKFNGLTVLPPLLTDEMIAQYTSALLAGTITSGWTFGAGAALQIPFAMQM
AYRFNGIGVTQNVLYENQKLIANQFNSAIGKIQDSLSSTASALGKLQDVVNQ
NAQALNTLVKQLSSNFGAISSVLNDILSRLDKVEAEVQIDRLITGRLQSLQTYV
TQQLIRAAEIRASANLAATKMSECVLGQSKRVDFCGKGYHLMSFPQSAPHGV
VFLHVTYVPAQEKNFTTAPAICHDGKAHFPREGVFVSNGTHWFVTQRNFYEP
QIITTDNTFVSGNCDVVIGIVNNTVYDPLQPELDSFKEELDKYFKNHTSPDVDL
GDISGINASVVNIQKEIDRLNEVAKNLNESLIDLQELGKYEQYIKWPWYIWLG
FIAGLIAIVMVTIMLCCMTSCCSCLKGCCSCGSCCKFDEDDSEPVLKGVKLHY
T

Figure 6A

SARS RBD mRNA clone# 2874,
SARS2 Receptor Binding Domain (RBD)-foldon mRNA modified with Cleancap analogue and N1-Methyl-Pseudouridine-5'-Triphosphate. Codon optimized for human SEQ ID No.12
2874

ATTAATACGACTCACTATAAGGAGGCCACCATGTTCGTGTTTCTGGTGCTG
CTGCCTCTGGTGTCCAGCCAGCGGGTGCAGCCCACCGAATCCATCGTGCG
GTTCCCCAATATCACCAATCTGTGCCCCTTCGGCGAGGTGTTCAATGCCAC
CAGATTCGCCTCTGTGTACGCCTGGAACCGGAAGCGGATCAGCAATTGCG
TGGCCGACTACTCCGTGCTGTACAACTCCGCCAGCTTCAGCACCTTCAAGT
GCTACGGCGTGTCCCCTACCAAGCTGAACGACCTGTGCTTCACAAACGTG
TACGCCGACAGCTTCGTGATCCGGGGAGATGAAGTGCGGCAGATTGCCCC
TGGACAGACAGGCAAGATCGCCGACTACAACTACAAGCTGCCCGACGACT
TCACCGGCTGTGTGATTGCCTGGAACAGCAACAACCTGGACTCCAAAGTC
GGCGGCAACTACAATTACCTGTACCGGCTGTTCCGGAAGTCCAATCTGAA
GCCCTTCGAGCGGGACATCTCCACCGAGATCTATCAGGCCGGCAGCACCC
CTTGTAACGGCGTGGAAGGCTTCAACTGCTACTTCCCACTGCAGTCCTACG
GCTTTCAGCCCACAAATGGCGTGGGCTATCAGCCCTACAGAGTGGTGGTG
CTGAGCTTCGAACTGCTGCATGCCCCTGCCACAGTGTGCGGCCCTAAGAA
AAGCACCAATCTCGTGAAGAACAAATGCGTGAACTTCGGATCCGGAGGTG
GATACATCCCGGAGGCCCCTAGGGACGGTCAAGCTTACGTGAGAAAGGA
CGGCGAATGGGTTCTGCTGTCGACCTTCTTGGGATAAGCAAGCTGCTTAC
ATAGAACTCGCGGCGATTGGCATGCCGCCTTAAAATTTTTATTTTATTTTTT
CTTTTCTTTTCCGAATCGGATTTTGTTTTTAATATTTCAAAAAAAAAAAAA
AAAAAAAAAAAACGCGAAAAAAAAAAAAAAAAAAAAAAAAAAAAAAAA
AAAAAAAAAAAAAAAAAATTAATAAAAAAAAAAAAAAAAAAAAAAAAA
AAAAAAAAAAAAAAAAAAAAAAAATTAATAAAAAAAAAAAAAAAAAA
AAAAAAAAAAAAAA AAAAAAAAAAAAAAAAAA

Figure 6B

Protein sequence for D614G Mutated Spike Protein ORF SEQ ID NO:13
MFVFLVLLPLVSSQRVQPTESIVRFPNITNLCPFGEVFNATRFASVYAWNRKRI
SNCVADYSVLYNSASFSTFKCYGVSPTKLNDLCFTNVYADSFVIRGDEVRQIA
PGQTGKIADYNYKLPDDFTGCVIAWNSNNLDSKVGGNYNYLYRLFRKSNLK
PFERDISTEIYQAGSTPCNGVEGFNCYFPLQSYGFQPTNGVGYQPYRVVVLSF
ELLHAPATVCGPKKSTNLVKNKCVNFGSGGGYIPEAPRDGQAYVRKDGEWV
LLST- FLG

Figure 7A

18 polypeptide epitopes for 2019-nCoV spike proteins

| SEQ ID NO | start | stop | peptide |
|---|---|---|---|
| 14 | 576 | 589 | RDIADTTDAVRDPQ |
| 15 | 416 | 429 | VRQIAPGQTGKIAD |
| 16 | 684 | 696 | QTQTNSPRRARSV |
| 17 | 258 | 270 | LTPGDSSSGWTAG |
| 18 | 1146 | 1157 | VYDPLQPELDSF |
| 19 | 814 | 825 | ILPDPSKPSKRS |
| 20 | 504 | 515 | YGFQPTNGVGYQ |
| 21 | 1166 | 1176 | KNHTSPDVDLG |
| 22 | 482 | 492 | YQAGSTPCNGV |
| 23 | 80 | 90 | SGTNGTKRFDN |
| 24 | 30 | 40 | RTQLPPAYTNS |
| 25 | 1265 | 1274 | FDEDDSEPVL |
| 26 | 797 | 806 | IYKTPPIKDF |
| 27 | 606 | 615 | VITPGTNTSN |
| 28 | 532 | 541 | TVCGPKKSTN |
| 29 | 1078 | 1086 | PAQEKNFTT |
| 30 | 781 | 789 | VEQDKNTQE |
| 31 | 448 | 456 | NNLDSKVGG |

Figure 7B

SEQ ID NO:32 - 49

The mRNA sequences corresponding to 18 epitopes of 2019-nCoV spike protein

| SEQ ID NO | start | stop | Nucleotide sequence |
|---|---|---|---|
| 32 | 576 | 589 | AGGGACATCGCCGACACCACCGACGCCGTGAGGGACCCCCAG |
| 33 | 416 | 429 | GTGAGGCAGATCGCCCCCGGCCAGACCGGCAAGATCGCCGAC |
| 34 | 684 | 696 | CAGACCCAGACCAACAGCCCCAGGAGGGCCAGGAGCGTG |
| 35 | 258 | 270 | CTGACCCCCGGCGACAGCAGCAGCGGCTGGACCGCCGGC |
| 36 | 1146 | 1157 | GTGTACGACCCCCTGCAGCCCGAGCTGGACAGCTTC |
| 37 | 814 | 825 | ATCCTGCCCGACCCCAGCAAGCCCAGCAAGAGGAGC |
| 38 | 504 | 515 | TACGGCTTCCAGCCCACCAACGGCGTGGGCTACCAG |
| 39 | 1166 | 1176 | AAGAACCACACCAGCCCCGACGTGGACCTGGGC |
| 40 | 482 | 492 | TACCAGGCCGGCAGCACCCCCTGCAACGGCGTG |

Figure 7C

| | | | |
|---|---|---|---|
| 41 | 80 | 90 | AGCGGCACCAACGGCACCAAGAGGTTCGACAAC |
| 42 | 30 | 40 | AGGACCCAGCTGCCCCCCGCCTACACCAACAGC |
| 43 | 1265 | 1274 | TTCGACGAGGACGACAGCGAGCCCGTGCTG |
| 44 | 797 | 806 | ATCTACAAGACCCCCCCCATCAAGGACTTC |
| 45 | 606 | 615 | GTGATCACCCCCGGCACCAACACCAGCAAC |
| 46 | 532 | 541 | ACCGTGTGCGGCCCCAAGAAGAGCACCAAC |
| 47 | 1078 | 1086 | CCCGCCCAGGAGAAGAACTTCACCACC |
| 48 | 781 | 789 | GTGGAGCAGGACAAGAACACCCAGGAG |
| 49 | 448 | 456 | AACAACCTGGACAGCAAGGTGGGCGGC |

Figure 7D

SEQ ID NO: 50-55

Six unique insertions identified by aligning against other coronavirus recognized by the human immune system

| SEQ ID NO | start | stop | peptide | nucleotide |
|---|---|---|---|---|
| 50 | 153 | 167 | YYHKNNKSWM ESEFR (SEQ ID NO:50) | TACTACCACAAGAACAACAAGAGCTGGATG GAGAGCGAGTTCAGG (SEQ ID NO:108) |
| 51 | 76 | 87 | AIHVSGTNGTK R (SEQ ID NO:51) | GCCATCCACGTGAGCGGCACCAACGGCACC AAGAGG (SEQ ID NO:91) |
| 52 | 252 | 266 | ALHRSYLTPGD SSSG (SEQ ID NO:52) | GCCCTGCACAGGAGCTACCTGACCCCCGGC GACAGCAGCAGCGGC (SEQ ID NO:92) |
| 53 | 447 | 457 | NNLDSKVGGNY (SEQ ID NO:53) | AACAACCTGGACAGCAAGGTGGGCGGCAAC TAC (SEQ ID NO:93) |
| 54 | 479 | 495 | TEIYQAGSTPCN GVEGF(SEQ ID NO:54) | ACCGAGATCTACCAGGCCGGCAGCACCCCC TGCAACGGCGTGGAGGGCTTC (SEQ ID NO:94) |
| 55 | 683 | 692 | QTQTNSPRRA (SEQ ID NO:55) | CAGACCCAGACCAACAGCCCCAGGAGGGCC (SEQ ID NO:95) |

Figure 7E

SEQ ID NO:56 - 66

The RNA sequence coded for various viral peptides serving as potential antigens for vaccination against 2019-nCoV viral infections.

| SEQ ID NO | Start | Stop | Peptide Sequence | Nucleotide Sequence |
|---|---|---|---|---|
| 56 | 606 | 615 | VITPGTNTSN (SEQ ID NO:56) | GUGAUCACCCCCGGCACCAACACCAGCAA C (SEQ ID NO:96) |
| 57 | 532 | 541 | TVCGPKKSTN (SEQ ID NO:57) | ACCGUGUGCGGCCCCAAGAAGAGCACCAA C (SEQ ID NO:97) |

Figure 7F

| | | | | |
|---|---|---|---|---|
| 58 | 1078 | 1086 | PAQEKNFTT (SEQ ID NO:58) | CCCGCCCAGGAGAAGAACUUCACCACC (SEQ ID NO:98) |
| 59 | 781 | 789 | VEQDKNTQE (SEQ ID NO:59) | GUGGAGCAGGACAAGAACACCCAGGAG (SEQ ID NO:99) |
| 60 | 448 | 456 | NNLDSKVGG (SEQ ID NO:60) | AACAACCUGGACAGCAAGGUGGGCGGC (SEQ ID NO:100) |
| 61 | 153 | 167 | YYHKNNKSWM ESEFR(SEQ ID NO:61) | UACUACCACAAGAACAACAAGAGCUGGAU GGAGAGCGAGUUCAGG (SEQ ID NO:101) |
| 62 | 76 | 87 | AIHVSGTNGTK R(SEQ ID NO:62) | GCCAUCCACGUGAGCGGCACCAACGGCAC CAAGAGG (SEQ ID NO:102) |
| 63 | 252 | 266 | ALHRSYLTPGD SSSG (SEQ ID NO:63) | GCCCUGCACAGGAGCUACCUGACCCCCGG CGACAGCAGCAGCGGC (SEQ ID NO:103) |
| 64 | 447 | 457 | NNLDSKVGGNY (SEQ ID NO:64) | AACAACCUGGACAGCAAGGUGGGCGGCAA CUAC (SEQ ID NO:104) |
| 65 | 479 | 495 | TEIYQAGSTPCN GVEGF(SEQ ID NO:65) | ACCGAGAUCUACCAGGCCGGCAGCACCCC CUGCAACGGCGUGGAGGGCUUC (SEQ ID NO:105) |
| 66 | 683 | 692 | QTQTNSPRRA (SEQ ID NO:66) | CAGACCCAGACCAACAGCCCCAGGAGGGC C (SEQ ID NO:106) |

Figure 8A

SEQ ID No. 67

D614G_S6P_DNA_sequence atgtttgtttttcttgttttattgccactagtctctagtcagtgtgttaatcttacaaccagaactcaattaccccctgcatacactaat
tctttcacacgtggtgtttattaccctgacaaagttttcagatcctcagttttacattcaactcaggacttgttcttacctttcttttcc
aatgttacttggttccatgctatacatgtctctgggaccaatggtactaagaggtttgataaccctgtcctaccatttaatgatgg
tgtttattttgcttccactgagaagtctaacataataagaggctggatttttggtactactttagattcgaagacccagtccctact
tattgttaataacgctactaatgttgttattaaagtctgtgaatttcaattttgtaatgatccatttttgggtgtttattaccacaaaaa
caacaaaagttggatggaaagtgagttcagagtttattctagtgcgaataattgcacttttgaatatgtctctcagccttttcttat
ggaccttgaaggaaaacagggtaatttcaaaaatcttagggaatttgtgtttaagaatattgatggttattttaaaatatattctaa
gcacacgcctattaatttagtgcgtgatctccctcagggtttttcggctttagaaccattggtagatttgccaataggtattaaca
tcactaggtttcaaactttacttgctttacatagaagttatttgactcctggtgattcttcttcaggttggacagctggtgctgcag
cttattatgtgggttatcttcaacctaggacttttctattaaaatataatgaaaatggaaccattacagatgctgtagactgtgcac
ttgaccctctctcagaaacaaagtgtacgttgaaatccttcactgtagaaaaaggaatctatcaaacttctaactttagagtcca
accaacagaatctattgttagatttcctaatattacaaacttgtgccctttttggtgaagtttttaacgccaccagatttgcatctgttt
atgcttggaacaggaagagaatcagcaactgtgttgctgattattctgtcctatataattccgcatcattttccacttttaagtgtt
atggagtgtctcctactaaattaaatgatctctgctttactaatgtctatgcagattcatttgtaattagaggtgatgaagtcagac
aaatcgctccagggcaaactggaaagattgctgattataattataaattaccagatgattttacaggctgcgttatagcttggaa
ttctaacaatcttgattctaaggttggtggtaattataattacctgtatagattgtttaggaagtctaatctcaaaccttttgagaga
gatatttcaactgaaatctatcaggccggtagcacaccttgtaatggtgttgaaggttttaattgttactttcctttacaatcatatg
gtttccaacccactaatggtgttggttaccaaccatacagagtagtagtactttcttttgaacttctacatgcaccagcaactgttt
gtggacctaaaaagtctactaatttggttaaaaacaaatgtgtcaatttcaacttcaatggtttaacaggcacaggtgttcttact
gagtctaacaaaaagtttctgcctttccaacaatttggcagagacattgctgacactactgatgctgtccgtgatccacagaca
cttgagattcttgacattacaccatgttcttttggtggtgtcagtgttataacaccaggaacaaatacttctaaccaggttgctgtt
ctttatcagggtgttaactgcacagaagtccctgttgctattcatgcagatcaacttactcctacttggcgtgtttattctacaggt
tctaatgtttttcaaacacgtgcaggctgtttaataggggctgaacatgtcaacaactcatatgagtgtgacatacccattggtg
caggtatatgcgctagttatcagactcagactaattctccttcgcgggcaggtagtgtagctagtcaatccatcattgcctaca
ctatgtcacttggtgcagaaaattcagttgcttactctaataactctattgccatacccacaaattttactattagtgttaccacag
aaattctaccagtgtctatgaccaagacatcagtagattgtacaatgtacatttgtggtgattcaactgaatgcagcaatcttttg
ttgcaatatggcagtttttgtacacaattaaaccgtgctttaactggaatagctgttgaacaagacaaaaacacccaagaagttt
ttgcacaagtcaaacaaatttacaaaacaccaccaattaaagattttggtggttttaatttttcacaaatattaccagatccatcaa
aaccaagcaagaggtcacctattgaagatctacttttcaacaaagtgacacttgcagatgctggcttcatcaaacaatatggt
gattgccttggtgatattgctgctagagacctcatttgtgcacaaaagtttaacggccttactgttttgccacctttgctcacaga
tgaaatgattgctcaatacacttctgcactgttagcgggtacaatcacttctggttggacctttggtgcaggtcctgcattacaa
ataccatttcctatgcaaatggcttataggtttaatggtattggagttacacagaatgttctctatgagaaccaaaaattgattgc
caaccaatttaatagtgctattggcaaaattcaagactcactttcttccacaccaagtgcacttggaaaacttcaagatgtggtc
aaccaaaatgcacaagctttaaacacgcttgttaaacaacttagctccaattttggtgcaatttcaagtgttttaaatgatatcctt
tcacgtcttgacccacctgaggctgaagtgcaaattgataggttgatcacaggcagacttcaaagtttgcagacatatgtgac
tcaacaattaattagagctgcagaaatcagagcttctgctaatcttgctgctactaaaatgtcagagtgtgtacttggacaatca
aaaagagttgattttgtggaaagggctatcatcttatgtccttccctcagtcagcacctcatggtgtagtcttcttgcatgtgact
tatgtccctgcacaagaaaagaacttcacaactgctcctgccatttgtcatgatggaaaagcacactttcctcgtgaaggtgtc
tttgtttcaaatggcacacactggtttgtaacacaaaggaatttttatgaaccacaaatcattactacagacaacacatttgtgtc

Figure 8B tggtaactgtgatgttgtaataggaattgtcaacaacacagtttatgatcctttgcaacctgaattagactcattcaaggaggag
ttagataaatattttaagaatcatacatcaccagatgttgatttaggtgacatctctggcattaatgcttcagttgtaaacattcaa
aaagaaattgaccgcctcaatgaggttgccaagaatttaaatgaatctctcatcgatctccaagaacttggaaagtatgagca
gtatataaaatggccatggtacatttggctaggttttatagctggcttgattgccatagtaatggtgacaattatgctttgctgtat
gaccagttgctgtagttgtctcaagggctgttgttcttgtggatcctgctgcaaatttgatgaagacgactctgagccagtgctc
aaaggagtcaaattacattacacataa

Figure 8C

D614G_S6P_amino_acid_sequence SEQ ID No. 68

MFVFLVLLPLVSSQCVNLTTRTQLPPAYTNSFTRGVYYPDKVFRSSVLHSTQD
LFLPFFSNVTWFHAIHVSGTNGTKRFDNPVLPFNDGVYFASTEKSNIIRGWIFG
TTLDSKTQSLLIVNNATNVVIKVCEFQFCNDPFLGVYYHKNNKSWMESEFRV
YSSANNCTFEYVSQPFLMDLEGKQGNFKNLREFVFKNIDGYFKIYSKHTPINL
VRDLPQGFSALEPLVDLPIGINITRFQTLLALHRSYLTPGDSSSGWTAGAAAY
YVGYLQPRTFLLKYNENGTITDAVDCALDPLSETKCTLKSFTVEKGIYQTSNF
RVQPTESIVRFPNITNLCPFGEVFNATRFASVYAWNRKRISNCVADYSVLYNS
ASFSTFKCYGVSPTKLNDLCFTNVYADSFVIRGDEVRQIAPGQTGKIADYNYK
LPDDFTGCVIAWNSNNLDSKVGGNYNYLYRLFRKSNLKPFERDISTEIYQAGS
TPCNGVEGFNCYFPLQSYGFQPTNGVGYQPYRVVVLSFELLHAPATVCGPKK
STNLVKNKCVNFNFNGLTGTGVLTESNKKFLPFQQFGRDIADTTDAVRDPQT
LEILDITPCSFGGVSVITPGTNTSNQVAVLYQGVNCTEVPVAIHADQLTPTWR
VYSTGSNVFQTRAGCLIGAEHVNNSYECDIPIGAGICASYQTQTNSPSRAGSV
ASQSIIAYTMSLGAENSVAYSNNSIAIPTNFTISVTTEILPVSMTKTSVDCTMYI
CGDSTECSNLLLQYGSFCTQLNRALTGIAVEQDKNTQEVFAQVKQIYKTPPIK
DFGGFNFSQILPDPSKPSKRSPIEDLLFNKVTLADAGFIKQYGDCLGDIAARDLI
CAQKFNGLTVLPPLLTDEMIAQYTSALLAGTITSGWTFGAGPALQIPFPMQMA
YRFNGIGVTQNVLYENQKLIANQFNSAIGKIQDSLSSTPSALGKLQDVVNQNA
QALNTLVKQLSSNFGAISSVLNDILSRLDPPEAEVQIDRLITGRLQSLQTYVTQ
QLIRAAEIRASANLAATKMSECVLGQSKRVDFCGKGYHLMSFPQSAPHGVVF
LHVTYVPAQEKNFTTAPAICHDGKAHFPREGVFVSNGTHWFVTQRNFYEPQII
TTDNTFVSGNCDVVIGIVNNTVYDPLQPELDSFKEELDKYFKNHTSPDVDLG
DISGINASVVNIQKEIDRLNEVAKNLNESLIDLQELGKYEQYIKWPWYIWLGFI
AGLIAIVMVTIMLCCMTSCCSCLKGCCSCGSCCKFDEDDSEPVLKGVKLHYT

Figure 9A

RBD_trimer_DNA_sequence SEQ ID No. 69

Gccaccatgttcgtgtttctggtgctgctgcctctggtgtccagccagcgggtgcagcccaccgaatccatcgtgcggttcc
ccaatatcaccaatctgtgccccttcggcgaggtgttcaatgccaccagattcgcctctgtgtacgcctggaaccggaagcg
gatcagcaattgcgtggccgactactccgtgctgtacaactccgccagcttcagcaccttcaagtgctacggcgtgtcccct
accaagctgaacgacctgtgcttcacaaacgtgtacgccgacagcttcgtgatccggggagatgaagtgcggcagattgc
ccctggacagacaggcaagatcgccgactacaactacaagctgcccgacgacttcaccggctgtgtgattgcctggaaca
gcaacaacctggactccaaagtcggcggcaactacaattacctgtaccggctgttccggaagtccaatctgaagcccttcg
agcgggacatctccaccgagatctatcaggccggcagcaccccttgtaacggcgtggaaggcttcaactgctacttcccac
tgcagtcctacggctttcagcccacaaatggcgtgggctatcagccctacagagtggtggtgctgagcttcgaactgctgca
tgcccctgccacagtgtgcggccctaagaaaagcaccaatctcgtgaagaacaaatgcgtgaacttcggatccggaggtg
gatacatcccggaggcccctagggacggtcaagcttacgtgagaaaggacggcgaatgggttctgctgtcgaccttcttg
ggataa

Figure 9B

RBD_trimer_amino_acid_sequence SEQ ID No. 70

ATMFVFLVLLPLVSSQRVQPTESIVRFPNITNLCPFGEVFNATRFASVYAWNR
KRISNCVADYSVLYNSASFSTFKCYGVSPTKLNDLCFTNVYADSFVIRGDEVR
QIAPGQTGKIADYNYKLPDDFTGCVIAWNSNNLDSKVGGNYNYLYRLFRKS
NLKPFERDISTEIYQAGSTPCNGVEGFNCYFPLQSYGFQPTNGVGYQPYRVVV
LSFELLHAPATVCGPKKSTNLVKNKCVNFGSGGGYIPEAPRDGQAYVRKDGE
WVLLSTFLG

Figure 10A

VUI-202012_01_S6P_DNA_sequence SEQ ID No. 71 atgtttgtttttcttgttttattgccactagtctctagtcagtgtgttaatcttacaaccagaactcaattaccccctgcatacactaat
tctttcacacgtggtgtttattaccctgacaaagttttcagatcctcagttttacattcaactcaggacttgttcttacctttcttttcc
aatgttacttggttccatgctatacatgtctctgggaccaatggtactaagaggtttgataaccctgtcctaccatttaatgatgg
tgtttattttgcttccactgagaagtctaacataataagaggctggatttttggtactactttagattcgaagacccagtccctact
tattgttaataacgctactaatgttgttattaaagtctgtgaatttcaattttgtaatgatccatttttgggtgtttattaccacaaaaa
caacaaaagttggatggaaagtgagttcagagtttattctagtgcgaataattgcacttttgaatatgtctctcagccttttcttat
ggaccttgaaggaaaacagggtaatttcaaaaatcttagggaatttgtgtttaagaatattgatggttattttaaaatatattctaa
gcacacgcctattaatttagtgcgtgatctccctcagggtttttcggctttagaaccattggtagatttgccaataggtattaaca
tcactaggtttcaaactttacttgctttacatagaagttatttgactcctggtgattcttcttcaggttggacagctggtgctgcag
cttattatgtgggttatcttcaacctaggacttttctattaaaatataatgaaaatggaaccattacagatgctgtagactgtgcac
ttgaccctctctcagaaacaaagtgtacgttgaaatccttcactgtagaaaaaggaatctatcaaacttctaactttagagtcca
accaacagaatctattgttagatttcctaatattacaaacttgtgccctttttggtgaagtttttaacgccaccagatttgcatctgttt
atgcttggaacaggaagagaatcagcaactgtgttgctgattattctgtcctatataattccgcatcattttccacttttaagtgtt
atggagtgtctcctactaaattaaatgatctctgctttactaatgtctatgcagattcatttgtaattagaggtgatgaagtcagac
aaatcgctccagggcaaactggaaagattgctgattataattataaattaccagatgattttacaggctgcgttatagcttggaa
ttctaacaatcttgattctaaggttggtggtaattataattacctgtatagattgtttaggaagtctaatctcaaaccttttgagaga
gatatttcaactgaaatctatcaggccggtagcacaccttgtaatggtgttgaaggttttaattgttactttcctttacaatcatatg
gtttccaacccacttatggtgttggttaccaaccatacagagtagtagtactttcttttgaacttctacatgcaccagcaactgttt
gtggacctaaaaagtctactaatttggttaaaaacaaatgtgtcaatttcaacttcaatggtttaacaggcacaggtgttcttact
gagtctaacaaaaagtttctgcctttccaacaatttggcagagacattgatgacactactgatgctgtccgtgatccacagaca
cttgagattcttgacattacaccatgttcttttggtggtgtcagtgttataacaccaggaacaaatacttctaaccaggttgctgtt
ctttatcagggtgttaactgcacagaagtccctgttgctattcatgcagatcaacttactcctacttggcgtgtttattctacaggt
tctaatgtttttcaaacacgtgcaggctgtttaataggggctgaacatgtcaacaactcatatgagtgtgacatacccattggtg
caggtatatgcgctagttatcagactcagactaattctcattcgcgggcaggtagtgtagctagtcaatccatcattgcctaca
ctatgtcacttggtgcagaaaattcagttgcttactctaataactctattgccatacccataaattttactattagtgttaccacaga
aattctaccagtgtctatgaccaagacatcagtagattgtacaatgtacatttgtggtgattcaactgaatgcagcaatcttttgtt
gcaatatggcagtttttgtacacaattaaaccgtgctttaactggaatagctgttgaacaagacaaaaacacccaagaagtttt
gcacaagtcaaacaaatttacaaaacaccaccaattaaagattttggtggttttaatttttcacaaatattaccagatccatcaaa
accaagcaagaggtcacctattgaagatctacttttcaacaaagtgacacttgcagatgctggcttcatcaaacaatatggtg
attgccttggtgatattgctgctagagacctcatttgtgcacaaaagtttaacggccttactgttttgccacctttgctcacagat
gaaatgattgctcaatacacttctgcactgttagcgggtacaatcacttctggttggacctttggtgcaggtcctgcattacaaa
taccatttcctatgcaaatggcttataggtttaatggtattggagttacacagaatgttctctatgagaaccaaaaattgattgcc
aaccaatttaatagtgctattggcaaaattcaagactcactttcttccacaccaagtgcacttggaaaacttcaagatgtggtca
accaaaatgcacaagctttaaacacgcttgttaaacaacttagctccaattttggtgcaatttcaagtgttttaaatgatatccttg
cacgtcttgacccacctgaggctgaagtgcaaattgataggttgatcacaggcagacttcaaagtttgcagacatatgtgact
caacaattaattagagctgcagaaatcagagcttctgctaatcttgctgctactaaaatgtcagagtgtgtacttggacaatca
aaaagagttgatttttgtggaaagggctatcatcttatgtccttccctcagtcagcacctcatggtgtagtcttcttgcatgtgact
tatgtccctgcacaagaaaagaacttcacaactgctcctgccatttgtcatgatggaaaagcacactttcctcgtgaaggtgtc
tttgtttcaaatggcacacactggtttgtaacacaaaggaatttttatgaaccacaaatcattactacacacaacacatttgtgtct

Figure 10B ggtaactgtgatgttgtaataggaattgtcaacaacacagtttatgatcctttgcaacctgaattagactcattcaaggaggagt
tagataaatattttaagaatcatacatcaccagatgttgatttaggtgacatctctggcattaatgcttcagttgtaaacattcaaa
aagaaattgaccgcctcaatgaggttgccaagaatttaaatgaatctctcatcgatctccaagaacttggaaagtatgagcag
tatataaaatggccatggtacatttggctaggttttatagctggcttgattgccatagtaatggtgacaattatgctttgctgtatg
accagttgctgtagttgtctcaagggctgttgttcttgtggatcctgctgcaaatttgatgaagacgactctgagccagtgctca
aaggagtcaaattacattacacataa

Figure 10C

VUI-202012_01_S6P_amino_acid_sequence SEQ ID No. 72

MFVFLVLLPLVSSQCVNLTTRTQLPPAYTNSFTRGVYYPDKVFRSSVLHSTQD
LFLPFFSNVTWFHAIHVSGTNGTKRFDNPVLPFNDGVYFASTEKSNIIRGWIFG
TTLDSKTQSLLIVNNATNVVIKVCEFQFCNDPFLGVYYHKNNKSWMESEFRV
YSSANNCTFEYVSQPFLMDLEGKQGNFKNLREFVFKNIDGYFKIYSKHTPINL
VRDLPQGFSALEPLVDLPIGINITRFQTLLALHRSYLTPGDSSSGWTAGAAAY
YVGYLQPRTFLLKYNENGTITDAVDCALDPLSETKCTLKSFTVEKGIYQTSNF
RVQPTESIVRFPNITNLCPFGEVFNATRFASVYAWNRKRISNCVADYSVLYNS
ASFSTFKCYGVSPTKLNDLCFTNVYADSFVIRGDEVRQIAPGQTGKIADYNYK
LPDDFTGCVIAWNSNNLDSKVGGNYNYLYRLFRKSNLKPFERDISTEIYQAGS
TPCNGVEGFNCYFPLQSYGFQPTYGVGYQPYRVVVLSFELLHAPATVCGPKK
STNLVKNKCVNFNFNGLTGTGVLTESNKKFLPFQQFGRDIDDTTDAVRDPQT
LEILDITPCSFGGVSVITPGTNTSNQVAVLYQGVNCTEVPVAIHADQLTPTWR
VYSTGSNVFQTRAGCLIGAEHVNNSYECDIPIGAGICASYQTQTNSHSRAGSV
ASQSIIAYTMSLGAENSVAYSNNSIAIPINFTISVTTEILPVSMTKTSVDCTMYIC
GDSTECSNLLLQYGSFCTQLNRALTGIAVEQDKNTQEVFAQVKQIYKTPPIKD
FGGFNFSQILPDPSKPSKRSPIEDLLFNKVTLADAGFIKQYGDCLGDIAARDLIC
AQKFNGLTVLPPLLTDEMIAQYTSALLAGTITSGWTFGAGPALQIPFPMQMA
YRFNGIGVTQNVLYENQKLIANQFNSAIGKIQDSLSSTPSALGKLQDVVNQNA
QALNTLVKQLSSNFGAISSVLNDILARLDPPEAEVQIDRLITGRLQSLQTYVTQ
QLIRAAEIRASANLAATKMSECVLGQSKRVDFCGKGYHLMSFPQSAPHGVVF
LHVTYVPAQEKNFTTAPAICHDGKAHFPREGVFVSNGTHWFVTQRNFYEPQII
TTHNTFVSGNCDVVIGIVNNTVYDPLQPELDSFKEELDKYFKNHTSPDVDLG
DISGINASVVNIQKEIDRLNEVAKNLNESLIDLQELGKYEQYIKWPWYIWLGFI
AGLIAIVMVTIMLCCMTSCCSCLKGCCSCGSCCKFDEDDSEPVLKGVKLHYT

Figure 10D

VUI-202012_del_S6P_DNA_sequence SEQ ID No. 73 atgtttgtttttcttgttttattgccactagtctctagtcagtgtgttaatcttacaaccagaactcaattaccccctgcatacactaat
tctttcacacgtggtgtttattaccctgacaaagttttcagatcctcagttttacattcaactcaggacttgttcttacctttcttttcc
aatgttacttggttccatgctatatctgggaccaatggtactaagaggtttgataaccctgtcctaccatttaatgatggtgtttatt
ttgcttccactgagaagtctaacataataagaggctggatttttggtactactttagattcgaagacccagtccctacttattgtta
ataacgctactaatgttgttattaaagtctgtgaatttcaattttgtaatgatccatttttgggtgtttaccacaaaaacaacaaaag
ttggatggaaagtgagttcagagtttattctagtgcgaataattgcactttgaatatgtctctcagccttttcttatggaccttgaa

Figure 10E ggaaaacagggtaatttcaaaaatcttagggaatttgtgtttaagaatattgatggttattttaaaatatattctaagcacacgcct
attaatttagtgcgtgatctccctcagggtttttcggctttagaaccattggtagatttgccaataggtattaacatcactaggtttc
aaactttacttgctttacatagaagttatttgactcctggtgattcttcttcaggttggacagctggtgctgcagcttattatgtggg
ttatcttcaacctaggacttttctattaaaatataatgaaaatggaaccattacagatgctgtagactgtgcacttgaccctctctc
agaaacaaagtgtacgttgaaatccttcactgtagaaaaaggaatctatcaaacttctaactttagagtccaaccaacagaat
ctattgttagatttcctaatattacaaacttgtgccctttggtgaagtttttaacgccaccagatttgcatctgtttatgcttggaac
aggaagagaatcagcaactgtgttgctgattattctgtcctatataattccgcatcattttccactttaagtgttatggagtgtctc
ctactaaattaaatgatctctgctttactaatgtctatgcagattcatttgtaattagaggtgatgaagtcagacaaatcgctcca
gggcaaactggaaagattgctgattataattataaattaccagatgattttacaggctgcgttatagcttggaattctaacaatct
tgattctaaggttggtggtaattataattacctgtatagattgtttaggaagtctaatctcaaacctttgagagagatatttcaact
gaaatctatcaggccggtagcacaccttgtaatggtgttgaaggttttaattgttactttcctttacaatcatatggtttccaaccc
acttatggtgttggttaccaaccatacagagtagtagtactttcttttgaacttctacatgcaccagcaactgtttgtggacctaa
aaagtctactaatttggttaaaaacaaatgtgtcaatttcaacttcaatggtttaacaggcacaggtgttcttactgagtctaaca
aaaagtttctgcctttccaacaatttggcagagacattgatgacactactgatgctgtccgtgatccacagacacttgagattct
tgacattacaccatgttcttttggtggtgtcagtgttataacaccaggaacaaatacttctaaccaggttgctgttctttatcagg
gtgttaactgcacagaagtccctgttgctattcatgcagatcaacttactcctacttggcgtgtttattctacaggttctaatgtttt
caaacacgtgcaggctgtttaataggggctgaacatgtcaacaactcatatgagtgtgacatacccattggtgcaggtatatg
cgctagttatcagactcagactaattctcattcgcgggcaggtagtgtagctagtcaatccatcattgcctacactatgtcactt
ggtgcagaaaattcagttgcttactctaataactctattgccatacccataaatttactattagtgttaccacagaaattctacca
gtgtctatgaccaagacatcagtagattgtacaatgtacatttgtggtgattcaactgaatgcagcaatcttttgttgcaatatgg
cagttttgtacacaattaaaccgtgctttaactggaatagctgttgaacaagacaaaaacacccaagaagtttttgcacaagt
caaacaaatttacaaaacaccaccaattaaagattttggtggttttaatttttcacaaatattaccagatccatcaaaaccaagca
agaggtcacctattgaagatctacttttcaacaaagtgacacttgcagatgctggcttcatcaaacaatatggtgattgccttgg
tgatattgctgctagagacctcatttgtgcacaaaagtttaacggccttactgttttgccacctttgctcacagatgaaatgattg
ctcaatacacttctgcactgttagcgggtacaatcacttctggttggacctttggtgcaggtcctgcattacaaataccatttcct
atgcaaatggcttataggtttaatggtattggagttacacagaatgttctctatgagaaccaaaaattgattgccaaccaatttaa
tagtgctattggcaaaattcaagactcactttcttccacaccaagtgcacttggaaaacttcaagatgtggtcaaccaaaatgc
acaagctttaaacacgcttgttaaacaacttagctccaatttggtgcaatttcaagtgttttaaatgatatccttgcacgtcttga
cccacctgaggctgaagtgcaaattgataggttgatcacaggcagacttcaaagtttgcagacatatgtgactcaacaattaa
ttagagctgcagaaatcagagcttctgctaatcttgctgctactaaaatgtcagagtgtgtacttggacaatcaaaaagagttg
atttttgtggaaagggctatcatcttatgtccttccctcagtcagcacctcatggtgtagtcttcttgcatgtgacttatgtccctgc
acaagaaaagaacttcacaactgctcctgccatttgtcatgatggaaaagcacactttcctcgtgaaggtgtctttgtttcaaat
ggcacacactggtttgtaacacaaaggaattttatgaaccacaaatcattactacacacaacacatttgtgtctggtaactgtg
atgttgtaataggaattgtcaacaacacagtttatgatcctttgcaacctgaattagactcattcaaggaggagttagataaatat
tttaagaatcatacatcaccagatgttgatttaggtgacatctctggcattaatgcttcagttgtaaacattcaaaaagaaattga
ccgcctcaatgaggttgccaagaatttaaatgaatctctcatcgatctccaagaacttggaaagtatgagcagtatataaaatg
gccatggtacatttggctaggttttatagctggcttgattgccatagtaatggtgacaattatgcttttgctgtatgaccagttgctg
tagttgtctcaagggctgttgttcttgtggatcctgctgcaaatttgatgaagacgactctgagccagtgctcaaaggagtcaa
attacattacacataa

Figure 10F

VUI-202012_del_S6P_amino_acid_sequence SEQ ID No. 74

MFVFLVLLPLVSSQCVNLTTRTQLPPAYTNSFTRGVYYPDKVFRSSVLHSTQD
LFLPFFSNVTWFHAISGTNGTKRFDNPVLPFNDGVYFASTEKSNIIRGWIFGTT
LDSKTQSLLIVNNATNVVIKVCEFQFCNDPFLGVYHKNNKSWMESEFRVYSS
ANNCTFEYVSQPFLMDLEGKQGNFKNLREFVFKNIDGYFKIYSKHTPINLVRD
LPQGFSALEPLVDLPIGINITRFQTLLALHRSYLTPGDSSSGWTAGAAAYYVG
YLQPRTFLLKYNENGTITDAVDCALDPLSETKCTLKSFTVEKGIYQTSNFRVQ
PTESIVRFPNITNLCPFGEVFNATRFASVYAWNRKRISNCVADYSVLYNSASFS
TFKCYGVSPTKLNDLCFTNVYADSFVIRGDEVRQIAPGQTGKIADYNYKLPD
DFTGCVIAWNSNNLDSKVGGNYNYLYRLFRKSNLKPFERDISTEIYQAGSTPC
NGVEGFNCYFPLQSYGFQPTYGVGYQPYRVVVLSFELLHAPATVCGPKKSTN
LVKNKCVNFNFNGLTGTGVLTESNKKFLPFQQFGRDIDDTTDAVRDPQTLEIL
DITPCSFGGVSVITPGTNTSNQVAVLYQGVNCTEVPVAIHADQLTPTWRVYST
GSNVFQTRAGCLIGAEHVNNSYECDIPIGAGICASYQTQTNSHSRAGSVASQSI
IAYTMSLGAENSVAYSNNSIAIPINFTISVTTEILPVSMTKTSVDCTMYICGDST
ECSNLLLQYGSFCTQLNRALTGIAVEQDKNTQEVFAQVKQIYKTPPIKDFGGF
NFSQILPDPSKPSKRSPIEDLLFNKVTLADAGFIKQYGDCLGDIAARDLICAQK
FNGLTVLPPLLTDEMIAQYTSALLAGTITSGWTFGAGPALQIPFPMQMAYRFN
GIGVTQNVLYENQKLIANQFNSAIGKIQDSLSSTPSALGKLQDVVNQNAQALN
TLVKQLSSNFGAISSVLNDILARLDPPEAEVQIDRLITGRLQSLQTYVTQQLIRA
AEIRASANLAATKMSECVLGQSKRVDFCGKGYHLMSFPQSAPHGVVFLHVT
YVPAQEKNFTTAPAICHDGKAHFPREGVFVSNGTHWFVTQRNFYEPQIITTHN
TFVSGNCDVVIGIVNNTVYDPLQPELDSFKEELDKYFKNHTSPDVDLGDISGI
NASVVNIQKEIDRLNEVAKNLNESLIDLQELGKYEQYIKWPWYIWLGFIAGLI
AIVMVTIMLCCMTSCCSCLKGCCSCGSCCKFDEDDSEPVLKGVKLHYT

Figure 11

SEQ ID No.75 – 88

| Polymer | Branch Sequence | SEQ ID No. |
|---|---|---|
| - | R= $KH_nKH_nKH_nKH_nK$– | 75 |
| - | R= $H_nKH_nKH_nKH_nKH_nK$– | 76 |
| - | R= $KH_nKH_nKH_nKH_nKH_n$– | 77 |
| - | R= $H_nKH_nKH_nKH_nKH_nKH_n$– | 78 |
| H2K4b | $R_A$= KHKHHKHHKHHKHHKHHKHK– | 79 |
| H3K4b | $R_B$= KHHHKHHHKHHHKHHHK– | 80 |
| H3K(+H)4b | $R_C$= KHHHKHHHKHHHHKHHHK– | 81 |
| H3k(+H)4b | $R_D$= kHHHkHHHkHHHHkHHHk– | 82 |
| H-H3K(+H)4b | $R_E$= HKHHHKHHHKHHHHKHHHK– | 83 |
| HH-H3K(+H)4b | $R_F$= HHKHHHKHHHKHHHHKHHHK– | 84 |
| H4K4b | $R_G$= KHHHHKHHHHKHHHHKHHHHK– | 85 |
| H3K(1+H)4b | $R_H$= KHHHKHHHKHHHKHHHHK– | 86 |
| H3K(3+H)4b | $R_I$= KHHHKHHHHKHHHKHHHK– | 87 |
| H3K(1,3+H)4b | $R_J$= KHHHKHHHHKHHHKHHHHK– | 88 |

Figure 12A

D614G S2P DNA Sequence SEQ ID No.89:

atgtttgtttttcttgttttattgccactagtctctagtcagtgtgttaatcttacaaccagaactcaattaccccctgcatacactaat
tctttcacacgtggtgtttattaccctgacaaagttttcagatcctcagttttacattcaactcaggacttgttcttacctttcttttcc
aatgttacttggttccatgctatacatgtctctgggaccaatggtactaagaggtttgataaccctgtcctaccatttaatgatgg
tgtttattttgcttccactgagaagtctaacataataagaggctggatttttggtactactttagattcgaagacccagtccctact
tattgttaataacgctactaatgttgttattaaagtctgtgaatttcaattttgtaatgatccatttttgggtgtttattaccacaaaaa
caacaaaagttggatggaaagtgagttcagagtttattctagtgcgaataattgcacttttgaatatgtctctcagccttttcttat
ggaccttgaaggaaaacagggtaatttcaaaaatcttagggaatttgtgtttaagaatattgatggttattttaaaatatattctaa
gcacacgcctattaatttagtgcgtgatctccctcagggtttttcggctttagaaccattggtagatttgccaataggtattaaca
tcactaggtttcaaactttacttgctttacatagaagttatttgactcctggtgattcttcttcaggttggacagctggtgctgcag
cttattatgtgggttatcttcaacctaggacttttctattaaaatataatgaaaatggaaccattacagatgctgtagactgtgcac
ttgaccctctctcagaaacaaagtgtacgttgaaatccttcactgtagaaaaaggaatctatcaaacttctaactttagagtcca
accaacagaatctattgttagatttcctaatattacaaacttgtgcccttttggtgaagtttttaacgccaccagatttgcatctgttt
atgcttggaacaggaagagaatcagcaactgtgttgctgattattctgtcctatataattccgcatcattttccacttttaagtgtt
atggagtgtctcctactaaattaaatgatctctgctttactaatgtctatgcagattcatttgtaattagaggtgatgaagtcagac
aaatcgctccagggcaaactggaaagattgctgattataattataaattaccagatgattttacaggctgcgttatagcttggaa
ttctaacaatcttgattctaaggttggtggtaattataattacctgtatagattgtttaggaagtctaatctcaaaccttttgagaga
gatatttcaactgaaatctatcaggccggtagcacaccttgtaatggtgttgaaggttttaattgttactttcctttacaatcatatg
gtttccaacccactaatggtgttggttaccaaccatacagagtagtagtactttcttttgaacttctacatgcaccagcaactgttt
gtggacctaaaaagtctactaatttggttaaaaacaaatgtgtcaatttcaacttcaatggtttaacaggcacaggtgttcttact
gagtctaacaaaaagtttctgcctttccaacaatttggcagagacattgctgacactactgatgctgtccgtgatccacagaca
cttgagattcttgacattacaccatgttcttttggtggtgtcagtgttataacaccaggaacaaatacttctaaccaggttgctgtt
ctttatcagggtgttaactgcacagaagtccctgttgctattcatgcagatcaacttactcctacttggcgtgtttattctacaggt
tctaatgtttttcaaacacgtgcaggctgtttaataggggctgaacatgtcaacaactcatatgagtgtgacatacccattggtg
caggtatatgcgctagttatcagactcagactaattctcctcggcgggcaggtagtgtagctagtcaatccatcattgcctaca
ctatgtcacttggtgcagaaaattcagttgcttactctaataactctattgccatacccacaaattttactattagtgttaccacag
aaattctaccagtgtctatgaccaagacatcagtagattgtacaatgtacatttgtggtgattcaactgaatgcagcaatcttttg
ttgcaatatggcagtttttgtacacaattaaaccgtgctttaactggaatagctgttgaacaagacaaaaacacccaagaagttt
ttgcacaagtcaaacaaatttacaaaacaccaccaattaaagattttggtggttttaatttttcacaaatattaccagatccatcaa
aaccaagcaagaggtcatttattgaagatctacttttcaacaaagtgacacttgcagatgctggcttcatcaaacaatatggtg
attgccttggtgatattgctgctagagacctcatttgtgcacaaaagtttaacggccttactgttttgccacctttgctcacagat
gaaatgattgctcaatacacttctgcactgttagcgggtacaatcacttctggttggacctttggtgcaggtgctgcattacaaa
taccatttgctatgcaaatggcttataggtttaatggtattggagttacacagaatgttctctatgagaaccaaaaattgattgcc
aaccaatttaatagtgctattggcaaaattcaagactcactttcttccacagcaagtgcacttggaaaacttcaagatgtggtca
accaaaatgcacaagctttaaacacgcttgttaaacaacttagctccaattttggtgcaatttcaagtgttttaaatgatatccttt
cacgtcttgacccacctgaggctgaagtgcaaattgataggttgatcacaggcagacttcaaagtttgcagacatatgtgact
caacaattaattagagctgcagaaatcagagcttctgctaatcttgctgctactaaaatgtcagagtgtgtacttggacaatca
aaaagagttgatttttgtggaaagggctatcatcttatgtccttccctcagtcagcacctcatggtgtagtcttcttgcatgtgact
tatgtccctgcacaagaaaagaacttcacaactgctcctgccatttgtcatgatggaaaagcacactttcctcgtgaaggtgtc
tttgtttcaaatggcacacactggtttgtaacacaaaggaattttatgaaccacaaatcattactacagacaacacatttgtgtc
tggtaactgtgatgttgtaataggaattgtcaacaacacagtttatgatcctttgcaacctgaattagactcattcaaggaggag ttagataaatattttaagaatcatacatcaccagatgttgatttaggtgacatctctggcattaatgcttcagttgtaaacattcaa
aaagaaattgaccgcctcaatgaggttgccaagaatttaaatgaatctctcatcgatctccaagaacttggaaagtatgagca
gtatataaaatggccatggtacatttggctaggttttatagctggcttgattgccatagtaatggtgacaattatgctttgctgtat
gaccagttgctgtagttgtctcaagggctgttgttcttgtggatcctgctgcaaatttgatgaagacgactctgagccagtgctc
aaaggagtcaaattacattacacataa

D614G S2P amino acid sequence SEQ ID No.90

MFVFLVLLPLVSSQCVNLTTRTQLPPAYTNSFTRGVYYPDKVFRSSVLHSTQD
LFLPFFSNVTWFHAIHVSGTNGTKRFDNPVLPFNDGVYFASTEKSNIIRGWIFG
TTLDSKTQSLLIVNNATNVVIKVCEFQFCNDPFLGVYYHKNNKSWMESEFRV
YSSANNCTFEYVSQPFLMDLEGKQGNFKNLREFVFKNIDGYFKIYSKHTPINL
VRDLPQGFSALEPLVDLPIGINITRFQTLLALHRSYLTPGDSSSGWTAGAAAY
YVGYLQPRTFLLKYNENGTITDAVDCALDPLSETKCTLKSFTVEKGIYQTSNF
RVQPTESIVRFPNITNLCPFGEVFNATRFASVYAWNRKRISNCVADYSVLYNS
ASFSTFKCYGVSPTKLNDLCFTNVYADSFVIRGDEVRQIAPGQTGKIADYNYK
LPDDFTGCVIAWNSNNLDSKVGGNYNYLYRLFRKSNLKPFERDISTEIYQAGS
TPCNGVEGFNCYFPLQSYGFQPTNGVGYQPYRVVVLSFELLHAPATVCGPKK
STNLVKNKCVNFNFNGLTGTGVLTESNKKFLPFQQFGRDIADTTDAVRDPQT
LEILDITPCSFGGVSVITPGTNTSNQVAVLYQGVNCTEVPVAIHADQLTPTWR
VYSTGSNVFQTRAGCLIGAEHVNNSYECDIPIGAGICASYQTQTNSPSRAGSV
ASQSIIAYTMSLGAENSVAYSNNSIAIPTNFTISVTTEILPVSMTKTSVDCTMYI
CGDSTECSNLLLQYGSFCTQLNRALTGIAVEQDKNTQEVFAQVKQIYKTPPIK
DFGGFNFSQILPDPSKPSKRSFIEDLLFNKVTLADAGFIKQYGDCLGDIAARDLI
CAQKFNGLTVLPPLLTDEMIAQYTSALLAGTITSGWTFGAGAALQIPFAMQM
AYRFNGIGVTQNVLYENQKLIANQFNSAIGKIQDSLSSTASALGKLQDVVNQ
NAQALNTLVKQLSSNFGAISSVLNDILSRLDPPEAEVQIDRLITGRLQSLQTYV
TQQLIRAAEIRASANLAATKMSECVLGQSKRVDFCGKGYHLMSFPQSAPHGV
VFLHVTYVPAQEKNFTTAPAICHDGKAHFPREGVFVSNGTHWFVTQRNFYEP
QIITTDNTFVSGNCDVVIGIVNNTVYDPLQPELDSFKEELDKYFKNHTSPDVDL
GDISGINASVVNIQKEIDRLNEVAKNLNESLIDLQELGKYEQYIKWPWYIWLG
FIAGLIAIVMVTIMLCCMTSCCSCLKGCCSCGSCCKFDEDDSEPVLKGVKLHY
T

Figure 14A

SEQ ID No. 108 and 91 to 95

| SEQ ID NO | start | stop | nucleotide |
|---|---|---|---|
| 108 | 153 | 167 | TACTACCACAAGAACAACAAGAGCTGGATG GAGAGCGAGTTCAGG |
| 91 | 76 | 87 | GCCATCCACGTGAGCGGCACCAACGGCACC AAGAGG |
| 92 | 252 | 266 | GCCCTGCACAGGAGCTACCTGACCCCCGGC GACAGCAGCAGCGGC |
| 93 | 447 | 457 | AACAACCTGGACAGCAAGGTGGGCGGCAAC TAC |
| 94 | 479 | 495 | ACCGAGATCTACCAGGCCGGCAGCACCCCC TGCAACGGCGTGGAGGGCTTC |
| 95 | 683 | 692 | CAGACCCAGACCAACAGCCCCAGGAGGGCC |

Figure 14B SEQ ID No. 96 to 106

| SEQ ID NO | Start | Stop | Nucleotide Sequence |
|---|---|---|---|
| 96 | 606 | 615 | GUGAUCACCCCCGGCACCAACACCAGCAA C |
| 97 | 532 | 541 | ACCGUGUGCGGCCCCAAGAAGAGCACCAA C |
| 98 | 1078 | 1086 | CCCGCCCAGGAGAAGAACUUCACCACC |
| 99 | 781 | 789 | GUGGAGCAGGACAAGAACACCCAGGAG |
| 100 | 448 | 456 | AACAACCUGGACAGCAAGGUGGGCGGC |
| 101 | 153 | 167 | UACUACCACAAGAACAACAAGAGCUGGAU GGAGAGCGAGUUCAGG |
| 102 | 76 | 87 | GCCAUCCACGUGAGCGGCACCAACGGCAC CAAGAGG |
| 103 | 252 | 266 | GCCCUGCACAGGAGCUACCUGACCCCCGG CGACAGCAGCAGCGGC |
| 104 | 447 | 457 | AACAACCUGGACAGCAAGGUGGGCGGCAA CUAC |

| | | | |
|---|---|---|---|
| 105 | 479 | 495 | ACCGAGAUCUACCAGGCCGGCAGCACCCCCUGCAACGGCGUGGAGGGCUUC |
| 106 | 683 | 692 | CAGACCCAGACCAACAGCCCCAGGAGGGCC |

Figure. 14C

SEQUENCE LISTING

```
<160> NUMBER OF SEQ ID NOS: 108

<210> SEQ ID NO 1
<211> LENGTH: 1518
<212> TYPE: DNA
<213> ORGANISM: Severe acute respiratory syndrome coronavirus 2

<400> SEQUENCE: 1

atgttcttgt taacaactaa acgaacaatg tttgtttttc ttgttttatt gccactagtc      60

tctagtcagt gtgttaatct tacaaccaga actcaattac cccctgcata cactaattct     120
```

-continued

```
ttcacacgtg gtgtttatta ccctgacaaa gttttcagat cctcagtttt acattcaact    180

caggacttgt tcttaccttt cttttccaat gttacttggt tccatgctat acatgtctct    240

gggaccaatg gtactaagag gtttgataac cctgtcctac catttaatga tggtgtttat    300

tttgcttcca ctgagaagtc taacataata agaggctgga tttttggtac tactttagat    360

tcgaagaccc agtccctact tattgttaat aacgctacta atgttgttat taaagtctgt    420

gaatttcaat tttgtaatga tccatttttg ggtgtttatt accacaaaaa caacaaaagt    480

tggatggaaa gtgagttcag agtttattct agtgcgaata attgcacttt tgaatatgtc    540

tctcagcctt ttcttatgga ccttgaagga aaacagggta atttcaaaaa tcttagggaa    600

tttgtgttta agaatattga tggttatttt aaaatatatt ctaagcacac gcctattaat    660

ttagtgcgtg atctccctca gggtttttcg gctttagaac cattggtaga tttgccaata    720

ggtattaaca tcactaggtt tcaaacttta cttgctttac atagaagtta tttgactcct    780

ggtgattctt cttcaggttg gacagctggt gctgcagctt attatgtggg ttatcttcaa    840

cctaggactt ttctattaaa atataatgaa aatggaacca ttacagatgc tgtagactgt    900

gcacttgacc ctctctcaga aacaaagtgt acgttgaaat ccttcactgt agaaaaagga    960

atctatcaaa cttctaactt tagagtccaa ccaacagaat ctattgttag atttcctaat   1020

attacaaact tgtgcccttt tggtgaagtt tttaacgcca ccagatttgc atctgtttat   1080

gcttggaaca ggaagagaat cagcaactgt gttgctgatt attctgtcct atataattcc   1140

gcatcatttt ccacttttaa gtgttatgga gtgtctccta ctaaattaaa tgatctctgc   1200

tttactaatg tctatgcaga ttcatttgta attagaggtg atgaagtcag acaaatcgct   1260

ccagggcaaa ctggaaagat tgctgattat aattataaat taccagatga ttttacaggc   1320

tgcgttatag cttggaattc taacaatctt gattctaagg ttggtggtaa ttataattac   1380

ctgtatagat tgtttaggaa gtctaatctc aaaccttttg agagagatat ttcaactgaa   1440

atctatcagg ccggtagcac accttgtaat ggtgttgaag gttttaattg ttactttcct   1500

ttacaatcat atggtttc                                                 1518


<210> SEQ ID NO 2
<211> LENGTH: 700
<212> TYPE: DNA
<213> ORGANISM: Severe acute respiratory syndrome coronavirus 2

<400> SEQUENCE: 2

caacccacta atggtgttgg ttaccaacca tacagagtag tagtactttc ttttgaactt     60

ctacatgcac cagcaactgt ttgtggacct aaaaagtcta ctaatttggt taaaaacaaa    120

tgtgtcaatt tcaacttcaa tggtttaaca ggcacaggtg ttcttactga gtctaacaaa    180

aagtttctgc ctttccaaca atttggcaga gacattgctg acactactga tgctgtccgt    240

gatccacaga cacttgagat tcttgacatt acaccatgtt cttttggtgg tgtcagtgtt    300

ataacaccag gaacaaatac ttctaaccag gttgctgttc tttatcagga tgttaactgc    360

acagaagtcc ctgttgctat tcatgcagat caacttactc ctacttggcg tgtttattct    420

acaggttcta atgtttttca aacacgtgca ggctgtttaa taggggctga acatgtcaac    480

aactcatatg agtgtgacat acccattggt gcaggtatat gcgctagtta tcagactcag    540

actaattctc ctcggcgggc acgtagtgta gctagtcaat ccatcattgc ctacactatg    600

tcacttggtg cagaaaattc agttgcttac tctaataact ctattgccat acccacaaat    660

tttactatta gtgttaccac agaaattcta ccagtgtcta                         700
```

<210> SEQ ID NO 3
<211> LENGTH: 800
<212> TYPE: DNA
<213> ORGANISM: Severe acute respiratory syndrome coronavirus 2

<400> SEQUENCE: 3
tgaccaagac atcagtagat tgtacaatgt acatttgtgg tgattcaact gaatgcagca 60
atcttttgtt gcaatatggc agtttttgta cacaattaaa ccgtgcttta actggaatag 120
ctgttgaaca agacaaaaac acccaagaag tttttgcaca agtcaaacaa atttacaaaa 180
caccaccaat taaagatttt ggtggtttta atttttcaca aatattacca gatccatcaa 240
aaccaagcaa gaggtcattt attgaagatc tacttttcaa caaagtgaca cttgcagatg 300
ctggcttcat caaacaatat ggtgattgcc ttggtgatat tgctgctaga gacctcattt 360
gtgcacaaaa gtttaacggc cttactgttt tgccaccttt gctcacagat gaaatgattg 420
ctcaatacac ttctgcactg ttagcgggta caatcacttc tggttggacc tttggtgcag 480
gtgctgcatt acaaatacca tttgctatgc aaatggctta taggtttaat ggtattggag 540
ttacacagaa tgttctctat gagaaccaaa aattgattgc caaccaattt aatagtgcta 600
ttggcaaaat tcaagactca ctttcttcca cagcaagtgc acttggaaaa cttcaagatg 660
tggtcaacca aaatgcacaa gctttaaaca cgcttgttaa acaacttagc tccaattttg 720
gtgcaatttc aagtgtttta aatgatatcc tttcacgtct tgacaaagtt gaggctgaag 780
tgcaaattga taggttgatc 800

<210> SEQ ID NO 4
<211> LENGTH: 831
<212> TYPE: DNA
<213> ORGANISM: Severe acute respiratory syndrome coronavirus 2

<400> SEQUENCE: 4
acaggcagac ttcaaagttt gcagacatat gtgactcaac aattaattag agctgcagaa 60
atcagagctt ctgctaatct tgctgctact aaaatgtcag agtgtgtact tggacaatca 120
aaaagagttg atttttgtgg aaagggctat catcttatgt ccttccctca gtcagcacct 180
catggtgtag tcttcttgca tgtgacttat gtccctgcac aagaaaagaa cttcacaact 240
gctcctgcca tttgtcatga tggaaaagca cactttcctc gtgaaggtgt ctttgtttca 300
aatggcacac actggtttgt aacacaaagg aatttttatg aaccacaaat cattactaca 360
gacaacacat ttgtgtctgg taactgtgat gttgtaatag gaattgtcaa caacacagtt 420
tatgatcctt tgcaacctga attagactca ttcaaggagg agttagataa atattttaag 480
aatcatacat caccagatgt tgatttaggt gacatctctg gcattaatgc ttcagttgta 540
aacattcaaa aagaaattga ccgcctcaat gaggttgcca agaatttaaa tgaatctctc 600
atcgatctcc aagaacttgg aaagtatgag cagtatataa aatggccatg gtacatttgg 660
ctaggtttta tagctggctt gattgccata gtaatggtga caattatgct ttgctgtatg 720
accagttgct gtagttgtct caagggctgt tgttcttgtg gatcctgctg caaatttgat 780
gaagacgact ctgagccagt gctcaaagga gtcaaattac attacacata a 831

<210> SEQ ID NO 5
<211> LENGTH: 888
<212> TYPE: DNA
<213> ORGANISM: Severe acute respiratory syndrome coronavirus 2

-continued

<400> SEQUENCE: 5

```
gccacgtata aaccaaatac ctggtgtata cgttgtcttt ggagcacaaa accagttgaa     60
acatcaaatt cgtttgatgt actgaagtca gaggacgcgc agggaatgga taatcttgcc    120
tgcgaagatc taaaaccagt ctctgaagaa gtagtggaaa atcctaccat acagaaagac    180
gttcttgagt gtaatgtgaa aactaccgaa gttgtaggag acattatact taaaccagca    240
aataatagtt taaaaattac agaagaggtt ggccacacag atctaatggc tgcttatgta    300
gacaattcta gtcttactat taagaaacct aatgaattat ctagagtatt aggtttgaaa    360
acccttgcta ctcatggttt agctgctgtt aatagtgtcc cttgggatac tatagctaat    420
tatgctaagc cttttcttaa caaagttgtt agtacaacta ctaacatagt tacacggtgt    480
ttaaaccgtg tttgtactaa ttatatgcct tatttcttta ctttattgct acaattgtgt    540
acttttacta gaagtacaaa ttctagaatt aaagcatcta tgccgactac tatagcaaag    600
aatactgtta agagtgtcgg taaattttgt ctagaggctt catttaatta tttgaagtca    660
cctaattttt ctaaactgat aaatattata atttggtttt tactattaag tgtttgccta    720
ggttctttaa tctactcaac cgctgcttta ggtgttttaa tgtctaattt aggcatgcct    780
tcttactgta ctggttacag agaaggctat ttgaactcta ctaatgtcac tattgcaacc    840
tactgtactg gttctatacc ttgtagtgtt tgtcttagtg gtttagat                888
```

<210> SEQ ID NO 6
<211> LENGTH: 901
<212> TYPE: DNA
<213> ORGANISM: Severe acute respiratory syndrome coronavirus 2

<400> SEQUENCE: 6

```
tagaaaaccc tcaccttatg ggttgggatt atcctaaatg tgatagagcc atgcctaaca     60
tgcttagaat tatggcctca cttgttcttg ctcgcaaaca tacaacgtgt tgtagcttgt    120
cacaccgttt ctatagatta gctaatgagt gtgctcaagt attgagtgaa atggtcatgt    180
gtggcggttc actatatgtt aaaccaggtg gaacctcatc aggagatgcc acaactgctt    240
atgctaatag tgtttttaac atttgtcaag ctgtcacggc caatgttaat gcacttttat    300
ctactgatgg taacaaaatt gccgataagt atgtccgcaa tttacaacac agactttatg    360
agtgtctcta tagaaataga gatgttgaca cagactttgt gaatgagttt tacgcatatt    420
tgcgtaaaca tttctcaatg atgatactct ctgacgatgc tgttgtgtgt ttcaatagca    480
cttatgcatc tcaaggtcta gtggctagca taaagaactt taagtcagtt ctttattatc    540
aaaacaatgt ttttatgtct gaagcaaaat gttggactga gactgacctt actaaaggac    600
ctcatgaatt ttgctctcaa catacaatgc tagttaaaca gggtgatgat tatgtgtacc    660
ttccttaccc agatccatca agaatcctag gggccggctg ttttgtagat gatatcgtaa    720
aaacagatgg tacacttatg attgaacggt tcgtgtcttt agctatagat gcttacccac    780
ttactaaaca tcctaatcag gagtatgctg atgtctttca tttgtactta caatacataa    840
gaaagctaca tgatgagtta acaggacaca tgttagacat gtattctgtt atgcttacta    900
a                                                                    901
```

<210> SEQ ID NO 7
<211> LENGTH: 669
<212> TYPE: DNA
<213> ORGANISM: Severe acute respiratory syndrome coronavirus 2

<400> SEQUENCE: 7
atggcagatt ccaacggtac tattaccgtt gaagagctta aaaagctcct tgaacaatgg 60
aacctagtaa taggtttcct attccttaca tggatttgtc ttctacaatt tgcctatgcc 120
aacaggaata ggtttttgta tataattaag ttaattttcc tctggctgtt atggccagta 180
actttagctt gttttgtgct tgctgctgtt tacagaataa attggatcac cggtggaatt 240
gctatcgcaa tggcttgtct tgtaggcttg atgtggctca gctacttcat tgcttctttc 300
agactgtttg cgcgtacgcg ttccatgtgg tcattcaatc cagaaactaa cattcttctc 360
aacgtgccac tccatggcac tattctgacc agaccgcttc tagaaagtga actcgtaatc 420
ggagctgtga tccttcgtgg acatcttcgt attgctggac accatctagg acgctgtgac 480
atcaaggacc tgcctaaaga aatcactgtt gctacatcac gaacgctttc ttattacaaa 540
ttgggagctt cgcagcgtgt agcaggtgac tcaggttttg ctgcatacag tcgctacagg 600
attggcaact ataaattaaa cacagaccat tccagtagca gtgacaatat tgctttgctt 660
gtacagtaa 669

<210> SEQ ID NO 8
<211> LENGTH: 1260
<212> TYPE: DNA
<213> ORGANISM: Severe acute respiratory syndrome coronavirus 2

<400> SEQUENCE: 8
atgtctgata atggacccca aaatcagcga aatgcacccc gcattacgtt tggtggaccc 60
tcagattcaa ctggcagtaa ccagaatgga gaacgcagtg gggcgcgatc aaaacaacgt 120
cggccccaag gtttacccaa taatactgcg tcttggttca ccgctctcac tcaacatggc 180
aaggaagacc ttaaattccc tcgaggacaa ggcgttccaa ttaacaccaa tagcagtcca 240
gatgaccaaa ttggctacta ccgaagagct accagacgaa ttcgtggtgg tgacggtaaa 300
atgaaagatc tcagtccaag atggtatttc tactacctag gaactgggcc agaagctgga 360
cttccctatg gtgctaacaa agacggcatc atatgggttg caactgaggg agccttgaat 420
acaccaaaag atcacattgg cacccgcaat cctgctaaca atgctgcaat cgtgctacaa 480
cttcctcaag gaacaacatt gccaaaaggc ttctacgcag aagggagcag aggcggcagt 540
caagcctctt ctcgttcctc atcacgtagt cgcaacagtt caagaaattc aactccaggc 600
agcagtaggg gaacttctcc tgctagaatg gctggcaatg gcggtgatgc tgctcttgct 660
ttgctgctgc ttgacagatt gaaccagctt gagagcaaaa tgtctggtaa aggccaacaa 720
caacaaggcc aaactgtcac taagaaatct gctgctgagg cttctaagaa gcctcggcaa 780
aaacgtactg ccactaaagc atacaatgta acacaagctt tcggcagacg tggtccagaa 840
caaacccaag gaaattttgg ggaccaggaa ctaatcagac aaggaactga ttacaaacat 900
tggccgcaaa ttgcacaatt tgcccccagc gcttcagcgt tcttcggaat gtcgcgcatt 960
ggcatggaag tcacaccttc gggaacgtgg ttgacctaca caggtgccat caaattggat 1020
gacaaagatc caaatttcaa agatcaagtc attttgctga ataagcatat tgacgcatac 1080
aaaacattcc caccaacaga gcctaaaaag gacaaaaaga agaaggctga tgaaactcaa 1140
gccttaccgc agagacagaa gaaacagcaa actgtgactc ttcttcctgc tgcagatttg 1200
gatgatttct ccaaacaatt gcaacaatcc atgagcagtg ctgactcaac tcaggcctaa 1260

<210> SEQ ID NO 9

```
<211> LENGTH: 228
<212> TYPE: DNA
<213> ORGANISM: Severe acute respiratory syndrome coronavirus 2

<400> SEQUENCE: 9

atgtactcat tcgtttcgga agagacaggt acgttaatag ttaatagcgt acttcttttt     60

cttgctttcg tggtattctt gctagttaca ctagccatcc ttactgcgct tcgattgtgt    120

gcgtactgct gcaatattgt taacgtgagt cttgtaaaac cttcttttta cgtttactct    180

cgtgttaaaa atctgaattc ttctagagtt cctgatcttc tggtctaa                228


<210> SEQ ID NO 10
<211> LENGTH: 3822
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

atgtttgttt ttcttgtttt attgccacta gtctctagtc agtgtgttaa tcttacaacc     60

agaactcaat tacccccctgc atacactaat tctttcacac gtggtgttta ttaccctgac    120

aaagttttca gatcctcagt tttacattca actcaggact tgttcttacc tttcttttcc    180

aatgttactt ggttccatgc tatacatgtc tctgggacca atggtactaa gaggtttgat    240

aaccctgtcc taccatttaa tgatggtgtt tattttgctt ccactgagaa gtctaacata    300

ataagaggct ggatttttgg tactacttta gattcgaaga cccagtccct acttattgtt    360

aataacgcta ctaatgttgt tattaaagtc tgtgaatttc aattttgtaa tgatccattt    420

ttgggtgttt attaccacaa aaacaacaaa agttggatgg aaagtgagtt cagagtttat    480

tctagtgcga ataattgcac ttttgaatat gtctctcagc cttttcttat ggaccttgaa    540

ggaaaacagg gtaatttcaa aaatcttagg gaatttgtgt ttaagaatat tgatggttat    600

tttaaaatat attctaagca cacgcctatt aatttagtgc gtgatctccc tcagggtttt    660

tcggctttag aaccattggt agatttgcca ataggtatta acatcactag gtttcaaact    720

ttacttgctt tacatagaag ttatttgact cctggtgatt cttcttcagg ttggacagct    780

ggtgctgcag cttattatgt gggttatctt caacctagga cttttctatt aaaatataat    840

gaaaatggaa ccattacaga tgctgtagac tgtgcacttg accctctctc agaaacaaag    900

tgtacgttga aatccttcac tgtagaaaaa ggaatctatc aaacttctaa ctttagagtc    960

caaccaacag aatctattgt tagatttcct aatattacaa acttgtgccc ttttggtgaa   1020

gtttttaacg ccaccagatt tgcatctgtt tatgcttgga acaggaagag aatcagcaac   1080

tgtgttgctg attattctgt cctatataat tccgcatcat tttccacttt taagtgttat   1140

ggagtgtctc ctactaaatt aaatgatctc tgctttacta atgtctatgc agattcattt   1200

gtaattagag gtgatgaagt cagacaaatc gctccagggc aaactggaaa gattgctgat   1260

tataattata aattaccaga tgattttaca ggctgcgtta tagcttggaa ttctaacaat   1320

cttgattcta aggttggtgg taattataat tacctgtata gattgtttag gaagtctaat   1380

ctcaaacctt ttgagagaga tatttcaact gaaatctatc aggccggtag cacaccttgt   1440

aatggtgttg aaggttttaa ttgttacttt cctttacaat catatggttt ccaacccact   1500

aatggtgttg gttaccaacc atacagagta gtagtacttt cttttgaact tctacatgca   1560

ccagcaactg tttgtggacc taaaaagtct actaatttgg ttaaaaacaa atgtgtcaat   1620
```

-continued

```
ttcaacttca atggtttaac aggcacaggt gttcttactg agtctaacaa aaagtttctg   1680

cctttccaac aatttggcag agacattgct gacactactg atgctgtccg tgatccacag   1740

acacttgaga ttcttgacat tacaccatgt tcttttggtg gtgtcagtgt tataacacca   1800

ggaacaaata cttctaacca ggttgctgtt ctttatcagg gtgttaactg cacagaagtc   1860

cctgttgcta ttcatgcaga tcaacttact cctacttggc gtgtttattc tacaggttct   1920

aatgtttttc aaacacgtgc aggctgttta atagggggctg aacatgtcaa caactcatat   1980

gagtgtgaca tacccattgg tgcaggtata tgcgctagtt atcagactca gactaattct   2040

cctcggcggg cacgtagtgt agctagtcaa tccatcattg cctacactat gtcacttggt   2100

gcagaaaatt cagttgctta ctctaataac tctattgcca tacccacaaa ttttactatt   2160

agtgttacca cagaaattct accagtgtct atgaccaaga catcagtaga ttgtacaatg   2220

tacatttgtg gtgattcaac tgaatgcagc aatcttttgt tgcaatatgg cagtttttgt   2280

acacaattaa accgtgcttt aactggaata gctgttgaac aagacaaaaa cacccaagaa   2340

gtttttgcac aagtcaaaca aatttacaaa acaccaccaa ttaaagattt tggtggtttt   2400

aatttttcac aaatattacc agatccatca aaaccaagca agaggtcatt tattgaagat   2460

ctacttttca acaaagtgac acttgcagat gctggcttca tcaaacaata tggtgattgc   2520

cttggtgata ttgctgctag agacctcatt tgtgcacaaa agtttaacgg ccttactgtt   2580

ttgccacctt tgctcacaga tgaaatgatt gctcaataca cttctgcact gttagcgggt   2640

acaatcactt ctggttggac ctttggtgca ggtgctgcat tacaaatacc atttgctatg   2700

caaatggctt ataggtttaa tggtattgga gttacacaga atgttctcta tgagaaccaa   2760

aaattgattg ccaaccaatt taatagtgct attggcaaaa ttcaagactc actttcttcc   2820

acagcaagtg cacttggaaa acttcaagat gtggtcaacc aaaatgcaca agctttaaac   2880

acgcttgtta aacaacttag ctccaatttt ggtgcaattt caagtgtttt aaatgatatc   2940

ctttcacgtc ttgacaaagt tgaggctgaa gtgcaaattg ataggttgat cacaggcaga   3000

cttcaaagtt tgcagacata tgtgactcaa caattaatta gagctgcaga aatcagagct   3060

tctgctaatc ttgctgctac taaaatgtca gagtgtgtac ttggacaatc aaaaagagtt   3120

gatttttgtg gaaagggcta tcatcttatg tccttccctc agtcagcacc tcatggtgta   3180

gtcttcttgc atgtgactta tgtccctgca caagaaaaga acttcacaac tgctcctgcc   3240

atttgtcatg atggaaaagc acactttcct cgtgaaggtg tctttgtttc aaatggcaca   3300

cactggtttg taacacaaag gaatttttat gaaccacaaa tcattactac agacaacaca   3360

tttgtgtctg gtaactgtga tgttgtaata ggaattgtca acaacacagt ttatgatcct   3420

ttgcaacctg aattagactc attcaaggag gagttagata aatattttaa gaatcataca   3480

tcaccagatg ttgatttagg tgacatctct ggcattaatg cttcagttgt aaacattcaa   3540

aaagaaattg accgcctcaa tgaggttgcc aagaatttaa atgaatctct catcgatctc   3600

caagaacttg gaaagtatga gcagtatata aaatggccat ggtacatttg gctaggtttt   3660

atagctggct tgattgccat agtaatggtg acaattatgc tttgctgtat gaccagttgc   3720

tgtagttgtc tcaagggctg ttgttcttgt ggatcctgct gcaaatttga tgaagacgac   3780

tctgagccag tgctcaaagg agtcaaatta cattacacat aa                      3822
```

<210> SEQ ID NO 11
<211> LENGTH: 1273
<212> TYPE: PRT
<213> ORGANISM: Artificial Sequence -continued
<220> FEATURE:
<223> OTHER INFORMATION: Description of Artificial Sequence: Synthetic
      polypeptide

<400> SEQUENCE: 11

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380
```

-continued

```
Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Gly Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800
```

-continued

```
Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200
```

```
Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270
```

<210> SEQ ID NO 12
<211> LENGTH: 1132
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
attaatacga ctcactataa ggaggccacc atgttcgtgt ttctggtgct gctgcctctg     60

gtgtccagcc agcgggtgca gcccaccgaa tccatcgtgc ggttccccaa tatcaccaat    120

ctgtgcccct tcggcgaggt gttcaatgcc accagattcg cctctgtgta cgcctggaac    180

cggaagcgga tcagcaattg cgtggccgac tactccgtgc tgtacaactc cgccagcttc    240

agcaccttca agtgctacgg cgtgtcccct accaagctga acgacctgtg cttcacaaac    300

gtgtacgccg acagcttcgt gatccgggga gatgaagtgc ggcagattgc ccctggacag    360

acaggcaaga tcgccgacta caactacaag ctgcccgacg acttcaccgg ctgtgtgatt    420

gcctggaaca gcaacaacct ggactccaaa gtcggcggca actacaatta cctgtaccgg    480

ctgttccgga agtccaatct gaagcccttc gagcgggaca tctccaccga gatctatcag    540

gccggcagca ccccttgtaa cggcgtggaa ggcttcaact gctacttccc actgcagtcc    600

tacggctttc agcccacaaa tggcgtgggc tatcagccct acagagtggt ggtgctgagc    660

ttcgaactgc tgcatgcccc tgccacagtg tgcggcccta agaaaagcac caatctcgtg    720

aagaacaaat gcgtgaactt cggatccgga ggtggataca tcccggaggc ccctagggac    780

ggtcaagctt acgtgagaaa ggacggcgaa tgggttctgc tgtcgacctt cttgggataa    840

gcaagctgct tacatagaac tcgcggcgat tggcatgccg ccttaaaatt tttattttat    900

tttttctttt cttttccgaa tcggattttg tttttaatat ttcaaaaaaa aaaaaaaaaa    960

aaaaaaaacg cgaaaaaaaa aaaaaaaaaa aaaaaaaaaa aaaaaaaaaa aaaaaaaaaa   1020

aattaataaa aaaaaaaaaa aaaaaaaaaa aaaaaaaaaa aaaaaaaaaa aaaaaaaatta   1080

ataaaaaaaa aaaaaaaaaa aaaaaaaaaa aaaaaaaaaa aaaaaaaaaa aa           1132
```

<210> SEQ ID NO 13
<211> LENGTH: 269
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Met Phe Val Phe Leu Val Leu Leu Pro Leu Val Ser Ser Gln Arg Val
1               5                   10                  15
```

Gln Pro Thr Glu Ser Ile Val Arg Phe Pro Asn Ile Thr Asn Leu Cys
20 25 30

Pro Phe Gly Glu Val Phe Asn Ala Thr Arg Phe Ala Ser Val Tyr Ala
35 40 45

Trp Asn Arg Lys Arg Ile Ser Asn Cys Val Ala Asp Tyr Ser Val Leu
50 55 60

Tyr Asn Ser Ala Ser Phe Ser Thr Phe Lys Cys Tyr Gly Val Ser Pro
65 70 75 80

Thr Lys Leu Asn Asp Leu Cys Phe Thr Asn Val Tyr Ala Asp Ser Phe
85 90 95

Val Ile Arg Gly Asp Glu Val Arg Gln Ile Ala Pro Gly Gln Thr Gly
100 105 110

Lys Ile Ala Asp Tyr Asn Tyr Lys Leu Pro Asp Asp Phe Thr Gly Cys
115 120 125

Val Ile Ala Trp Asn Ser Asn Asn Leu Asp Ser Lys Val Gly Gly Asn
130 135 140

Tyr Asn Tyr Leu Tyr Arg Leu Phe Arg Lys Ser Asn Leu Lys Pro Phe
145 150 155 160

Glu Arg Asp Ile Ser Thr Glu Ile Tyr Gln Ala Gly Ser Thr Pro Cys
165 170 175

Asn Gly Val Glu Gly Phe Asn Cys Tyr Phe Pro Leu Gln Ser Tyr Gly
180 185 190

Phe Gln Pro Thr Asn Gly Val Gly Tyr Gln Pro Tyr Arg Val Val Val
195 200 205

Leu Ser Phe Glu Leu Leu His Ala Pro Ala Thr Val Cys Gly Pro Lys
210 215 220

Lys Ser Thr Asn Leu Val Lys Asn Lys Cys Val Asn Phe Gly Ser Gly
225 230 235 240

Gly Gly Tyr Ile Pro Glu Ala Pro Arg Asp Gly Gln Ala Tyr Val Arg
245 250 255

Lys Asp Gly Glu Trp Val Leu Leu Ser Thr Phe Leu Gly
260 265

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Arg Asp Ile Ala Asp Thr Thr Asp Ala Val Arg Asp Pro Gln
1 5 10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Val Arg Gln Ile Ala Pro Gly Gln Thr Gly Lys Ile Ala Asp
1 5 10

<210> SEQ ID NO 16
<211> LENGTH: 13

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Gln Thr Gln Thr Asn Ser Pro Arg Arg Ala Arg Ser Val
1 5 10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Leu Thr Pro Gly Asp Ser Ser Ser Gly Trp Thr Ala Gly
1 5 10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Val Tyr Asp Pro Leu Gln Pro Glu Leu Asp Ser Phe
1 5 10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Ile Leu Pro Asp Pro Ser Lys Pro Ser Lys Arg Ser
1 5 10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Tyr Gly Phe Gln Pro Thr Asn Gly Val Gly Tyr Gln
1 5 10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Lys Asn His Thr Ser Pro Asp Val Asp Leu Gly
1 5 10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Tyr Gln Ala Gly Ser Thr Pro Cys Asn Gly Val
1 5 10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Ser Gly Thr Asn Gly Thr Lys Arg Phe Asp Asn
1 5 10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Arg Thr Gln Leu Pro Pro Ala Tyr Thr Asn Ser
1 5 10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Phe Asp Glu Asp Asp Ser Glu Pro Val Leu
1 5 10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Ile Tyr Lys Thr Pro Pro Ile Lys Asp Phe
1 5 10

<210> SEQ ID NO 27
<211> LENGTH: 10

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Val Ile Thr Pro Gly Thr Asn Thr Ser Asn
1 5 10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Thr Val Cys Gly Pro Lys Lys Ser Thr Asn
1 5 10

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Pro Ala Gln Glu Lys Asn Phe Thr Thr
1 5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Val Glu Gln Asp Lys Asn Thr Gln Glu
1 5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Asn Asn Leu Asp Ser Lys Val Gly Gly
1 5

<210> SEQ ID NO 32
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
agggacatcg ccgacaccac cgacgccgtg agggaccccc ag 42

<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
gtgaggcaga tcgcccccgg ccagaccggc aagatcgccg ac 42

<210> SEQ ID NO 34
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
cagacccaga ccaacagccc caggagggcc aggagcgtg 39

<210> SEQ ID NO 35
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
ctgacccccg gcgacagcag cagcggctgg accgccggc 39

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
gtgtacgacc ccctgcagcc cgagctggac agcttc 36

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
atcctgcccg accccagcaa gcccagcaag aggagc 36

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
tacggcttcc agcccaccaa cggcgtgggc taccag 36

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
aagaaccaca ccagccccga cgtggacctg ggc 33

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
taccaggccg gcagcacccc ctgcaacggc gtg 33

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
agcggcacca acggcaccaa gaggttcgac aac 33

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
aggacccagc tgccccccgc ctacaccaac agc 33

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
ttcgacgagg acgacagcga gcccgtgctg 30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
atctacaaga cccccccat caaggacttc 30

-continued

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
gtgatcaccc ccggcaccaa caccagcaac 30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
accgtgtgcg gccccaagaa gagcaccaac 30

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
cccgcccagg agaagaactt caccacc 27

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
gtggagcagg acaagaacac ccaggag 27

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
aacaacctgg acagcaaggt gggcggc 27

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Tyr Tyr His Lys Asn Asn Lys Ser Trp Met Glu Ser Glu Phe Arg
1 5 10 15

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Ala Ile His Val Ser Gly Thr Asn Gly Thr Lys Arg
1 5 10

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Ala Leu His Arg Ser Tyr Leu Thr Pro Gly Asp Ser Ser Ser Gly
1 5 10 15

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Asn Asn Leu Asp Ser Lys Val Gly Gly Asn Tyr
1 5 10

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Thr Glu Ile Tyr Gln Ala Gly Ser Thr Pro Cys Asn Gly Val Glu Gly
1 5 10 15

Phe

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Gln Thr Gln Thr Asn Ser Pro Arg Arg Ala
1 5 10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Val Ile Thr Pro Gly Thr Asn Thr Ser Asn
1 5 10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Thr Val Cys Gly Pro Lys Lys Ser Thr Asn
1 5 10

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Pro Ala Gln Glu Lys Asn Phe Thr Thr
1 5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Val Glu Gln Asp Lys Asn Thr Gln Glu
1 5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Asn Asn Leu Asp Ser Lys Val Gly Gly
1 5

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Tyr Tyr His Lys Asn Asn Lys Ser Trp Met Glu Ser Glu Phe Arg
1 5 10 15

<210> SEQ ID NO 62
<211> LENGTH: 12

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Ile His Val Ser Gly Thr Asn Gly Thr Lys Arg
1               5                   10

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Leu His Arg Ser Tyr Leu Thr Pro Gly Asp Ser Ser Ser Gly
1               5                   10                  15

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asn Asn Leu Asp Ser Lys Val Gly Gly Asn Tyr
1               5                   10

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Glu Ile Tyr Gln Ala Gly Ser Thr Pro Cys Asn Gly Val Glu Gly
1               5                   10                  15

Phe

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Thr Gln Thr Asn Ser Pro Arg Arg Ala
1               5                   10

<210> SEQ ID NO 67
<211> LENGTH: 3822
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
atgtttgttt ttcttgtttt attgccacta gtctctagtc agtgtgttaa tcttacaacc 60
agaactcaat taccccctgc atacactaat tctttcacac gtggtgttta ttaccctgac 120
aaagttttca gatcctcagt tttacattca actcaggact tgttcttacc tttcttttcc 180
aatgttactt ggttccatgc tatacatgtc tctgggacca atggtactaa gaggtttgat 240
aaccctgtcc taccatttaa tgatggtgtt tattttgctt ccactgagaa gtctaacata 300
ataagaggct ggatttttgg tactacttta gattcgaaga cccagtccct acttattgtt 360
aataacgcta ctaatgttgt tattaaagtc tgtgaatttc aattttgtaa tgatccattt 420
ttgggtgttt attaccacaa aaacaacaaa agttggatgg aaagtgagtt cagagtttat 480
tctagtgcga ataattgcac ttttgaatat gtctctcagc cttttcttat ggaccttgaa 540
ggaaaacagg gtaatttcaa aaatcttagg gaatttgtgt ttaagaatat tgatggttat 600
tttaaaatat attctaagca cacgcctatt aatttagtgc gtgatctccc tcagggtttt 660
tcggctttag aaccattggt agatttgcca ataggtatta acatcactag gtttcaaact 720
ttacttgctt tacatagaag ttatttgact cctggtgatt cttcttcagg ttggacagct 780
ggtgctgcag cttattatgt gggttatctt caacctagga cttttctatt aaaatataat 840
gaaaatggaa ccattacaga tgctgtagac tgtgcacttg accctctctc agaaacaaag 900
tgtacgttga aatccttcac tgtagaaaaa ggaatctatc aaacttctaa ctttagagtc 960
caaccaacag aatctattgt tagatttcct aatattacaa acttgtgccc ttttggtgaa 1020
gtttttaacg ccaccagatt tgcatctgtt tatgcttgga acaggaagag aatcagcaac 1080
tgtgttgctg attattctgt cctatataat tccgcatcat tttccacttt taagtgttat 1140
ggagtgtctc ctactaaatt aaatgatctc tgctttacta atgtctatgc agattcattt 1200
gtaattagag gtgatgaagt cagacaaatc gctccagggc aaactggaaa gattgctgat 1260
tataattata aattaccaga tgattttaca ggctgcgtta tagcttggaa ttctaacaat 1320
cttgattcta aggttggtgg taattataat tacctgtata gattgtttag gaagtctaat 1380
ctcaaacctt ttgagagaga tatttcaact gaaatctatc aggccggtag cacaccttgt 1440
aatggtgttg aaggttttaa ttgttacttt cctttacaat catatggttt ccaacccact 1500
aatggtgttg gttaccaacc atacagagta gtagtacttt cttttgaact tctacatgca 1560
ccagcaactg tttgtggacc taaaaagtct actaatttgg ttaaaaacaa atgtgtcaat 1620
ttcaacttca atggtttaac aggcacaggt gttcttactg agtctaacaa aaagtttctg 1680
cctttccaac aatttggcag agacattgct gacactactg atgctgtccg tgatccacag 1740
acacttgaga ttcttgacat tacaccatgt tcttttggtg gtgtcagtgt tataacacca 1800
ggaacaaata cttctaacca ggttgctgtt ctttatcagg gtgttaactg cacagaagtc 1860
cctgttgcta ttcatgcaga tcaacttact cctacttggc gtgtttattc tacaggttct 1920
aatgtttttc aaacacgtgc aggctgttta ataggggctg aacatgtcaa caactcatat 1980
gagtgtgaca tacccattgg tgcaggtata tgcgctagtt atcagactca gactaattct 2040
ccttcgcggg caggtagtgt agctagtcaa tccatcattg cctacactat gtcacttggt 2100
gcagaaaatt cagttgctta ctctaataac tctattgcca tacccacaaa ttttactatt 2160
agtgttacca cagaaattct accagtgtct atgaccaaga catcagtaga ttgtacaatg 2220
tacatttgtg gtgattcaac tgaatgcagc aatcttttgt tgcaatatgg cagtttttgt 2280

-continued

```
acacaattaa accgtgcttt aactggaata gctgttgaac aagacaaaaa cacccaagaa   2340

gtttttgcac aagtcaaaca aatttacaaa acaccaccaa ttaaagattt tggtggtttt   2400

aatttttcac aaatattacc agatccatca aaaccaagca agaggtcacc tattgaagat   2460

ctacttttca acaaagtgac acttgcagat gctggcttca tcaaacaata tggtgattgc   2520

cttggtgata ttgctgctag agacctcatt tgtgcacaaa agtttaacgg ccttactgtt   2580

ttgccacctt tgctcacaga tgaaatgatt gctcaataca cttctgcact gttagcgggt   2640

acaatcactt ctggttggac ctttggtgca ggtcctgcat tacaaatacc atttcctatg   2700

caaatggctt ataggtttaa tggtattgga gttacacaga atgttctcta tgagaaccaa   2760

aaattgattg ccaaccaatt taatagtgct attggcaaaa ttcaagactc actttcttcc   2820

acaccaagtg cacttggaaa acttcaagat gtggtcaacc aaaatgcaca agctttaaac   2880

acgcttgtta aacaacttag ctccaatttt ggtgcaattt caagtgtttt aaatgatatc   2940

ctttcacgtc ttgacccacc tgaggctgaa gtgcaaattg ataggttgat cacaggcaga   3000

cttcaaagtt tgcagacata tgtgactcaa caattaatta gagctgcaga aatcagagct   3060

tctgctaatc ttgctgctac taaaatgtca gagtgtgtac ttggacaatc aaaaagagtt   3120

gatttttgtg gaaagggcta tcatcttatg tccttccctc agtcagcacc tcatggtgta   3180

gtcttcttgc atgtgactta tgtccctgca caagaaaaga acttcacaac tgctcctgcc   3240

atttgtcatg atggaaaagc acactttcct cgtgaaggtg tctttgtttc aaatggcaca   3300

cactggtttg taacacaaag gaatttttat gaaccacaaa tcattactac agacaacaca   3360

tttgtgtctg gtaactgtga tgttgtaata ggaattgtca acaacacagt ttatgatcct   3420

ttgcaacctg aattagactc attcaaggag gagttagata aatattttaa gaatcataca   3480

tcaccagatg ttgatttagg tgacatctct ggcattaatg cttcagttgt aaacattcaa   3540

aaagaaattg accgcctcaa tgaggttgcc aagaatttaa atgaatctct catcgatctc   3600

caagaacttg gaaagtatga gcagtatata aaatggccat ggtacatttg gctaggtttt   3660

atagctggct tgattgccat agtaatggtg acaattatgc tttgctgtat gaccagttgc   3720

tgtagttgtc tcaagggctg ttgttcttgt ggatcctgct gcaaatttga tgaagacgac   3780

tctgagccag tgctcaaagg agtcaaatta cattacacat aa                      3822
```

<210> SEQ ID NO 68
<211> LENGTH: 1273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80
```

-continued

```
Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495
```

-continued

```
Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Gly Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Ser Arg Ala Gly Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Pro Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Pro Ala Leu Gln Ile
                885                 890                 895

Pro Phe Pro Met Gln Met Ala Tyr Arg Phe Asn Gly Ile Gly Val Thr
            900                 905                 910
```

-continued

```
Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Pro Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270
```

<210> SEQ ID NO 69
<211> LENGTH: 816
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 69
gccaccatgt tcgtgtttct ggtgctgctg cctctggtgt ccagccagcg ggtgcagccc 60
accgaatcca tcgtgcggtt ccccaatatc accaatctgt gccccttcgg cgaggtgttc 120
aatgccacca gattcgcctc tgtgtacgcc tggaaccgga agcggatcag caattgcgtg 180
gccgactact ccgtgctgta caactccgcc agcttcagca ccttcaagtg ctacggcgtg 240
tcccctacca agctgaacga cctgtgcttc acaaacgtgt acgccgacag cttcgtgatc 300
cggggagatg aagtgcggca gattgcccct ggacagacag gcaagatcgc cgactacaac 360
tacaagctgc ccgacgactt caccggctgt gtgattgcct ggaacagcaa caacctggac 420
tccaaagtcg gcggcaacta caattacctg taccggctgt tccggaagtc caatctgaag 480
cccttcgagc gggacatctc caccgagatc tatcaggccg gcagcacccc ttgtaacggc 540
gtggaaggct tcaactgcta cttcccactg cagtcctacg gctttcagcc cacaaatggc 600
gtgggctatc agccctacag agtggtggtg ctgagcttcg aactgctgca tgcccctgcc 660
acagtgtgcg gccctaagaa aagcaccaat ctcgtgaaga acaaatgcgt gaacttcgga 720
tccggaggtg gatacatccc ggaggcccct agggacggtc aagcttacgt gagaaaggac 780
ggcgaatggg ttctgctgtc gaccttcttg ggataa 816

<210> SEQ ID NO 70
<211> LENGTH: 271
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 70

Ala Thr Met Phe Val Phe Leu Val Leu Leu Pro Leu Val Ser Ser Gln
1 5 10 15

Arg Val Gln Pro Thr Glu Ser Ile Val Arg Phe Pro Asn Ile Thr Asn
20 25 30

Leu Cys Pro Phe Gly Glu Val Phe Asn Ala Thr Arg Phe Ala Ser Val
35 40 45

Tyr Ala Trp Asn Arg Lys Arg Ile Ser Asn Cys Val Ala Asp Tyr Ser
50 55 60

Val Leu Tyr Asn Ser Ala Ser Phe Ser Thr Phe Lys Cys Tyr Gly Val
65 70 75 80

Ser Pro Thr Lys Leu Asn Asp Leu Cys Phe Thr Asn Val Tyr Ala Asp
85 90 95

Ser Phe Val Ile Arg Gly Asp Glu Val Arg Gln Ile Ala Pro Gly Gln
100 105 110

Thr Gly Lys Ile Ala Asp Tyr Asn Tyr Lys Leu Pro Asp Asp Phe Thr
115 120 125

Gly Cys Val Ile Ala Trp Asn Ser Asn Asn Leu Asp Ser Lys Val Gly
130 135 140

Gly Asn Tyr Asn Tyr Leu Tyr Arg Leu Phe Arg Lys Ser Asn Leu Lys
145 150 155 160

Pro Phe Glu Arg Asp Ile Ser Thr Glu Ile Tyr Gln Ala Gly Ser Thr
165 170 175

Pro Cys Asn Gly Val Glu Gly Phe Asn Cys Tyr Phe Pro Leu Gln Ser
180 185 190

```
Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Gly
225                 230                 235                 240

Ser Gly Gly Gly Tyr Ile Pro Glu Ala Pro Arg Asp Gly Gln Ala Tyr
                245                 250                 255

Val Arg Lys Asp Gly Glu Trp Val Leu Leu Ser Thr Phe Leu Gly
            260                 265                 270


<210> SEQ ID NO 71
<211> LENGTH: 3822
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

atgtttgttt ttcttgtttt attgccacta gtctctagtc agtgtgttaa tcttacaacc     60

agaactcaat tacccccctgc atacactaat tctttcacac gtggtgttta ttaccctgac    120

aaagttttca gatcctcagt tttacattca actcaggact tgttcttacc tttcttttcc    180

aatgttactt ggttccatgc tatacatgtc tctgggacca atggtactaa gaggtttgat    240

aaccctgtcc taccatttaa tgatggtgtt tattttgctt ccactgagaa gtctaacata    300

ataagaggct ggatttttgg tactacttta gattcgaaga cccagtccct acttattgtt    360

aataacgcta ctaatgttgt tattaaagtc tgtgaatttc aattttgtaa tgatccattt    420

ttgggtgttt attaccacaa aaacaacaaa agttggatgg aaagtgagtt cagagtttat    480

tctagtgcga ataattgcac ttttgaatat gtctctcagc cttttcttat ggaccttgaa    540

ggaaaacagg gtaatttcaa aaatcttagg gaatttgtgt ttaagaatat tgatggttat    600

tttaaaatat attctaagca cacgcctatt aatttagtgc gtgatctccc tcagggtttt    660

tcggctttag aaccattggt agatttgcca ataggtatta acatcactag gtttcaaact    720

ttacttgctt tacatagaag ttatttgact cctggtgatt cttcttcagg ttggacagct    780

ggtgctgcag cttattatgt gggttatctt caacctagga cttttctatt aaaatataat    840

gaaaatggaa ccattacaga tgctgtagac tgtgcacttg accctctctc agaaacaaag    900

tgtacgttga aatccttcac tgtagaaaaa ggaatctatc aaacttctaa ctttagagtc    960

caaccaacag aatctattgt tagatttcct aatattacaa acttgtgccc ttttggtgaa   1020

gtttttaacg ccaccagatt tgcatctgtt tatgcttgga acaggaagag aatcagcaac   1080

tgtgttgctg attattctgt cctatataat tccgcatcat tttccacttt taagtgttat   1140

ggagtgtctc ctactaaatt aaatgatctc tgctttacta atgtctatgc agattcattt   1200

gtaattagag gtgatgaagt cagacaaatc gctccagggc aaactggaaa gattgctgat   1260

tataattata aattaccaga tgattttaca ggctgcgtta tagcttggaa ttctaacaat   1320

cttgattcta aggttggtgg taattataat tacctgtata gattgtttag gaagtctaat   1380

ctcaaacctt ttgagagaga tatttcaact gaaatctatc aggccggtag cacaccttgt   1440

aatggtgttg aaggttttaa ttgttacttt cctttacaat catatggttt ccaacccact   1500

tatggtgttg gttaccaacc atacagagta gtagtacttt cttttgaact tctacatgca   1560
```

-continued

```
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgat gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg gtgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cattcgcggg caggtagtgt agctagtcaa tccatcattg cctacactat gtcacttggt   2100
gcagaaaatt cagttgctta ctctaataac tctattgcca tacccataaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcacc tattgaagat   2460
ctacttttca acaaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtcctgcat tacaaatacc atttcctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acaccaagtg cacttggaaa acttcaagat gtggtcaacc aaaatgcaca agctttaaac   2880
acgcttgtta aacaacttag ctccaatttt ggtgcaattt caagtgtttt aaatgatatc   2940
cttgcacgtc ttgacccacc tgaggctgaa gtgcaaattg ataggttgat cacaggcaga   3000
cttcaaagtt tgcagacata tgtgactcaa caattaatta gagctgcaga aatcagagct   3060
tctgctaatc ttgctgctac taaaatgtca gagtgtgtac ttggacaatc aaaaagagtt   3120
gatttttgtg gaaagggcta tcatcttatg tccttccctc agtcagcacc tcatggtgta   3180
gtcttcttgc atgtgactta tgtccctgca caagaaaaga acttcacaac tgctcctgcc   3240
atttgtcatg atggaaaagc acactttcct cgtgaaggtg tctttgtttc aaatggcaca   3300
cactggtttg taacacaaag gaatttttat gaaccacaaa tcattactac acacaacaca   3360
tttgtgtctg gtaactgtga tgttgtaata ggaattgtca acaacacagt ttatgatcct   3420
ttgcaacctg aattagactc attcaaggag gagttagata aatattttaa gaatcataca   3480
tcaccagatg ttgatttagg tgacatctct ggcattaatg cttcagttgt aaacattcaa   3540
aaagaaattg accgcctcaa tgaggttgcc aagaatttaa atgaatctct catcgatctc   3600
caagaacttg gaaagtatga gcagtatata aaatggccat ggtacatttg gctaggtttt   3660
atagctggct tgattgccat agtaatggtg acaattatgc tttgctgtat gaccagttgc   3720
tgtagttgtc tcaagggctg ttgttcttgt ggatcctgct gcaaatttga tgaagacgac   3780
tctgagccag tgctcaaagg agtcaaatta cattacacat aa                      3822
```

<210> SEQ ID NO 72
<211> LENGTH: 1273

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380
```

-continued

```
Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Tyr Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Asp Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Gly Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser His Ser Arg Ala Gly Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Ile Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800
```

-continued

```
Asn Phe Ser Gln Ile Leu Pro Asp Pro Ser Lys Pro Ser Lys Arg Ser
                805                 810                 815

Pro Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Pro Ala Leu Gln Ile
                885                 890                 895

Pro Phe Pro Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Pro Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ala Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr His Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200
```

```
Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270


<210> SEQ ID NO 73
<211> LENGTH: 3813
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

atgtttgttt ttcttgtttt attgccacta gtctctagtc agtgtgttaa tcttacaacc     60

agaactcaat taccccctgc atacactaat tctttcacac gtggtgttta ttaccctgac    120

aaagttttca gatcctcagt tttacattca actcaggact tgttcttacc tttcttttcc    180

aatgttactt ggttccatgc tatatctggg accaatggta ctaagaggtt tgataaccct    240

gtcctaccat ttaatgatgg tgtttatttt gcttccactg agaagtctaa cataataaga    300

ggctggattt ttggtactac tttagattcg aagacccagt ccctacttat tgttaataac    360

gctactaatg ttgttattaa agtctgtgaa tttcaatttt gtaatgatcc atttttgggt    420

gtttaccaca aaaacaacaa aagttggatg gaaagtgagt tcagagttta ttctagtgcg    480

aataattgca cttttgaata tgtctctcag cctttcttta tggaccttga aggaaaacag    540

ggtaatttca aaaatcttag ggaatttgtg tttaagaata ttgatggtta ttttaaaata    600

tattctaagc acacgcctat taatttagtg cgtgatctcc ctcagggttt ttcggcttta    660

gaaccattgg tagatttgcc aataggtatt aacatcacta ggtttcaaac tttacttgct    720

ttacatagaa gttatttgac tcctggtgat tcttcttcag gttggacagc tggtgctgca    780

gcttattatg tgggttatct tcaacctagg acttttctat taaaatataa tgaaaatgga    840

accattacag atgctgtaga ctgtgcactt gaccctctct cagaaacaaa gtgtacgttg    900

aaatccttca ctgtagaaaa aggaatctat caaacttcta actttagagt ccaaccaaca    960

gaatctattg ttagatttcc taatattaca aacttgtgcc cttttggtga agtttttaac   1020

gccaccagat ttgcatctgt ttatgcttgg aacaggaaga gaatcagcaa ctgtgttgct   1080

gattattctg tcctatataa ttccgcatca ttttccactt ttaagtgtta tggagtgtct   1140

cctactaaat taaatgatct ctgctttact aatgtctatg cagattcatt tgtaattaga   1200

ggtgatgaag tcagacaaat cgctccaggg caaactggaa agattgctga ttataattat   1260

aaattaccag atgattttac aggctgcgtt atagcttgga attctaacaa tcttgattct   1320

aaggttggtg gtaattataa ttacctgtat agattgttta ggaagtctaa tctcaaacct   1380

tttgagagag atatttcaac tgaaatctat caggccggta gcacaccttg taatggtgtt   1440

gaaggtttta attgttactt tcctttacaa tcatatggtt tccaacccac ttatggtgtt   1500

ggttaccaac catacagagt agtagtactt tcttttgaac ttctacatgc accagcaact   1560
```

-continued

```
gtttgtggac ctaaaaagtc tactaatttg gttaaaaaca aatgtgtcaa tttcaacttc   1620
aatggtttaa caggcacagg tgttcttact gagtctaaca aaaagtttct gcctttccaa   1680
caatttggca gagacattga tgacactact gatgctgtcc gtgatccaca gacacttgag   1740
attcttgaca ttacaccatg ttcttttggt ggtgtcagtg ttataacacc aggaacaaat   1800
acttctaacc aggttgctgt tctttatcag ggtgttaact gcacagaagt ccctgttgct   1860
attcatgcag atcaacttac tcctacttgg cgtgtttatt ctacaggttc taatgttttt   1920
caaacacgtg caggctgttt aataggggct gaacatgtca acaactcata tgagtgtgac   1980
atacccattg gtgcaggtat atgcgctagt tatcagactc agactaattc tcattcgcgg   2040
gcaggtagtg tagctagtca atccatcatt gcctacacta tgtcacttgg tgcagaaaat   2100
tcagttgctt actctaataa ctctattgcc atacccataa attttactat tagtgttacc   2160
acagaaattc taccagtgtc tatgaccaag acatcagtag attgtacaat gtacatttgt   2220
ggtgattcaa ctgaatgcag caatcttttg ttgcaatatg gcagtttttg tacacaatta   2280
aaccgtgctt taactggaat agctgttgaa caagacaaaa acacccaaga agtttttgca   2340
caagtcaaac aaatttacaa aacaccacca attaaagatt ttggtggttt taatttttca   2400
caaatattac cagatccatc aaaaccaagc aagaggtcac ctattgaaga tctacttttc   2460
aacaaagtga cacttgcaga tgctggcttc atcaaacaat atggtgattg ccttggtgat   2520
attgctgcta gagacctcat ttgtgcacaa aagtttaacg gccttactgt tttgccacct   2580
ttgctcacag atgaaatgat tgctcaatac acttctgcac tgttagcggg tacaatcact   2640
tctggttgga cctttggtgc aggtcctgca ttacaaatac catttcctat gcaaatggct   2700
tataggttta atggtattgg agttacacag aatgttctct atgagaacca aaaattgatt   2760
gccaaccaat ttaatagtgc tattggcaaa attcaagact cactttcttc cacaccaagt   2820
gcacttggaa aacttcaaga tgtggtcaac caaaatgcac aagctttaaa cacgcttgtt   2880
aaacaactta gctccaattt tggtgcaatt tcaagtgttt taaatgatat ccttgcacgt   2940
cttgacccac ctgaggctga agtgcaaatt gataggttga tcacaggcag acttcaaagt   3000
ttgcagacat atgtgactca acaattaatt agagctgcag aaatcagagc ttctgctaat   3060
cttgctgcta ctaaaatgtc agagtgtgta cttggacaat caaaaagagt tgatttttgt   3120
ggaaagggct atcatcttat gtccttccct cagtcagcac ctcatggtgt agtcttcttg   3180
catgtgactt atgtccctgc acaagaaaag aacttcacaa ctgctcctgc catttgtcat   3240
gatggaaaag cacactttcc tcgtgaaggt gtctttgttt caaatggcac acactggttt   3300
gtaacacaaa ggaattttta tgaaccacaa atcattacta cacacaacac atttgtgtct   3360
ggtaactgtg atgttgtaat aggaattgtc aacaacacag tttatgatcc tttgcaacct   3420
gaattagact cattcaagga ggagttagat aaatatttta agaatcatac atcaccagat   3480
gttgatttag gtgacatctc tggcattaat gcttcagttg taaacattca aaaagaaatt   3540
gaccgcctca atgaggttgc caagaattta aatgaatctc tcatcgatct ccaagaactt   3600
ggaaagtatg agcagtatat aaaatggcca tggtacattt ggctaggttt tatagctggc   3660
ttgattgcca tagtaatggt gacaattatg ctttgctgta tgaccagttg ctgtagttgt   3720
ctcaagggct gttgttcttg tggatcctgc tgcaaatttg atgaagacga ctctgagcca   3780
gtgctcaaag gagtcaaatt acattacaca taa                                3813
```

<210> SEQ ID NO 74
<211> LENGTH: 1270

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile Ser Gly Thr Asn Gly Thr Lys Arg Phe Asp Asn Pro
65                  70                  75                  80

Val Leu Pro Phe Asn Asp Gly Val Tyr Phe Ala Ser Thr Glu Lys Ser
                85                  90                  95

Asn Ile Ile Arg Gly Trp Ile Phe Gly Thr Thr Leu Asp Ser Lys Thr
            100                 105                 110

Gln Ser Leu Leu Ile Val Asn Asn Ala Thr Asn Val Val Ile Lys Val
        115                 120                 125

Cys Glu Phe Gln Phe Cys Asn Asp Pro Phe Leu Gly Val Tyr His Lys
    130                 135                 140

Asn Asn Lys Ser Trp Met Glu Ser Glu Phe Arg Val Tyr Ser Ser Ala
145                 150                 155                 160

Asn Asn Cys Thr Phe Glu Tyr Val Ser Gln Pro Phe Leu Met Asp Leu
                165                 170                 175

Glu Gly Lys Gln Gly Asn Phe Lys Asn Leu Arg Glu Phe Val Phe Lys
            180                 185                 190

Asn Ile Asp Gly Tyr Phe Lys Ile Tyr Ser Lys His Thr Pro Ile Asn
        195                 200                 205

Leu Val Arg Asp Leu Pro Gln Gly Phe Ser Ala Leu Glu Pro Leu Val
    210                 215                 220

Asp Leu Pro Ile Gly Ile Asn Ile Thr Arg Phe Gln Thr Leu Leu Ala
225                 230                 235                 240

Leu His Arg Ser Tyr Leu Thr Pro Gly Asp Ser Ser Ser Gly Trp Thr
                245                 250                 255

Ala Gly Ala Ala Ala Tyr Tyr Val Gly Tyr Leu Gln Pro Arg Thr Phe
            260                 265                 270

Leu Leu Lys Tyr Asn Glu Asn Gly Thr Ile Thr Asp Ala Val Asp Cys
        275                 280                 285

Ala Leu Asp Pro Leu Ser Glu Thr Lys Cys Thr Leu Lys Ser Phe Thr
    290                 295                 300

Val Glu Lys Gly Ile Tyr Gln Thr Ser Asn Phe Arg Val Gln Pro Thr
305                 310                 315                 320

Glu Ser Ile Val Arg Phe Pro Asn Ile Thr Asn Leu Cys Pro Phe Gly
                325                 330                 335

Glu Val Phe Asn Ala Thr Arg Phe Ala Ser Val Tyr Ala Trp Asn Arg
            340                 345                 350

Lys Arg Ile Ser Asn Cys Val Ala Asp Tyr Ser Val Leu Tyr Asn Ser
        355                 360                 365

Ala Ser Phe Ser Thr Phe Lys Cys Tyr Gly Val Ser Pro Thr Lys Leu
    370                 375                 380

```
Asn Asp Leu Cys Phe Thr Asn Val Tyr Ala Asp Ser Phe Val Ile Arg
385                 390                 395                 400

Gly Asp Glu Val Arg Gln Ile Ala Pro Gly Gln Thr Gly Lys Ile Ala
                405                 410                 415

Asp Tyr Asn Tyr Lys Leu Pro Asp Asp Phe Thr Gly Cys Val Ile Ala
            420                 425                 430

Trp Asn Ser Asn Asn Leu Asp Ser Lys Val Gly Gly Asn Tyr Asn Tyr
        435                 440                 445

Leu Tyr Arg Leu Phe Arg Lys Ser Asn Leu Lys Pro Phe Glu Arg Asp
    450                 455                 460

Ile Ser Thr Glu Ile Tyr Gln Ala Gly Ser Thr Pro Cys Asn Gly Val
465                 470                 475                 480

Glu Gly Phe Asn Cys Tyr Phe Pro Leu Gln Ser Tyr Gly Phe Gln Pro
                485                 490                 495

Thr Tyr Gly Val Gly Tyr Gln Pro Tyr Arg Val Val Val Leu Ser Phe
            500                 505                 510

Glu Leu Leu His Ala Pro Ala Thr Val Cys Gly Pro Lys Lys Ser Thr
        515                 520                 525

Asn Leu Val Lys Asn Lys Cys Val Asn Phe Asn Phe Asn Gly Leu Thr
    530                 535                 540

Gly Thr Gly Val Leu Thr Glu Ser Asn Lys Lys Phe Leu Pro Phe Gln
545                 550                 555                 560

Gln Phe Gly Arg Asp Ile Asp Asp Thr Thr Asp Ala Val Arg Asp Pro
                565                 570                 575

Gln Thr Leu Glu Ile Leu Asp Ile Thr Pro Cys Ser Phe Gly Gly Val
            580                 585                 590

Ser Val Ile Thr Pro Gly Thr Asn Thr Ser Asn Gln Val Ala Val Leu
        595                 600                 605

Tyr Gln Gly Val Asn Cys Thr Glu Val Pro Val Ala Ile His Ala Asp
    610                 615                 620

Gln Leu Thr Pro Thr Trp Arg Val Tyr Ser Thr Gly Ser Asn Val Phe
625                 630                 635                 640

Gln Thr Arg Ala Gly Cys Leu Ile Gly Ala Glu His Val Asn Asn Ser
                645                 650                 655

Tyr Glu Cys Asp Ile Pro Ile Gly Ala Gly Ile Cys Ala Ser Tyr Gln
            660                 665                 670

Thr Gln Thr Asn Ser His Ser Arg Ala Gly Ser Val Ala Ser Gln Ser
        675                 680                 685

Ile Ile Ala Tyr Thr Met Ser Leu Gly Ala Glu Asn Ser Val Ala Tyr
    690                 695                 700

Ser Asn Asn Ser Ile Ala Ile Pro Ile Asn Phe Thr Ile Ser Val Thr
705                 710                 715                 720

Thr Glu Ile Leu Pro Val Ser Met Thr Lys Thr Ser Val Asp Cys Thr
                725                 730                 735

Met Tyr Ile Cys Gly Asp Ser Thr Glu Cys Ser Asn Leu Leu Leu Gln
            740                 745                 750

Tyr Gly Ser Phe Cys Thr Gln Leu Asn Arg Ala Leu Thr Gly Ile Ala
        755                 760                 765

Val Glu Gln Asp Lys Asn Thr Gln Glu Val Phe Ala Gln Val Lys Gln
    770                 775                 780

Ile Tyr Lys Thr Pro Pro Ile Lys Asp Phe Gly Gly Phe Asn Phe Ser
785                 790                 795                 800
```

-continued

```
Gln Ile Leu Pro Asp Pro Ser Lys Pro Ser Lys Arg Ser Pro Ile Glu
                805                 810                 815

Asp Leu Leu Phe Asn Lys Val Thr Leu Ala Asp Ala Gly Phe Ile Lys
            820                 825                 830

Gln Tyr Gly Asp Cys Leu Gly Asp Ile Ala Ala Arg Asp Leu Ile Cys
        835                 840                 845

Ala Gln Lys Phe Asn Gly Leu Thr Val Leu Pro Pro Leu Leu Thr Asp
    850                 855                 860

Glu Met Ile Ala Gln Tyr Thr Ser Ala Leu Leu Ala Gly Thr Ile Thr
865                 870                 875                 880

Ser Gly Trp Thr Phe Gly Ala Gly Pro Ala Leu Gln Ile Pro Phe Pro
                885                 890                 895

Met Gln Met Ala Tyr Arg Phe Asn Gly Ile Gly Val Thr Gln Asn Val
            900                 905                 910

Leu Tyr Glu Asn Gln Lys Leu Ile Ala Asn Gln Phe Asn Ser Ala Ile
        915                 920                 925

Gly Lys Ile Gln Asp Ser Leu Ser Ser Thr Pro Ser Ala Leu Gly Lys
    930                 935                 940

Leu Gln Asp Val Val Asn Gln Asn Ala Gln Ala Leu Asn Thr Leu Val
945                 950                 955                 960

Lys Gln Leu Ser Ser Asn Phe Gly Ala Ile Ser Ser Val Leu Asn Asp
                965                 970                 975

Ile Leu Ala Arg Leu Asp Pro Pro Glu Ala Glu Val Gln Ile Asp Arg
            980                 985                 990

Leu Ile Thr Gly Arg Leu Gln Ser  Leu Gln Thr Tyr Val  Thr Gln Gln
        995                 1000                1005

Leu Ile  Arg Ala Ala Glu Ile  Arg Ala Ser Ala Asn  Leu Ala Ala
    1010                1015                1020

Thr Lys  Met Ser Glu Cys Val  Leu Gly Gln Ser Lys  Arg Val Asp
    1025                1030                1035

Phe Cys  Gly Lys Gly Tyr His  Leu Met Ser Phe Pro  Gln Ser Ala
    1040                1045                1050

Pro His  Gly Val Val Phe Leu  His Val Thr Tyr Val  Pro Ala Gln
    1055                1060                1065

Glu Lys  Asn Phe Thr Thr Ala  Pro Ala Ile Cys His  Asp Gly Lys
    1070                1075                1080

Ala His  Phe Pro Arg Glu Gly  Val Phe Val Ser Asn  Gly Thr His
    1085                1090                1095

Trp Phe  Val Thr Gln Arg Asn  Phe Tyr Glu Pro Gln  Ile Ile Thr
    1100                1105                1110

Thr His  Asn Thr Phe Val Ser  Gly Asn Cys Asp Val  Val Ile Gly
    1115                1120                1125

Ile Val  Asn Asn Thr Val Tyr  Asp Pro Leu Gln Pro  Glu Leu Asp
    1130                1135                1140

Ser Phe  Lys Glu Glu Leu Asp  Lys Tyr Phe Lys Asn  His Thr Ser
    1145                1150                1155

Pro Asp  Val Asp Leu Gly Asp  Ile Ser Gly Ile Asn  Ala Ser Val
    1160                1165                1170

Val Asn  Ile Gln Lys Glu Ile  Asp Arg Leu Asn Glu  Val Ala Lys
    1175                1180                1185

Asn Leu  Asn Glu Ser Leu Ile  Asp Leu Gln Glu Leu  Gly Lys Tyr
    1190                1195                1200
```

```
Glu Gln  Tyr Ile Lys Trp Pro  Trp Tyr Ile Trp Leu  Gly Phe Ile
    1205                 1210                 1215

Ala Gly  Leu Ile Ala Ile Val  Met Val Thr Ile Met  Leu Cys Cys
    1220                 1225                 1230

Met Thr  Ser Cys Cys Ser Cys  Leu Lys Gly Cys Cys  Ser Cys Gly
    1235                 1240                 1245

Ser Cys  Cys Lys Phe Asp Glu  Asp Asp Ser Glu Pro  Val Leu Lys
    1250                 1255                 1260

Gly Val  Lys Leu His Tyr Thr
    1265                 1270


<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Lys His Lys His Lys His Lys His Lys
1               5


<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

His Lys His Lys His Lys His Lys His Lys
1               5                   10


<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys His Lys His Lys His Lys His Lys His
1               5                   10


<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

His Lys His Lys His Lys His Lys His Lys His
1               5                   10


<210> SEQ ID NO 79
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 79

Lys His Lys His His Lys His His Lys His His Lys His His Lys His
1               5                   10                  15

His Lys His Lys
            20


<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Lys His His His Lys His His His Lys His His His Lys His His His
1               5                   10                  15

Lys


<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Lys His His His Lys His His His Lys His His His His Lys His His
1               5                   10                  15

His Lys


<210> SEQ ID NO 82
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (18)..(18)
<223> OTHER INFORMATION: D-amino acid

<400> SEQUENCE: 82

Lys His His His Lys His His His Lys His His His His Lys His His
1               5                   10                  15

His Lys
```

<210> SEQ ID NO 83
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

His Lys His His His Lys His His His Lys His His His His Lys His
1               5                   10                  15

His His Lys

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

His His Lys His His His Lys His His His Lys His His His His Lys
1               5                   10                  15

His His His Lys
            20

<210> SEQ ID NO 85
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Lys His His His His Lys His His His His Lys His His His His Lys
1               5                   10                  15

His His His His Lys
            20

<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys His His His Lys His His His Lys His His His Lys His His His
1               5                   10                  15

His Lys

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Lys His His His Lys His His His His Lys His His His Lys His His
1 5 10 15

His Lys

<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Lys His His His Lys His His His His Lys His His His Lys His His
1 5 10 15

His His Lys

<210> SEQ ID NO 89
<211> LENGTH: 3822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89
atgtttgttt ttcttgtttt attgccacta gtctctagtc agtgtgttaa tcttacaacc 60
agaactcaat taccccctgc atacactaat tctttcacac gtggtgttta ttaccctgac 120
aaagttttca gatcctcagt tttacattca actcaggact tgttcttacc tttcttttcc 180
aatgttactt ggttccatgc tatacatgtc tctgggacca atggtactaa gaggtttgat 240
aaccctgtcc taccatttaa tgatggtgtt tattttgctt ccactgagaa gtctaacata 300
ataagaggct ggatttttgg tactacttta gattcgaaga cccagtccct acttattgtt 360
aataacgcta ctaatgttgt tattaaagtc tgtgaatttc aattttgtaa tgatccattt 420
ttgggtgttt attaccacaa aaacaacaaa agttggatgg aaagtgagtt cagagtttat 480
tctagtgcga ataattgcac ttttgaatat gtctctcagc cttttcttat ggaccttgaa 540
ggaaaacagg gtaatttcaa aaatcttagg gaatttgtgt ttaagaatat tgatggttat 600
tttaaaatat attctaagca cacgcctatt aatttagtgc gtgatctccc tcagggtttt 660
tcggctttag aaccattggt agatttgcca ataggtatta acatcactag gtttcaaact 720
ttacttgctt tacatagaag ttatttgact cctggtgatt cttcttcagg ttggacagct 780
ggtgctgcag cttattatgt gggttatctt caacctagga cttttctatt aaaatataat 840
gaaaatggaa ccattacaga tgctgtagac tgtgcacttg accctctctc agaaacaaag 900
tgtacgttga aatccttcac tgtagaaaaa ggaatctatc aaacttctaa ctttagagtc 960
caaccaacag aatctattgt tagatttcct aatattacaa acttgtgccc ttttggtgaa 1020
gtttttaacg ccaccagatt tgcatctgtt tatgcttgga acaggaagag aatcagcaac 1080
tgtgttgctg attattctgt cctatataat tccgcatcat tttccacttt taagtgttat 1140
ggagtgtctc ctactaaatt aaatgatctc tgctttacta atgtctatgc agattcattt 1200
gtaattagag gtgatgaagt cagacaaatc gctccagggc aaactggaaa gattgctgat 1260
tataattata aattaccaga tgattttaca ggctgcgtta tagcttggaa ttctaacaat 1320

-continued

```
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg gtgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
ccttcgcggg caggtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctacttttca acaaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acagcaagtg cacttggaaa acttcaagat gtggtcaacc aaaatgcaca agctttaaac   2880
acgcttgtta aacaacttag ctccaatttt ggtgcaattt caagtgtttt aaatgatatc   2940
ctttcacgtc ttgacccacc tgaggctgaa gtgcaaattg ataggttgat cacaggcaga   3000
cttcaaagtt tgcagacata tgtgactcaa caattaatta gagctgcaga aatcagagct   3060
tctgctaatc ttgctgctac taaaatgtca gagtgtgtac ttggacaatc aaaaagagtt   3120
gatttttgtg gaaagggcta tcatcttatg tccttccctc agtcagcacc tcatggtgta   3180
gtcttcttgc atgtgactta tgtccctgca caagaaaaga acttcacaac tgctcctgcc   3240
atttgtcatg atggaaaagc acactttcct cgtgaaggtg tctttgtttc aaatggcaca   3300
cactggtttg taacacaaag gaatttttat gaaccacaaa tcattactac agacaacaca   3360
tttgtgtctg gtaactgtga tgttgtaata ggaattgtca acaacacagt ttatgatcct   3420
ttgcaacctg aattagactc attcaaggag gagttagata aatattttaa gaatcataca   3480
tcaccagatg ttgatttagg tgacatctct ggcattaatg cttcagttgt aaacattcaa   3540
aaagaaattg accgcctcaa tgaggttgcc aagaatttaa atgaatctct catcgatctc   3600
caagaacttg gaaagtatga gcagtatata aaatggccat ggtacatttg gctaggtttt   3660
atagctggct tgattgccat agtaatggtg acaattatgc tttgctgtat gaccagttgc   3720
```

tgtagttgtc tcaagggctg ttgttcttgt ggatcctgct gcaaatttga tgaagacgac 3780
tctgagccag tgctcaaagg agtcaaatta cattacacat aa 3822

<210> SEQ ID NO 90
<211> LENGTH: 1273
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

Val Asp Cys Ala Leu Asp Pro Leu Ser Glu Thr Lys Cys Thr Leu Lys
290 295 300

Ser Phe Thr Val Glu Lys Gly Ile Tyr Gln Thr Ser Asn Phe Arg Val
305 310 315 320

Gln Pro Thr Glu Ser Ile Val Arg Phe Pro Asn Ile Thr Asn Leu Cys
325 330 335

-continued

```
Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Gly Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Ser Arg Ala Gly Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750
```

```
Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155
```

-continued

```
His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270
```

<210> SEQ ID NO 91
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 91
gccatccacg tgagcggcac caacggcacc aagagg 36

<210> SEQ ID NO 92
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 92
gccctgcaca ggagctacct gacccccggc gacagcagca gcggc 45

<210> SEQ ID NO 93
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 93
aacaacctgg acagcaaggt gggcggcaac tac 33

<210> SEQ ID NO 94
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 94
accgagatct accaggccgg cagcaccccc tgcaacggcg tggagggctt c 51

<210> SEQ ID NO 95
<211> LENGTH: 30

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 95
cagacccaga ccaacagccc caggagggcc 30

<210> SEQ ID NO 96
<211> LENGTH: 30
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 96
gugaucaccc ccggcaccaa caccagcaac 30

<210> SEQ ID NO 97
<211> LENGTH: 30
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 97
accgugugcg gccccaagaa gagcaccaac 30

<210> SEQ ID NO 98
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 98
cccgcccagg agaagaacuu caccacc 27

<210> SEQ ID NO 99
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 99
guggagcagg acaagaacac ccaggag 27

<210> SEQ ID NO 100
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 100
aacaaccugg acagcaaggu gggcggc 27

<210> SEQ ID NO 101
<211> LENGTH: 45
<212> TYPE: RNA

-continued

<213> ORGANISM: Artificial Sequence
<220> FEATURE:
<223> OTHER INFORMATION: Description of Artificial Sequence: Synthetic oligonucleotide

<400> SEQUENCE: 101
uacuaccaca agaacaacaa gagcuggaug gagagcgagu ucagg 45

<210> SEQ ID NO 102
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 102
gccauccacg ugagcggcac caacggcacc aagagg 36

<210> SEQ ID NO 103
<211> LENGTH: 45
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 103
gcccugcaca ggagcuaccu gacccccggc gacagcagca gcggc 45

<210> SEQ ID NO 104
<211> LENGTH: 33
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 104
aacaaccugg acagcaaggu gggcggcaac uac 33

<210> SEQ ID NO 105
<211> LENGTH: 51
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 105
accgagaucu accaggccgg cagcaccccc ugcaacggcg uggagggcuu c 51

<210> SEQ ID NO 106
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 106
cagacccaga ccaacagccc caggagggcc 30

<210> SEQ ID NO 107
<211> LENGTH: 4
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 107

His His His Lys
1


<210> SEQ ID NO 108
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108

tactaccaca agaacaacaa gagctggatg gagagcgagt tcagg                    45
```

COMPOSITION AND METHOD OF mRNA VACCINES AGAINST NOVEL CORONAVIRUS INFECTION

CROSS-REFERENCE TO RELATED APPLICATIONS

This application claims priority to U.S. Provisional application No. 62/971,834, filed Feb. 7, 2020, 63/058,463, filed Jul. 29, 2020, and 63/130,581, filed Dec. 24, 2020, the contents of each of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on May 4, 2021, is named 3949.0001C_SL.txt and is 122,225 bytes in size.

FIELD OF INVENTION

Prophylactic and therapeutic agents for vaccination, prevention and treatment of 2019-nCoV infection are provided, together with methods for their use.

BACKGROUND

Novel Coronavirus (2019-nCoV) Infection: Biology and Pathology

Coronaviruses (CoVs) have repeatedly crossed species barriers and some have emerged as important human pathogens. During the past two decades, two coronaviruses infecting animals have evolved and caused outbreaks in humans: SARS-CoV (2002, Betacoronavirus, subgenus Sarbecovirus), and MERS-CoV (2012, Betacoronavirus, subgenus Merbecovirus) [Drosten et al., *New Engl J Med.* 2003; 348: 1967-1976; Zaki et al., *New Engl J Med.* 2012; 367: 1814-1820]. On 31 Dec. 2019, the Wuhan Municipal Health Commission in Wuhan City, Hubei province, China reported a cluster of 27 pneumonia cases of unknown etiology, including seven severe cases, with a common reported link to Wuhan's Huanan Seafood Wholesale Market (a wholesale fish and live animal market selling different animal species) [Wuhan City Health Committee (WCHC). Wuhan Municipal Health and Health Commission's briefing on the current pneumonia epidemic situation in our city 2019 (updated 31 Dec. 2019 14 Jan. 2020). Available from: http://wjw.wuhan.gov.cn/front/web/showDetail/2019123108989]. The 2019-nCoV is a new strain of coronavirus that has not been previously identified in humans [Zhu et al., *N Engl J Med.* 382:727-733 (2020)]. The outbreak has rapidly spread to affect other parts of China and outside the country. Cases have now been detected in several countries in Asia, but also in Australia, Europe and North America. It appears that the 2019-nCoV can be spread through human-human contact via respiratory droplets [Li et al., *N Engl J Med.* 2020; 382. 1199-1207].

Genetic analysis revealed that 2019-nCoV is closely related to SARS-CoV and genetically clusters within the genus Betacoronavirus, forming a distinct clade in lineage B of the subgenus Sarbecovirus together with two bat-derived SARS-like strains. The virus genome consists of six major open reading frames (ORFs) common to coronaviruses and a number of other accessory genes. Further analysis indicates that some of the 2019-nCoV genes shared less than 80% sequence identity to SARS-CoV. However, the seven conserved replicase (RdRP) domains in ORF1ab that were used for CoV species classification, are 94.6% AA sequence identical between 2019-nCoV and SARS-CoV, implying the two belong to the same species. Angiotensin converting enzyme II (ACE2), a membrane exopeptidase, was known as the cell receptor for SARS-CoV. This receptor also has been shown to be used by 2019-nCoV for entry into human cells. Domain 266-330 (numbering based on the sequence of the mature protein) has been shown to be essential for interaction of 2019-nCoV with ACE2 [Veljkovic et al., F1000Research. 2020; 9: 52.].

Current Prophylaxis and Therapeutics for Novel Coronavirus (2019-nCoV)

At present, the sequences of 287,543 full genomes of 2019-nCoV have been submitted on GISAID [GISAID, Newly discovered betacoronavirus, Wuhan 2019-2020 (2019); https://www.gisaid.org/.] by China CDC, etc., including one that has been released on GenBank (Accession: MN908947.3) [http://www.ncbi.nlm.nih.gov/genbank/.]. Currently, there are only two emergency use authorized vaccines and no licensed vaccines for preventing coronavirus infections, including 2019-nCoV infections.

Advantages of mRNA Vaccines

Vaccination is the most successful medical approach to disease prevention and control. The successful development and use of vaccines has saved thousands of lives and large amounts of money. A key advantage of RNA vaccines is that RNA can be produced in the laboratory from a DNA template using readily available materials, less expensively and faster than conventional vaccine production, which can require the use of chicken eggs or other mammalian cells. In addition, mRNA vaccines have the potential to streamline vaccine discovery and development, and facilitate a rapid response to emerging infectious diseases [Maruggi et al., *Mol Ther.* 2019; 27(4): 757-772

Preclinical and clinical trials have shown that mRNA vaccines provide a safe and long-lasting immune response in animal models and humans. mRNA vaccines against infectious diseases may be developed as prophylactic or therapeutic treatments. mRNA vaccines expressing antigens of infectious pathogens have been shown to induce potent T cell and humoral immune responses [Pardi et al., *Nat Rev Drug Discov.* 2018; 17: 261-279.]. The production procedure to generate mRNA vaccines is cell-free, simple, and rapid, compared to production of whole microbe, live attenuated, and subunit vaccines. This fast and simple manufacturing process makes mRNA a promising bio-product that can potentially fill the gap between emerging infectious disease and the desperate need for effective vaccines.

SUMMARY OF THE INVENTION

Compositions are provided containing an effective amount of a messenger ribonucleic acid (mRNA) that contains an open reading frame (ORF) encoding a 2019-nCoV protein or protein fragment formulated in a pharmaceutically acceptable carrier, where the mRNA and the carrier form a polymeric nanoparticle. The 2019-nCoV protein may be a spike (S) protein or spike (S) subunit. The ORF may be an mRNA encoding a peptide such as the peptides having a sequence of selected from SEQ ID 14 to 31, or 50-66. The ORF may contain for example, an mRNA have a sequences as shown in SEQ ID Nos. 32 to 49 or SEQ ID No. 91 to 106 or 108. The ORF may be selected from mRNA molecules encoding the amino acid sequence selected from SEQ ID No. 11, 13, 68, 70, 72, 74 and 90. The ORF may have a sequence such as SEQ ID No. 1-4, 10, 12, 67, 69, 71, 73 or 89.

These composition may also contain an mRNA containing all or part of orf1a and/or orf1b, where the mRNA encodes a 2019-nCoV non-structural protein polymerase and/or RdRp. The ORF may be an mRNA having a sequence such as SEQ ID NO: 5 or 6. The ORF may encode all or part of the 2019 nCoV encoding envelope (E), membrane (M), and/or nucleocapsid (N) protein. These compositions may also contain one or more mRNA sequences encoding all or part of the 2019 nCoV encoding envelope (E), membrane (M), and/or nucleocapsid (N) protein. The ORF may be selected from mRNA molecules having a sequence shown in SEQ ID No. 7, 8, or 9.

In any of these compositions, the mRNA may be chemically modified with one or more N1-methyl-pseudouridine and/or pseudouridine residues. The uridine residues in the mRNA may all be N1-methyl pseudouridine or pseudouridine.

In any of these compositions the mRNA molecule may further contain a 3'-UTR, a 5'-UTR and optionally further contains additional elements that (a) stabilize the composition and (b) enhance expression of the polypeptide encoded by the ORF. The 5'-UTR may contain an m7G cap structure and a start codon and/or the 3'-UTR may contain a stop codon and a polyA tail.

The composition may contain more than one ORF and may encode at least two polypeptides.

The composition may contain a polymeric nanoparticle carrier that contains a Histidine-Lysine co-polymer (HKP). Examples of suitable HKP include, but are not limited to polymers having side chains selected from SEQ ID NO:75-88.

Also provided are methods of making a composition as described above by expressing the ORF in a linear in vitro transcription (IVT) system or by a plasmid DNA (pDNA) vector delivery system.

The compositions as described above may be made by contacting a composition containing the ORF(s) with an HKP, where the mRNA and the HKP self-assemble into nanoparticles. The composition may further contain a lipid, where the lipid optionally may be a cationic lipid.

Also provided are methods of treating a subject suffering from a 2019-nCoV infection by administering to the subject a pharmaceutically effective amount of a composition as described above. The composition may be atomized by a nebulizer inhalation system prior to or during administration. The nebulizer system may be a portable nebulizer for whole respiratory tract drug delivery. The composition may be administered by subcutaneous injection, intramuscular injection, or intraperitoneal injection (i.p).

BRIEF DESCRIPTION OF THE DRAWINGS

FIGS. 4A-4K show spike protein ORF mRNA sequences.

FIGS. 5A-5C show D614G mutated spike protein ORF mRNA and protein sequences.

FIGS. 6A-6B show SARS RBD mRNA sequence, and the amino acid sequence for D614G Mutated Spike Protein ORF.

FIGS. 7A-7F show mRNA and amino acid sequences for polypeptide epitopes for 2019-nCoV.

FIGS. 8A-8C show the D614G_S6P_DNA and amino acid sequences.

FIGS. 9A-9B show RBD trimer DNA and amino acid sequences.

FIGS. 10A-10F show VUI-202012 DNA and amino acid sequences.

FIG. 11 shows HKP peptide sequences.

FIGS. 12A-12B show D614G S2P DNA Sequence.

FIG. 13 shows D614G S2P amino acid sequence.

FIGS. 14A-14C show the sequences of mRNA molecules encoding peptide epitopes of 2019-nCoV.

DETAILED DESCRIPTION

Prophylactic and therapeutic agents for vaccination, prevention and treatment of 2019-nCoV infection are provided. Pharmaceutical compositions are provided that contain mRNA sequences formulated with pharmaceutical excipients. The composition of the mRNA-based pharmaceutical formulation contains mRNA sequences coding viral proteins necessary for coronavirus infection and replication, and a specific carrier. Suitable carriers include Histidine-Lysine Co-polymers (HKP), and/or HKP plus a lipid, such as a cationic lipid. Methods also are provided for using these pharmaceutical compositions, including methods of treatment, process development, and specific delivery routes and regimens.

Target Selection and Design for mRNA Vaccine Against 2019-nCoV

In regard to the protein level, the predicted genes of 2019-nCoVs were identified and annotated. It was found that the annotation results of all six 2019-nCoV genomes are identical, including seven functional proteins (pp1a, E2 glycoprotein precursor, hypothetical protein sars3a, matrix protein, hypothetical protein sars6, hypothetical protein sars7a, nucleocapsid protein) verified in SARS-CoV-like coronavirus [B. Buchfink, et al., *Nat Methods.* 2015; 12: 59-60]. These results illustrate the similarities and differences between 2019-nCoV and SARS-CoV or MERS-CoV-like Coronaviruses.

The predominant human receptor for 2019-nCoV is believed to be human angiotensin-converting enzyme 2 (ACE2). Domain 288-330 of S1 protein from the 2019-nCoV represents a promising therapeutic and/or vaccine target [Veljkovic et al., supra]. Generally, the spike (S) protein of coronavirus including 2019-nCoV is the major inducer of neutralizing antibodies, and the receptor-binding domain (RBD) in the S1 subunit of S protein contains multiple conformational neutralizing epitopes [He et al., *J Immunol.* 2005; 174(8): 4908-4915]. This suggests that recombinant proteins containing RBD and vectors including mRNAs encoding the RBD sequence can be used to develop safe and effective 2019-nCoV vaccines.

As described herein, a new type of mRNA vaccine (mRNA-1273) has been developed using an immunogenic composition that contains a messenger ribonucleic acid (mRNA) containing an open reading frame (ORF) encoding one or more epitopes from one or more proteins of 2019-nCoV. The mRNA is formulated in a pharmaceutically acceptable carrier containing a polymeric nanoparticle and/or a liposomal nanoparticle. The composition may be administered to a subject in an amount effective to induce a specific immune response against 2019-nCoV in the subject. The composition may contain more than one type of mRNA molecule. Each additionally copy enhances the immunostimulatory activities of the composition. All the mRNAs encode antigens that are highly immunogenic and that are required for 2019-nCoV to enter epithelial cells, which is the first step in 2019-nCoV infection.

Figure 3B:
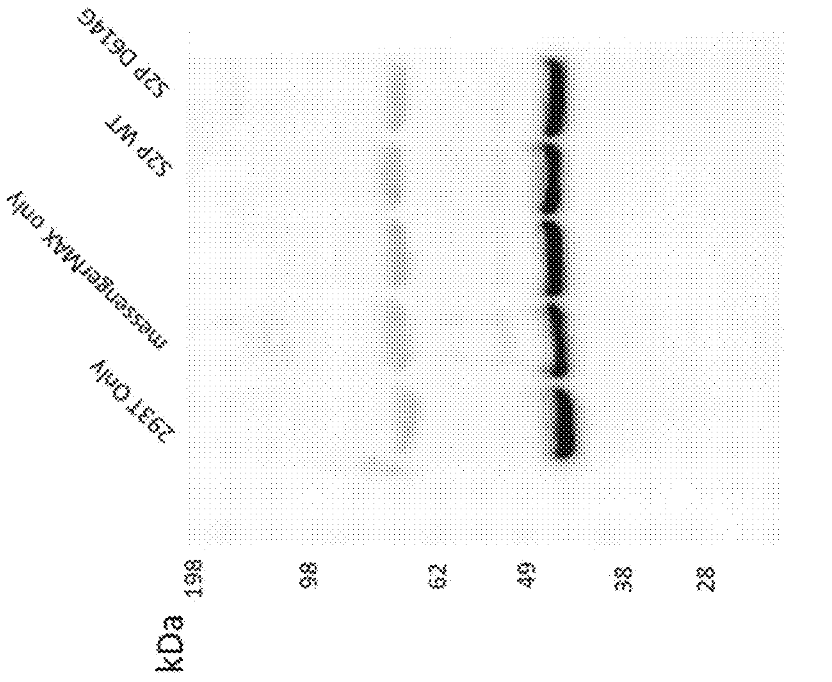
FIGS. 3A-3B show Western Blot result of Spike Protein expression after mRNA transient transfection. Transfection condition: ThermoFisher Scientific Lipofectamine MessengerMAX Transfection Reagent protocol (Pin. No. MAN0010803 Rev D.0). Primary antibody: SARS-CoV/SARS-CoV-2 Spike Protein S2 Monoclonal Antibody (ThermoFisher Scientific, MA5-35946). Secondary antibody: Mouse IgG (H+L) Secondary Antibody (ThermoFisher Scientific, A24512). Loading control: HRP Anti-beta Actin antibody (abcam, ab49900).
Figure 3A:
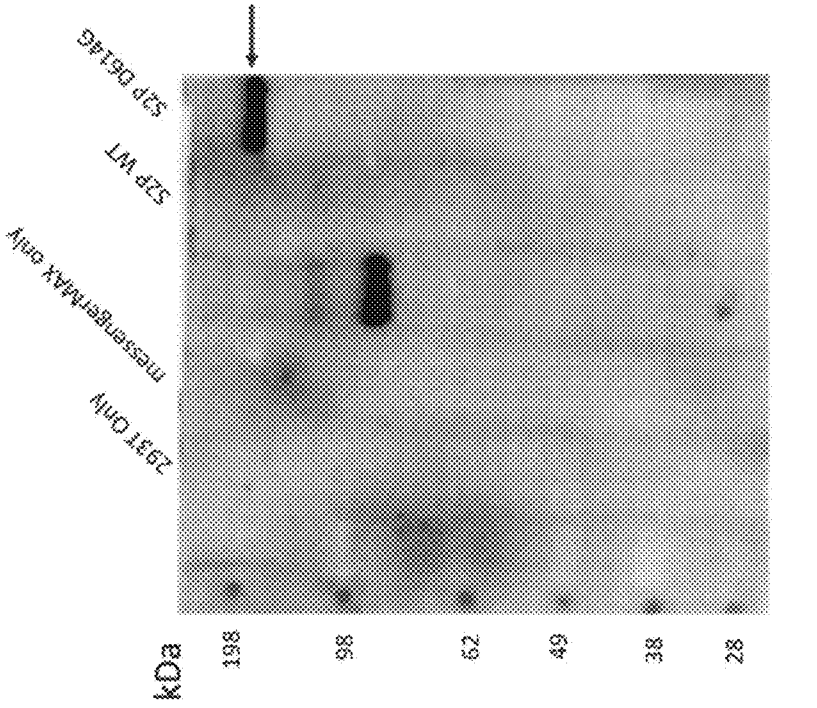

In one embodiment, the composition contains one or more mRNAs encoding the entire spike (S) protein of 2019-nCoV (FIG. 3). The S protein is used by the virus to attach to the host cell receptor. The Spike protein-coding mRNA sequence is long, and therefore in order to improve the efficiencies of mRNA expression systems preparation, it was divided into four regions, where one, some, or all of these regions can be used as mRNA antigen(s) against Spike protein structure (SEQ ID Nos. 1 to 4), when expressed in frame for the Spike protein domains. 24 short peptide fragments that are potential epitopes were selected as targets (SEQ ID Nos. 14 to 31). The short peptide selected is less than 20 amino acids, advantageously less than 15 amino acids. mRNA sequences encoding short peptide sequences were designed using methods that are well known in the art (SEQ ID No. 32 to 49).

Furthermore, compared to other coronavirus, 2019-nCoV has several unique insertions in the spike protein. The amino acid residues in those insertion sites of S protein of 2019-nCoV are identical or similar to the amino acid residues in the replicating protein gp120 or Gag of human immunodeficiency virus type 1 (HIV-1). In another embodiment, a series of mRNA sequences was designed that encode amino acid residues that are identical between 2019-nCoV and HIV-1 (SEQ ID No. 50 to 66), which are recognized by the human immune system.

In another embodiment, the mRNA encodes the D614G variant of the ORF of the spike protein. The coronavirus disease 2019 (COVID-19) outbreak, caused by SARS-CoV-2, has rapidly expanded to a global pandemic. SARS-CoV-2 isolates encoding a D614G mutation in the viral spike (S) protein predominate over time in locales where it is found, implying that this change enhances viral transmission. S proteins with aspartic acid (D614) and glycine (G614) at residue 614 have different functional properties. Specifically, retroviruses pseudotyped with G614 were found to infect ACE2-expressing cells much more efficiently than those with wild type (D614). This greater infectivity was correlated with less 51 shedding and greater incorporation of the S protein into the pseudovirion. Similar results were obtained using virus-like particles produced with SARS-CoV-2 M, N, E, and S proteins. In correlation analyses, spike protein bearing the D614G mutation showed significant positive correlations with fatality rates (r=0.43, P=0.022). These results indicate that spike protein with the D614G mutation is more stable than wild type, which is consistent with epidemiological data suggesting that viruses with the spike D614G mutation transmit more efficiently (SEQ ID No. 10). A vaccine with an ORF that incorporates the D614G mutation was produced because it would more effectively protect against the dominant strain of Sars-Cov-2.

In another embodiment, the mRNA encodes the ORF with SEQ ID NO:89, encoding D614G spike protein precursor S2P.

In another embodiment, the mRNA encodes the ORF with Seq ID No. 67, which incorporates other mutations in the spike protein that have been identified. These include the HV 69-70 deleted spike protein, the Y144 deleted spike protein, the N501Y mutated spike protein, the A570D mutated spike protein, the P681H mutated spike protein, the T7161 mutated spike protein, the F817P modified spike protein, the A892P modified spike protein, the A899P modified spike protein, the A942P modified spike protein, the S982A mutated spike protein, and the D1118H mutated spike protein. Vaccine compositions containing mRNAs encoding one or more of any of these known mutations can be prepared using the methods described herein.

In other embodiments, the mRNA may encode one or more other SARS-CoV-2 viral protein coding sequences including the Envelope (E), Membrane (M), or Nucleocapsid (N) structural proteins. The 2019-nCoV genome is arranged in the order of: 5'-replicase (orf1/ab)-structural proteins [Spike (S)-Envelope (E)-Membrane (M)-Nucleocapsid (N)]-3' (Zulma et al. 2016, Nature Reviews Drug Discovery 15:327-347.), and lacks the hemagglutinin-esterase gene which is characteristically found in lineage A β-CoV. Therefore, various viral proteins other than, or in addition to, the S protein of 2019-nCoV coding mRNA can be applied as the mRNA based vaccination targets. In an embodiment, the viral surface proteins advantageously are targets for an mRNA vaccine, The viral functional proteins responsible for viral polymerase in the region of ORF1a (SEQ ID No. 5) and replication (RdRp) in the region of ORF1b (SEQ ID No. 6) also may be used to prepare a vaccine composition.

Other viral proteins may also be the target of mRNA vaccines. For example, the coronavirus membrane (M) protein is a key player in virion assembly. One of its functions is to mediate the incorporation of the spikes into the viral envelope. The nucleocapsid N-protein is a highly immunogenic phosphoprotein, that is typically highly conserved. The coronavirus N-protein is often used as a marker in diagnostic assays. Coronavirus (CoV) envelope (E) proteins play multiple roles during infection, including virus morphogenesis and pathogenesis. In other embodiments, mRNAs coding for all or part of one or more viral M protein, N protein and E protein as their specific antigens may be selected for use as components in the antigenic vaccine composition (SEQ ID No. 7, 8, 9).

Modifications may be made in the mRNA sequence to prepare the vaccine composition. For example, a 5' cap structure may be added to the mRNA sequence. In one embodiment, a 5'CleanCap is added. This structure uses an initiating capped trimer to yield a naturally occurring 5' cap structure. Advantageously, a poly-A tail is added to the sequence to increase mRNA stability. AU or GU-enriched sequences may be selected in the 3' UTR, while random sequences may be utilized in the 5' UTP to reduce similarity to the host gene sequences. Codon optimization of the mRNA sequence may also be used to improve translation efficiency. Specifically, codons that correspond to lower abundance tRNA species and that therefore lead to lower protein expression are replaced with codons that correspond to higher abundance tRNAs that provide higher levels of protein expression. (Brown, et al. *Protein Expr Purif,* 2008, 59:94-102; Maertens et al., 2010, *Protein Sci,* 9:1312-1326.; Plotkin et al., 2011, *Nat Rev Genet,* 12:32-42.; Kudla et al., 2009, *Science,* 324:255-258.)

Improving mRNA Vaccine Expression Efficiency

To improve mRNA expression efficiency in mammalian cells, mRNA stability may be enhanced by partial chemical modification. To further increase the translation efficiency, short and double strand RNAs derived from aberrant RNA polymerase activities are removed, for example by FPLC, HPLC, or chromatography using cellulose as a matrix. To improve the potency of mRNA vaccines, sequence optimization may be used, together with usage of modified nucleosides, such as pseudouridine (φ), 5-methylcytidine (5mC), Cap-1 structure and optimized codons, which in turn improve translation efficiency. [Do we have any more information about the use of modified nucleosides? Or is that common knowledge? I think codon optimization is common knowledge at this point] During in vitro transcription of mRNA, immature mRNA may be produced as a contaminant which inhibits translation through stimulating innate immune activation (Kariko et al, *Mol Ther.* 2008 16(11): 1833-40.; Andries et al, *J Control Release.* 2015 Nov. 10; 217:337-44.). FPLC and HPLC purification may be used to remove these contaminants.

In the compositions described herein, the template for in vitro transcription of mRNA contains five cis-acting structural elements, namely from 5' to 3': (i) the optimized cap structure, (ii) the optimized 5' untranslated region (UTR), (iii) the codon optimized coding sequence, (iv) the optimized 3' UTR and (v) a stretch of repeated adenine nucleotides (polyA tail) (FIG. 18). (Murray et al, *Mol. Cell. Biol.* 2007, 27, 2791-2799.; Louis et al, *Curr. Opin. Genet. Dev.* 2011, 21, 444-451.; Ferizi et al, *Lab chip* 2015, 15, 3561-3571.; Von Niessen et al, *Mol. Ther.* 2019, 27, 824-836.) These cis-acting structural elements are further optimized in the endeavor for better mRNA features, including half-life and expression level. Provided herein, the 5'-UTR includes a start, but does not encode polypeptide (i.e. it is non-coding). In some embodiments, a 5'-UTR of the present disclosure comprises a cap structure with 7-methylguanosine (7mG) sequences. The 3'-UTR is directly downstream (3') from the stop codon (the codon of an mRNA transcript representing a termination signal) and does not encode a polypeptide (is non-coding). A polyA tail is a special region of mRNA that is downstream from 3'-UTR and contains multiple consecutive adenosine monophosphates; it is required for efficient mRNA production. An mRNA in vitro transcription template is used not only for efficiency of mRNA production but also for the subsequent protein or peptide production In some embodiments, mRNA is produced by in vitro transcription (IVT) from a linear DNA template containing a bacteriophage promoter, the optimized UTR's and the codon optimized sequence by using a RNA polymerase (T7, T3 or SP6) and a mix of the different nucleosides. In other embodiments, the linear DNA template can be cloned into a plasmid DNA (pDNA) as a delivery vector. The plasmid vectors can be adapted for mRNA vaccine production. Commonly used plasmids include pSFV1, pcDNA3 and pTK126, which are all commercially available. One unique mRNA expression system is pEVL (see Grier et al. *Mol Ther Nucleic Acids.* 19; 5:e306 (2016), In some embodiments, the mRNA is a modified mRNA where all uridine residues are replaced by pseudouridines during in vitro transcription. This modification stabilizes the mRNA against enzymatic degradation in the cell, leading to enhanced translation efficiency of the mRNA. The pseudouridines used can be N1-methyl-pseudouridine, or other modifications that are well known in the art such as N6-methyladenosine (m6A), inosine, pseudouridine, 5-methylcytidine (m5C), 5-hydroxymethylcytidine (hm5C), and N1-methyladenosine (m1A). The modification optionally is made throughout the entire mRNA, including the ORF, the 5'UTR and 3'UTR. The skilled artisan will recognize that other modified RNA residues may be used to stabilize the protein 3 dimensional structure and increase protein translation.

To test the level of efficiency, the experiments described in Example 3, 4 and 5 were performed.

Histidine-Lysine (HK) Polypeptides as mRNA Vaccine Delivery Systems

Effective means for transferring nucleic acids into target cells are important tools, both in the basic research setting and in clinical applications. A diverse array of nucleic acid carriers is currently required because the effectiveness of a particular carrier depends on the characteristics of the nucleic acids that is being transfected [Blakney et al. *Biomacromolecules* 2018, 19: 2870-2879. Goncalves et al. *Mol Pharm* 2016; 13: 3153-3163. Kauffman et al. *Biomacromolecules* 2018; 19: 3861-3873. Peng et al. *Biomacromolecules* 2019; 20: 3613-3626. Scholz et al. *J Control Release* 2012; 161: 554-565.]. Among various carriers, non-viral delivery systems have been developed and reported to be more advantageous than the viral delivery system in many aspects [Brito et al. *Adv Genet.* 2015; 89: 179-233]. For example, the large molecular weight branched polyethylenimine (PEI, 25 kDa) is an excellent carrier for plasmid DNA but not for mRNA. However, by decreasing the molecular weight of PEI to 2 kDa, it becomes a more effective carrier of mRNA [Bettinger et al. *Nucleic Acids* Res 2001; 29: 3882-3891.].

The four-branched histidine-lysine (HK) peptide polymer H2K4b has been shown to be a good carrier of large molecular weight DNA plasmids [Leng et al. *Nucleic Acids* Res 2005; 33: e40.], but a poor carrier of relatively low molecular weight siRNA [Leng et al. *J Gene Med* 2005; 7: 977-986.]. Two histidine-rich peptides analogs of H2K4b, namely H3K4b and H3K(+H)4b, were shown to be effective carriers of siRNA [Leng et al. *J Gene Med* 2005; 7: 977-986. Chou et al. *Biomaterials* 2014; 35: 846-855.], although H3K(+H)4b appeared to be modestly more effective [Leng et al. *Mol Ther* 2012; 20: 2282-2290.]. Moreover, the H3K4b carrier of siRNA induced cytokines to a significantly greater degree in vitro and in vivo than H3K(+H)4b siRNA polyplexes [Leng et al. *Mol Ther* 2012; 20: 2282-2290.]. Suitable HK polypeptides are described in WO/2001/047496, WO/2003/090719, and WO/2006/060182, the contents of each of which are incorporated herein in their entireties. These polypeptides have a lysine backbone (three lysine residues) where the lysine side chain ε-amino groups and the N-terminus are coupled to various HK sequences. HK polypeptide carriers can be synthesized by methods that are well-known in the art including, for example, solid-phase synthesis.

It was found that such histidine-lysine peptide polymers ("HK polymers") were surprisingly effective as mRNA carriers, and that they can be used, alone or in combination with liposomes, to provide effective delivery of mRNA into target cells. Similar to PEI and other carriers, initial results suggested HK polymers differ in their ability to carry and release nucleic acids. However, because HK polymers can be reproducibly made on a peptide synthesizer, their amino acid sequence can be easily varied, thereby allowing fine control of the binding and release of mRNAs, as well as the stability of polyplexes containing the HK polymers and mRNA [Chou et al. *Biomaterials* 2014; 35: 846-855. Midoux et al. *Bioconjug Chem* 1999; 10: 406-411. Henig et al. *Journal of American Chemical Society* 1999; 121: 5123-5126.]. When mRNA molecules are admixed with one or more HKP carriers the components self-assemble into nanoparticles.

As described herein, advantageously the HK polymer comprises four short peptide branches linked to a three-lysine amino acid core. The peptide branches consist of histidine and lysine amino acids, in different configurations. The general structure of these histidine-lysine peptide polymers (HK polymers) is shown in Formula I, where R represents the peptide branches and K is the amino acid L-lysine.

Formula I

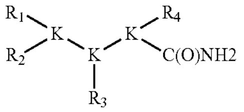

In Formula I where K is L-lysine and each of $R_1$, $R_2$, $R_3$ and $R_4$ is independently a histidine-lysine peptide. The $R_{1-4}$ branches may be the same or different in the HK polymers of the invention. When a R branch is "different", the amino acid sequence of that branch differs from each of the other R branches in the polymer. Suitable R branches used in the HK polymers of the invention shown in Formula I include, but are not limited to, the following R branches $R_A$-$R_{\_J}$:

(SEQ ID NO: 79)
$R_A$ = KHKHHKHHKHHKHHKHHKHK- (SEQ ID NO: 80)
$R_B$ = KHHHKHHHKHHHKHHHK- (SEQ ID NO: 81)
$R_C$ = KHHHKHHHKHHHHKHHHK-

-continued (SEQ ID NO: 82)
$R_D$ = kHHHkHHHkHHHHkHHHk- (SEQ ID NO: 83)
$R_E$ = HKHHHKHHHKHHHHKHHHK- (SEQ ID NO: 84)
$R_F$ = HHKHHHKHHHKHHHHKHHHK- (SEQ ID NO: 85)
$R_G$ = KHHHHKHHHHKHHHHKHHHHK- (SEQ ID NO: 86)
$R_H$ = KHHHKHHHKHHHKHHHHK- (SEQ ID NO: 87)
$R_I$ = KHHHKHHHHKHHHKHHHK- (SEQ ID NO: 88)
$R_J$ = KHHHKHHHHKHHHKHHHHK- Specific HK polymers that may be used in the mRNA compositions include, but are not limited to, HK polymers where each of $R_1$, $R_2$, $R_3$ and $R_4$ is the same and selected from $R_A$-$R_J$ (Table 1). These HK polymers are termed H2K4b, H3K4b, H3K(+H)4b, H3k(+H)4b, H-H3K(+H)4b, HH-H3K(+H)4b, H4K4b, H3K(1+H)4b, H3K(3+H)4b and H3K(1,3+H)4b, respectively. In each of these 10 examples, upper case "K" represents a L-lysine, and lower case "k" represents D-lysine. Extra histidine residues, in comparison to H3K4b, are underlined within the branch sequences. Nomenclature of the HK polymers is as follows:

1) for H3K4b, the dominant repeating sequence in the branches is -HHHK- (SEQ ID NO: 107), thus "H3K" is part of the name; the "4b" refers to the number of branches;
2) there are four -HHHK- (SEQ ID NO: 107) motifs in each branch of H3K4b and analogues; the first -HHHK- (SEQ ID NO: 107) motif ("1") is closest to the lysine core;
3) H3K(+H)4b is an analogue of H3K4b in which one extra histidine is inserted in the second -HHHK- (SEQ ID NO: 107) motif (motif 2) of H3K4b;
4) for H3K(1+H)4b and H3K(3+H)4b peptides, there is an extra histidine in the first (motif 1) and third (motif 3) motifs, respectively; 5) for H3K(1,3+H)4b, there are two extra histidines in both the first and the third motifs of the branches.

TABLE 1

| Polymer | Branch Sequence | Sequence Identifier |
|---|---|---|
| H2K4b | $R_A$ = KHKHHKHHKHHKHHKHHKHK- | (SEQ ID NO: 79) |
| | 4 3 2 1 | |
| H3K4b | $R_B$ = KHHHKHHHKHHHKHHHK- | (SEQ ID NO: 80) |
| K3K(+H)4b | $R_C$= KHHHKHHHKHHHHKHHHK- | (SEQ ID NO: 81) |
| H3k(+H)4b | $R_D$ = kHHHkHHHkHHHHkHHHk- | (SEQ ID NO: 82) |
| H-H3K(+H)4b | $R_E$ = HKHHHKHHHKHHHHKHHHK- | (SEQ ID NO: 83) |
| HH-H3K(+H)4b | $R_F$ = HHKHHHKHHHKHHHHKHHHK- | (SEQ ID NO: 84) |
| H4K4b | $R_G$ = KHHHHKHHHHKHHHHKHHHHK- | (SEQ ID NO: 85) |
| H3K(1 + H)4b | $R_H$ = KHHHKHHHKHHHKHHHHK- | (SEQ ID NO: 86) |
| H3K(3 + H)4b | $R_I$ = KHHHKHHHHKHHHKHHHK- | (SEQ ID NO: 87) |
| H3K(1, 3 + H)4b | $R_J$ = KHHHKHHHHKHHHKHHHHK- | (SEQ ID NO: 88) |

Methods well known in the art, including gel retardation assays, heparin displacement assays and flow cytometry can be performed to assess performance of different formulations containing HK polymer plus liposome in successfully delivering mRNA. Suitable methods are described in, for example, Gujrati et al, | *Mol. Pharmaceutics* 11:2734-2744 (2014), Pärnaste et al., *Mol Ther Nucleic Acids.* 7: 1-10 (2017).

Detection of mRNA uptake into cells can also be achieved using SmartFlare® technology (Millipore Sigma). These smart flares are beads that have a sequence attached that, when recognizing the RNA sequence in the cell, produce an increase in fluorescence that can be analyzed with a fluorescent microscope.

Other methods include measuring protein expressions from the mRNA—for example, an mRNA encoding luciferase can be used to measure the efficiency of transfection using methods that are well known in the art. See, for example, These were done with luciferase mRNA in the latest publication. (He et al, *J Gene Med.* 2021 February; 23(2):e3295). to demonstrate the efficacy of delivering mRNA using a HKP and liposome formulation.

Synergistic Activity of DOTAP and HK Carriers in mRNA Delivery

The combination of H3K(+H)4b and DOTAP (a cationic lipid) surprisingly was synergistic in its ability to carry mRNA into MDA-MB-231 cells (H3K(+H)4b/liposomes vs liposomes, P<0.0001). The combination was about 3-fold and 8-fold more effective as carriers of mRNA than the polymer alone and the cationic lipid carrier, respectively. Not all HK peptides demonstrated the synergistic activity with DOTAP lipid. For example, the combination of H3K4b and DOTAP was less effective than the DOTAP liposomes as carriers of luciferase mRNA. Besides DOTAP, other cationic lipids that may be used with HK peptides include Lipofectin (ThermoFisher), Lipofectamine (ThermoFisher), and DOSPER (FIG. 22).

The D-isomer of H3k (+H)4b, in which the L-lysines in the branches are replaced with D-lysines, was the most effective polymeric carrier (H3k(+H)4b vs. H3K(+H)4b, P<0.05). The D-isomer/liposome carrier of mRNA was nearly 4-fold and 10-fold more effective than the H3k(+H)4b alone and liposome carrier, respectively. Although the D-H3k(+H)4b/lipid combination was modestly more effective than the L-H3K(+H)4b/lipidmbination, this comparison was not statistically different (FIG. 23).

H3K(+H)4b as a Carrier for mRNA Among HK Polymers

Both H3K4b and H3K(+H)4b may be used as carriers of nucleic acids in vitro [Leng et al. *J Gene Med* 2005; 7: 977-986. Chou et al., *Cancer Gene Ther* 2011; 18: 707-716.]. Despite these previous findings, H3K(+H)4b was markedly better as a carrier of mRNA compared to other similar analogues (Table 2).

TABLE 2

| Polymer | Ratio(wt:wt; mRNA:Polymer) | RLU/ug-Protein |
|---|---|---|
| H3K(+H)4b | 1:4 | 1532.9 ± 122.9 |
| | 1:8 | 1656.3 ± 202.5 |
| | 1:12 | 1033.4 ± 197 |
| H3k(+H)4b | 1:4 | 1851.6 ± 138.3 |
| | 1:8 | 1787.2 ± 195.2 |
| | 1:12 | 1982.3 ± 210.7 |
| H3K4b | 1:4 | 156.8 ± 41.8 |
| | 1:8 | 62.1 ± 13. 2 |
| | 1:12 | 18.1 ± 4.0 |

TABLE 2-continued

| Polymer | Ratio(wt:wt; mRNA:Polymer) | RLU/ug-Protein |
|---|---|---|
| H3K(3 + H)4b | 1:4 | 61.7 ± 5.7 |
| | 1:8 | 68.7 ± 3.1 |
| | 1:12 | 59.0 ± 7.5 |
| H3K(1 + H)4b | 1:4 | 24.3 ± 4.5 |
| | 1:8 | 15.0 ± 3.6 |
| | 1:12 | 7.3 ± 2.5 |
| H-H3K(+H)4b | 1:4 | 1107.5 ± 140.4 |
| | 1:8 | 874.6 ± 65.2 |
| | 1:12 | 676.4 ± 25.7 |
| HH-H3K(+H)4b | 1:4 | 1101.9 ± 106.6 |
| | 1:8 | 832.2 ± 75.3 |
| | 1:12 | 739.8 ± 105.4 |
| H4K4b | 1:4 | 896. 4 ± 112. 6 |
| | 1:8 | 821. 8 ± 115. 6 |
| | 1:12 | 522. 4 ± 69. 2 |
| H3K(1, 3 + H)4b | 1:4 | 518. 3 ± 134. 7 |
| | 1:8 | 427. 7 ± 18. 1 |
| | 1:12 | 378 ± 5. 2 |
| H2K4b | 1:4 | 546. 7 ± 70. 1 |
| | 1:8 | 132. 3 ± 58. 5 |
| | 1:12 | 194. 7 ± 18. 4 |

Especially, it has higher mRNA transfection efficiency than H3K4b in various weight:weight (HK:mRNA) ratios. At a 4:1 ratio, luciferase expression was 10-fold higher with H3K(+H)4b than H3K4b in MDA-MB-231 cells without significant cytotoxicity. Moreover, the buffering capacity does not seem to be an essential factor in their transfection differences since the percent of histidines (by weight) in H3K4b and H3K(+H)4b is 68.9 and 70.6%, respectively.

Gel retardation assays show that the electrophoretic mobility of mRNA was delayed by the HK polymers. The retardation effect increased with higher peptide to mRNA weight ratios. However, mRNA was completely retarded in 2:1 ratio of H3K(+H)4b, whereas it was not completely retarded by H3K4b. This suggested that H3K(+H)4b could form a more stable polyplex, which was advantageous for its ability to be a suitable carrier for mRNA delivery.

Further confirmation that the H3K(+H)4b peptide binds more tightly to mRNA was demonstrated with a heparin-displacement assay. Various concentrations of heparin was added into the polyplexes formed with mRNA and HK and it was observed that, particularly at the lower concentrations of heparin, mRNA was released by the H3K4b polymer more readily than the H3K(+H)4b polymer. These data suggest H3K(+H)4b could bind to mRNA and form a more stable polyplex than H3K4b.

With the mRNA labeled with cyanine-5, the uptake of H3K4b and H3K(+H)4b polyplexes into MDA-MB-231 cells was compared using flow cytometry. At different time points (1, 2, and 4 h), the H3K(+H)4b polyplexes were imported into the cells more efficiently than H3K4b polyplexes (data not shown). Similar to these results, fluorescent microscopy indicated that H3K(+H)4b polyplexes localized within the acidic endosomal vesicles significantly more than H3K4b polyplexes (H3K4b vs. H3K(+H)4b, P<0.001). Interestingly, irregularly-shaped H3K4b polyplexes, which did not overlap endocytic vesicles, were likely extracellular and were not observed with H3K(+H)4b polyplexes.

It is known both that HK polymers and cationic lipids (i.e., DOTAP) significantly and independently increase transfection with plasmids [Chen et al. *Gene Ther* 2000; 7: 1698-1705.]. Consequently, whether these lipids together with HK polymers enhanced mRNA transfection was investigated. Notably, the H3K(+H)4b and H3k(+H)4b carriers were significantly better carriers of mRNA than the DOTAP liposomes. The combination of H3K(+H)4b and DOTAP lipid was synergistic in the ability to carry mRNA into MDA-MB-231 cells. The combination was about 3-fold and 8-fold more effective as carriers of mRNA than the polymer alone and the liposome carrier, respectively (H3K(+H)4b/lipid vs. liposomes or H3K(+H)4b). Notably, not all HK peptides demonstrated improved activity with DOTAP lipid. The combination of H3K4b and DOTAP carriers was less effective than the DOTAP liposomes as carriers of luciferase mRNA. The combination of DOTAP and H3K(+H)4b carriers were found to be synergistic in their ability to carry mRNA into cells [He et al. *J Gene Med.* 2020 Nov. 10:e3295].

Administration of mRNA Vaccines

The vaccine formulations described herein may be administered to subjects, including human subjects, by any mode of administration that is conventionally used to administer vaccines. Thus the compositions can be in the form of an aerosol, dispersion, solution, or suspension and can be formulated for inhalation, intramuscular, oral, sublingual, buccal, parenteral, nasal, subcutaneous, intradermal, or topical administration. The term parenteral as used herein includes percutaneous, subcutaneous, intravascular (e.g., intravenous), intramuscular, or intrathecal injection or infusion techniques and the like.

As used herein, an effective dose of a vaccine is the dose required to produce a protective immune response in the subject to whom the vaccine is administered. A protective immune response in the present context is one that prevents or ameliorates disease in a subject challenged with 2019-nCoV. Methods of running clinical trials in multiple subjects to determine whether a vaccine produces a protective immune response are well known in the art.

The vaccine may be administered one or more times. An initial measurement of an immune response to the vaccine may be made by measuring production of antibodies in the subject receiving the vaccine. Methods of measuring antibody production in this manner are also well known in the art. is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize Generally, an amount between 0.1 mg/kg and 100 mg/kg body weight/day of active ingredients is administered dependent upon potency of the formulated composition.

However, their application has until recently been restricted by the instability and inefficient in vivo delivery of mRNA. The methods described herein provide methods of making and using mRNA vaccines with a polypeptide delivery system and a polypeptide nanoparticle delivery system.

The methods described herein may be used in clinical applications of the mRNA include prophylactic and therapeutic vaccines against various diseases, especially infectious diseases.

Example 1: mRNA Synthesis

CleanCap SARS-COV 2 spike protein (S1P and S2P) and CleanCap Enhanced Green Fluorescent Protein (EGFP) expressed mRNA were synthesized and CleanCap SARS-COV 2 spike protein (S6P) was manufactured by TriLink BioTechnologies, Inc, (San Diego, CA) and purified by selective binding of dsRNA to cellulose in an ethanol-containing buffer A chromatography buffer containing 10 mM HEPES (pH 7.2), 0.1 mM EDTA, 125 mM NaCl, 16% ethanol and cellulose fibers were added to microcentrifuge spin columns along with mRNA products and centrifuged. Almost 90% of dsRNA could be removed after this procedure (Baiersdorfer et. al, 2019). Contaminants could be also eliminated using FPLC and HPLC (Kariko et. al, 2011).

Example 2: Peptides (HK Polymers) Preparation

The HK peptide polymers were synthesized on a Rainin Voyager synthesizer (Tucson, AZ) by the biopolymer core facility at the University of Maryland.

Example 3: In-Vitro Transfection of mRNA

To verify the proper protein expression of mRNA, EGFP mRNA and SARS-COV 2 SP, mRNAs were transiently transfected into human embryonic kidney 293T cells (293T cells). Briefly, $4.8\times10^5$ cells were plated into a 6 well plate containing 2 ml of DMEM (10% fetal bovine serum and 1% Penicillin-Streptomycin (ThermoFisher Scientific)). After 24 hr, when the cells were 70-90% confluent, mRNAs were transfected into 293T cells using Lipofectamine Messenger-MAX Transfection Reagent (ThermoFisher Scientific) according to the provided protocol. 293T cells were cultured for two day for in vitro protein expression measurement.

Two HK based polymers associated with cationic liposome DOTAP (1,2-dioleoyl-3-trimethylammonium-propane, Roche), MC3 (DLin-MC3-DMA, ChemScene), and PLA (Polylactic acid) were examined for their ability to carry an EGFP mRNA and SARS-COV 2 SP mRNA into human embryonic kidney 293 cells (HEK 293 cells). Briefly, $4.8\times10^5$ cells were plated into a 6 well plate containing 2 ml of DMEM (10% fetal bovine serum and Penicillin-Streptomycin (ThermoFisher Scientific)). After 24 hr, when the cell were 70-90% confluent, two HK based polymer formulations with EGFP and SPs mRNA added into each well. 293T cell were cultured for two day for In-vitro protein expression measurement.

Example 4: In-Vitro Protein Expression Measurement

Immunofluorescence analysis: After two days of transfection, protein expression was measured by immunofluorescence imaging using a Cytation5 Cell Imaging Multi-Mode Reader (Biotek, Winooski, VT).

Cell lysate preparation: After two days of transfection, culture media was aspirated and cells were washed on ice with ice-cold PBS. Ice-cold lysis buffer (RIPA, ThermoFisher Scientific) with protease inhibitor (ThermoFisher Scientific) was added and cells were incubated for 30 minutes at 4° C. Cells were harvested using a cell scraper and lysed by sonication. Centrifugation at 10,000 g for 20 minutes at 4° C. pelleted cell debris, and the supernatant was transferred to a fresh microcentrifuge tube. The protein concentration of the lysate was determined by Bradford or BCA protein assay for Western blot.

Western blot: Briefly, in each well of a gel, 20-50 ug of protein was with 4×SDS sample buffer (ThermoFisher Scientific), 10× Reducing buffer (ThermoFisher Scientific), and additional ddH2O (ThermoFisher Scientific) with a total loading volume of 25 μl/well. The mixture was denatured by heating at 95° C. for 5 minutes and cooled to room temperature and centrifuged before loading onto a NuPAGE™ 4 to 12%, Bis-Tris gel (ThermoFisher Scientific). After electrophoretic separation, the gel was removed from the cassette and transferred using an iBlot™ 2 Dry Blotting System (ThermoFisher Scientific). The transfer membrane was blocked with 5% fat-free milk powder in TBST for 1 hr at RT, incubated with primary antibody for overnight at 4° C., washed three times with TBST (0.05% Tween20 in TBS) buffer, and incubated with secondary antibody, which is HRP conjugated Mouse IgG (H+L) Secondary Antibody (ThermoFisher Scientific, A24512) for 1 hr at RT. Transfer membrane was developed by Pierce ECL Western Blotting Substrate (ThermoFisher Scientific) and was imaged using chemiluminescent imaging system.

Example 5: In Vivo Formulation Preparation

1. PNI-Genvoy LNP formulation: Lipid nanoparticles were formulated using the GenVoy Platform with PNI NanoAssemblr (Precision NanoSystems, Vancouver, British Columbia, Canada) as the positive control in both in vitro and in vivo assays.

2. HKP(+H) formulation: HKP(+H) stock solution (10 mg/mL) was prepared in nuclease free water. A concentrated stock solution was diluted to 4 mg/mL in water. mRNA working solution (1 mg/mL) was prepared in 1 mM citrate buffer (pH 6.0). The mRNA/HKP(+H) polyplex was formed by mixing equal volumes of 4 mg/mL HKP(+H) and 1 mg/mL mRNA. The mass ratio of HKP(+H) to mRNA is 4:1. The mRNA/HKP(+H) polyplex was incubated for 30 min at room temperature before use. The size of each peptide-based polyplex was determined with the Zetasizer (Malvern Panalytical) prior to transfection or injection.

3. HKP(+H)/DOTAP formulation (post-mixed DOTAP): HKP(+H) stock solution (10 mg/mL) was prepared in nuclease free water. A concentrated stock solution was diluted to 4 mg/mL in water. DOTAP (Sigma-Aldrich) is 1 mg/mL in aqueous buffered solution. mRNA working solution (1 mg/mL) was prepared in 1 mM citrate buffer (pH 6.0). First the mRNA/HKP(+H) polyplex was formed by mixing equal volumes of 4 mg/mL HKP(+H) and 1 mg/mL mRNA. The mRNA/HKP(+H) polyplex was incubated for 30 min at room temperature. Next, the same volume of DOTAP to HKP(+H) solution was added to the mRNA/HKP(+H) polyplex. The mass ratio of HKP(+H)/DOTAP to mRNA was 4:1:1. The mRNA/HKP(+H)/DOTAP nanoparticle was incubated for 30 min at room temperature before use.

4. HKP(+H)/MC3 or HKP(+H)/DOTAP formulations (pre-mixed MC3 or DOTAP): HKP(+H) stock solution (10 mg/mL) was prepared in nuclease-free water. A concentrated stock solution was diluted to 4 mg/mL in water. DOTAP or MC3 is 1 mg/mL in aqueous buffered solution. mRNA working solution (1 mg/mL) was prepared in 1 mM citrate buffer (pH 6.0). Equal volumes of HKP(+H) and MC3 were pre-mixed at a 4:1 mass ratio and the same volume of mRNA to HKP(+H) solution was added to a pre-mixed HKP(+H)/MC3. The mRNA/HKP(+H)/MC3 nanoparticle was formed by mixing pre-mixed 4 mg/mL HKP(+H)/1 mg/mL MC3 and 1 mg/mL mRNA. The mass ratio of HKP(+H)/MC3 to mRNA is 4:1:1. The mRNA/HKP(+H)/MC3 nanoparticle was incubated for 30 min at room temperature before use.

5. HKP(+H)/PLA NP formulation: HKP(+H) stock solution (10 mg/mL) was prepared in nuclease free water. A concentrated stock solution was diluted to 4 mg/mL in water. A poly-L-Lactic Acid (PLA) nanoparticle (5 mg/mL) was prepared in water. mRNA working solution (1 mg/mL) was prepared in 1 mM citrate buffer (pH 6.0). Equal volumes of HKP(+H) and mRNA were mixed at a 4:1 mass ratio. The mRNA/HKP(+H) polyplex was incubated for 30 min at room temperature, and then the same volume of PLA nanoparticle to HKP(+H) solution was added to the mRNA/HKP(+H) nanoparticle so that the mRNA/HKP(+H) polyplex was adsorbed on the surface of the PLA nanoparticle. The mass ratio of HKP(+H)/PLA to mRNA was 4:5:1. The mRNA/HKP(+H)/PLA nanoparticle was incubated for 30 min at room temperature before use.

Example 6: In Vivo Animal Model and Injection

An in vivo study was performed at Antibody and Immunoassay Consultants (AIC) Inc (Gaithersburg, MD). Briefly, 8 6-8 week old female BALB/C were randomized into each group, 4 mice per each group and injected intramuscularly into the right flank with 30 μg of EGFP with different formulations. With the same formulations mentioned above, CleanCap SARS-COV 2 spike protein (S6P) polyplexes were prepared for in vivo analysis and antibody titer measurement and binding.

On day 28, a second injection for boosting was made and on day 35 serum was collected and analyzed by immunoassay (ELISA) for measurement of antibody titer.

Results

Immunofluorescence Analysis

Figure 1:
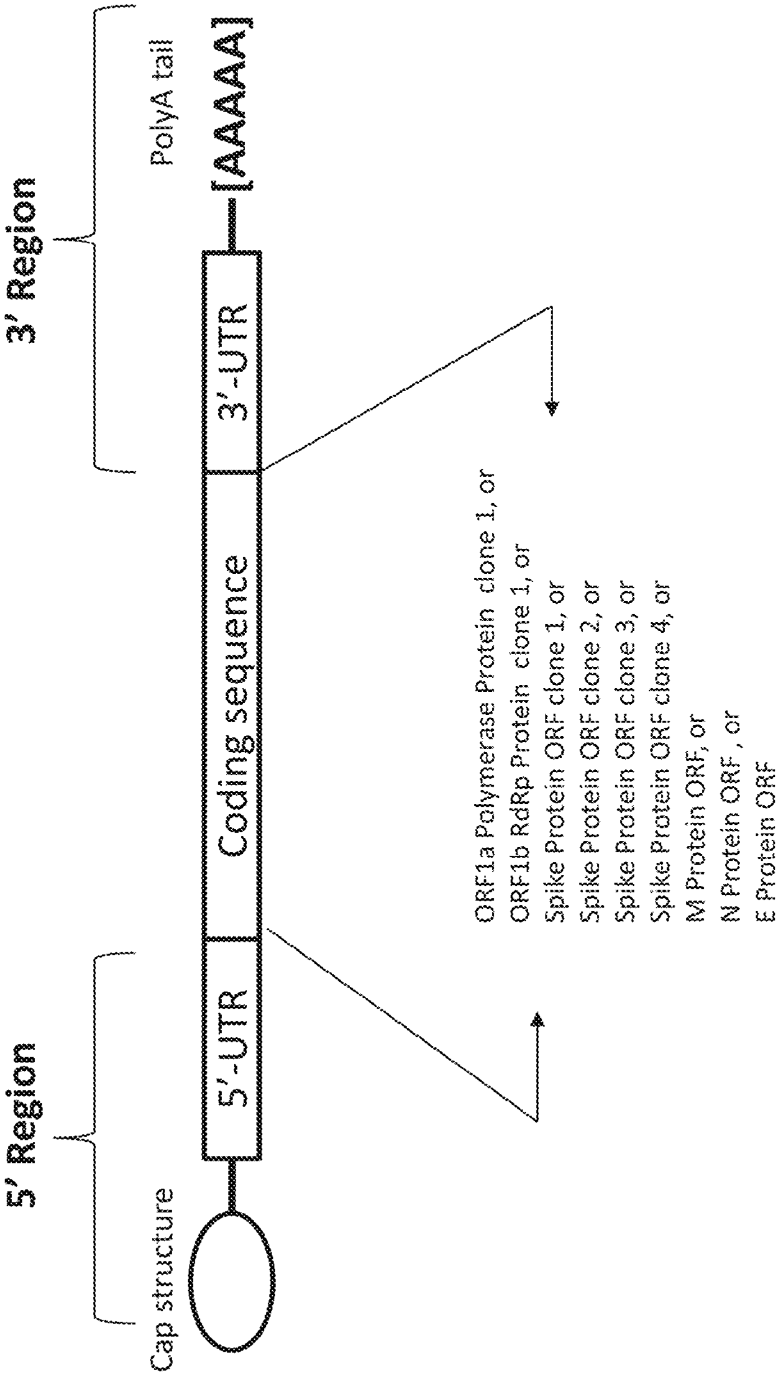
FIG. 1 shows a schematic representation of optimized mRNA vaccine expression structure. This structure is contained in a linear in vitro transcription (IVT) expression system or plasmid DNA delivery vector.
Figure 2:
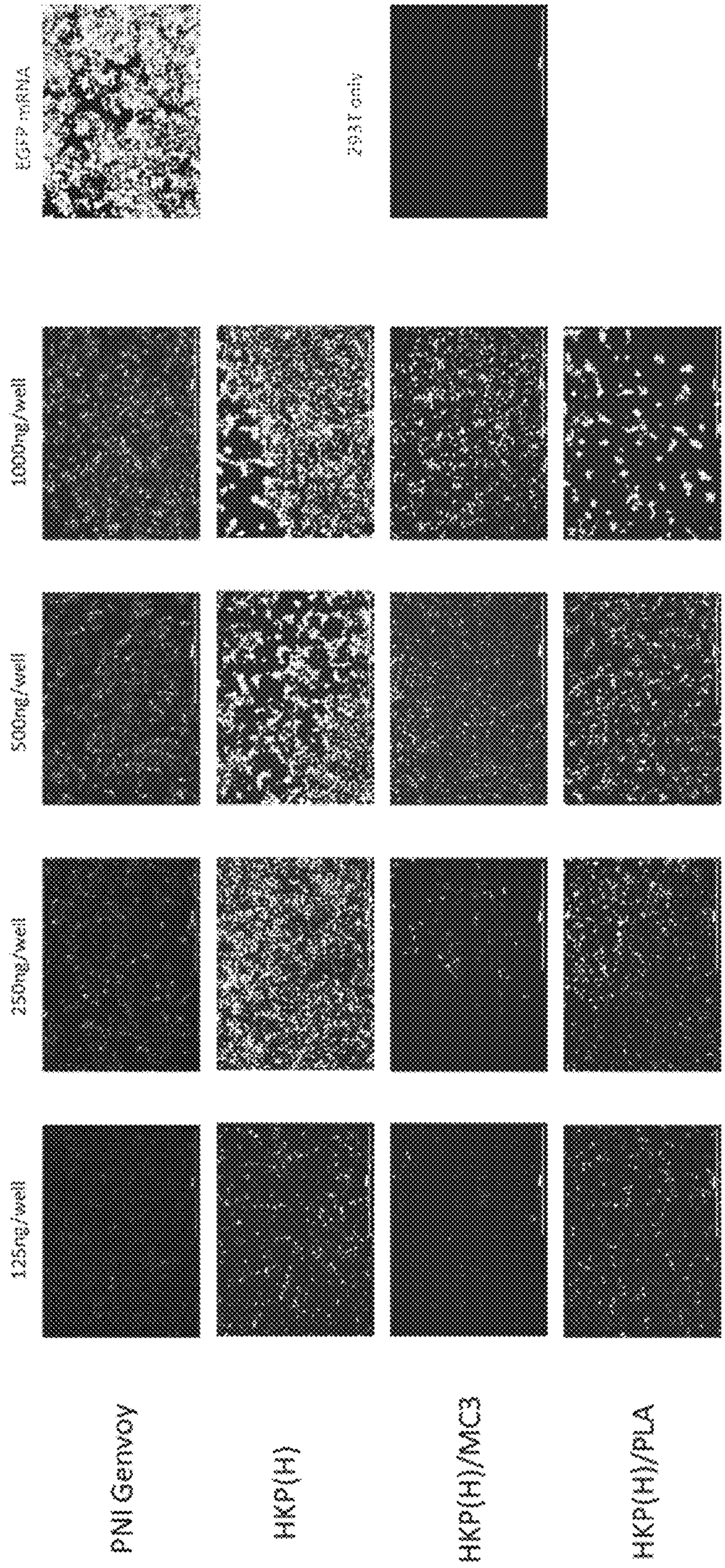
FIG. 2 shows immunofluorescence analysis result of spike protein expression after mRNA transient transfection. Transfection condition: ThermoFisher Scientific Lipofectamine MessengerMAX Transfection Reagent protocol (Pin. No. MAN0010803 Rev D.0).

One week after fabrication, formulations delivered to HEK 293T cells (FIG. 2). All HKP(H) groups proved the possibility to carry mRNA into cells in vitro. Among HKP (H) groups, HKP(H) alone group showed higher EGFP expression than others and PNI Genvoy (positive control).

Western Blot Analysis

Next Western Blot assay performed and results (FIG. 3) showed the expressed spike protein on the cell surface from S1P D614G mRNA delivered group vas underwent shedding after localization to cell membrane. Only S2 domain of spike protein remained on the cell surface. The band size in the Western Blot (70-80 KDa) supported this hypothesis. However the spike protein from S2P D614G showed intact size of the spike protein (180 KDa).

What is claimed is:

1. A composition comprising an effective amount of a messenger ribonucleic acid (mRNA) that comprises an open reading frame (ORF) encoding a 2019-nCoV protein or protein fragment formulated in a pharmaceutically acceptable carrier, wherein said mRNA and said carrier form a polymeric nanoparticle and wherein the 2019-nCoV protein or protein fragment is encoded by SEQ ID NO: 89.

2. The composition of claim 1, wherein the 2019-nCoV protein is a spike (S) protein or spike (S) subunit.

3. The composition of claim 1, wherein the ORF encoding the 2019-nCoV protein or protein fragment is an mRNA molecule encoding the amino acid sequence of SEQ ID NO: 90.

4. The composition of claim 1, wherein said ORF encoding the 2019-nCoV protein or protein fragment comprises any one of SEQ ID NOs: 96 to 105.

5. The composition of claim 1, further comprising an mRNA comprising all or part of orf1a or orf1b or both, wherein said mRNA encodes a 2019-nCoV non-structural protein polymerase or RdRp or both.

6. The composition of claim 5 wherein the 2019-nCov non-structural protein polymerase is encoded by SEQ ID NO: 5 and wherein the 2019-nCov non-structural RdRp is encoded by SEQ ID NO: 6.

7. The composition of claim 1, wherein said ORF encodes all or part of the 2019 nCoV encoding envelope (E), membrane (M), nucleocapsid (N) protein, or any combination thereof, or wherein the composition further comprises one or more mRNA sequences encoding all or part of the 2019 nCoV encoding envelope (E), membrane (M), nucleocapsid (N) protein, or any combination thereof.

8. The composition of claim 7, wherein the M protein is encoded by SEQ ID NO: 7, the N protein is encoded by SEQ ID NO: 8, and the E protein is encoded by SEQ ID NO: 9.

9. The composition according to claim 1, wherein any one or more or all uridine residues in the mRNA are N1-methyl pseudouridine or pseudouridine.

10. The composition of claim 1, wherein the mRNA molecule further comprises a 3'-UTR and a 5'-UTR, and optionally further comprises additional elements that (a) stabilize the composition and (b) enhance expression of the polypeptide encoded by said ORF.

11. The composition of claim 10, wherein the 5'-UTR comprises an m7G cap structure and a start codon, or wherein the 3'-UTR comprises a stop codon and a polyA tail, or both.

12. A method of making the composition of claim 1, comprising expressing said ORF in a linear in vitro transcription (IVT) system, or using a plasmid DNA @DNA) vector delivery system.

13. The composition of claim 1, wherein the composition comprises more than one ORF and encodes at least two polypeptides.

14. The composition of claim 1, wherein the polymeric nanoparticle carrier comprises a Histidine-Lysine co-polymer (HKP) or a lipid or both.

15. The composition of claim 14, wherein the HKP is selected from the group consisting of polymers having side chains selected from SEQ ID NOs: 75-88, or wherein said lipid is a cationic lipid, or both.

16. A method of making a composition according to claim 14, comprising contacting a composition comprising said ORF with an HKP, said mRNA and said HKP self-assemble into nanoparticles.

17. A method of treating a subject with a 2019-nCoV infection comprising administering to said subject a pharmaceutically effective amount of the composition of claim 1.

18. The method of claim 17, wherein the composition is atomized by a nebulizer inhalation system prior to or during administration, and optionally wherein the nebulizer system is a portable nebulizer for whole respiratory tract drug delivery.

19. The method of claim 17, wherein the composition is administered by a method comprising a subcutaneous injection, or an intramuscular injection, or an intraperitoneal injection (i.p.).

* * * * *

UNITED STATES PATENT AND TRADEMARK OFFICE
CERTIFICATE OF CORRECTION

PATENT NO. : 12,029,786 B2
APPLICATION NO. : 17/170876
DATED : July 9, 2024
INVENTOR(S) : Shenggao Tang et al.

Page 1 of 1

It is certified that error appears in the above-identified patent and that said Letters Patent is hereby corrected as shown below:

In the Claims

At Column 112, Line 32, delete "@DNA)" and insert --(pDNA)--

Signed and Sealed this
Twenty-fourth Day of June, 2025

Coke Morgan Stewart
*Acting Director of the United States Patent and Trademark Office*